(12) United States Patent
Kim et al.

(10) Patent No.: US 11,319,289 B2
(45) Date of Patent: May 3, 2022

(54) 5-HYDROXY PYRIDINE-BASED COMPOUND FOR USE AS P2X1 AND P2X3 RECEPTOR ANTAGONIST AND PHARMACEUTICAL COMPOSITION COMPRISING SAME

(71) Applicant: GWANGJU INSTITUTE OF SCIENCE AND TECHNOLOGY, Gwangju (KR)

(72) Inventors: Yong Chul Kim, Gwangju (KR); Young Hwan Jung, Gwangju (KR)

(73) Assignee: GWANGJU INSTITUTE OF SCIENCE AND TECHNOLOGY, Gwangju (KR)

( * ) Notice: Subject to any disclaimer, the term of this patent is extended or adjusted under 35 U.S.C. 154(b) by 0 days.

(21) Appl. No.: 16/494,212

(22) PCT Filed: Mar. 13, 2018

(86) PCT No.: PCT/KR2018/002947
§ 371 (c)(1),
(2) Date: Sep. 13, 2019

(87) PCT Pub. No.: WO2018/169286
PCT Pub. Date: Sep. 20, 2018

(65) Prior Publication Data
US 2020/0131131 A1 Apr. 30, 2020

(30) Foreign Application Priority Data
Mar. 13, 2017 (KR) .................. 10-2017-0031413

(51) Int. Cl.
| | |
|---|---|
| *C07D 213/80* | (2006.01) |
| *A61P 23/00* | (2006.01) |
| *C07D 401/12* | (2006.01) |
| *C07D 471/04* | (2006.01) |
| *C07D 491/048* | (2006.01) |

(52) U.S. Cl.
CPC ............ *C07D 213/80* (2013.01); *A61P 23/00* (2018.01); *C07D 401/12* (2013.01); *C07D 471/04* (2013.01); *C07D 491/048* (2013.01)

(58) Field of Classification Search
CPC .. C07D 213/80; C07D 401/12; C07D 471/04; C07D 491/048; A61P 23/00
USPC ......................................................... 546/290
See application file for complete search history.

(56) References Cited

U.S. PATENT DOCUMENTS

| | | | | |
|---|---|---|---|---|
| 4,730,042 A | * | 3/1988 | Hege .................... | C07D 491/04 544/124 |
| 5,236,620 A | * | 8/1993 | Reiffenrath ............ | C09K 19/20 252/299.61 |
| 9,546,139 B2 | * | 1/2017 | Kim ........................ | A61P 9/10 |

FOREIGN PATENT DOCUMENTS

| | | | | |
|---|---|---|---|---|
| KR | 10-2011-0119058 A | 11/2011 | | |
| WO | WO-8908689 A1 | * | 9/1989 | ............. C09K 19/42 |
| WO | WO-2010100475 A1 | * | 9/2010 | ........... C07D 239/42 |
| WO | WO-2011136459 A1 | * | 11/2011 | ............... A61P 25/00 |

OTHER PUBLICATIONS

Marco Idzko et al , Extracellular ATP triggers and maintains asthmatic airway inflammation by activating dendritic cells. (Year: 2007).*
Joong-Heui Cho et al Desagn and Synthesis of Potent and selective O2X3 receptor antagonists derived from PPADS as potential oain modulators. (Year: 2013).*
Joong-Heui Cho et al. Design and Synthesis of potent and selective P2X3 recptor antagonists derived from PPADS as potential pain modulators. (Year: 2013).*
Cho, J.-H. et al., "Design and Synthesis of Potent and Selective P2X3 Receptor Antagonists Derived from PPADS as Potential Pain Modulators", European Journal of Medicinal Chemistry, 2013, vol. 70, pp. 811-830.
Waibel, M. et al., "Phenethyl Pyridines with Non-polar Internal Substituents as Selective Ligands for Estrogen Receptor Beta", European Journal of Medicinal Chemistry, 2009, vol. 44, No. 9, p. 3560-3570.
Brown, S. G. et al., "Actions of a Series of PPADS Analogs at P2X1 and P2X3 Receptors", Drug Development Research, 2001, vol. 53, No. 4, pp. 281-291.
Jung. Y.-H et al., "Discovery of Potent Antiallodynic Agents for Neuropathic Pain Targeting P2X3 Receptors", ACS Chemical Neuroscience, 2017, [Electronic publishing] Mar. 21, 2017, vol. 8, No. 7, pp. 1465-01478.
International Search Report dated Jun. 28, 2018, in connection with counterpart International Patent Application No. PCT/KR2018/002947.

* cited by examiner

Primary Examiner — Timothy R Rozof
(74) Attorney, Agent, or Firm — Hauptman Ham, LLP

(57) ABSTRACT

The present invention relates to novel 5-hydroxy pyridine-based compounds useful as P2X1 and P2X3 receptor antagonists and compositions comprising the same. The compounds according to the present invention have an activity of strongly antagonizing P2X1 and P2X3 receptors, and thus can be effectively used as a drug for treating or preventing chronic inflammatory diseases or neuropathic pain diseases caused by P2X1 and P2X3 receptor activity.

10 Claims, 15 Drawing Sheets

1 (A-317491)

| 2a (RO-4) | R = H |
|---|---|
| 2b (RO-51) | R = CH(CH$_2$OH)$_2$ |

3 (RO-85)

4 (pyrrolo-pyrimidinone)

5 (Spinorphin)

| Compounds | R₁ | R₂ |
|---|---|---|
| 6a (PPADS) | -OPO(OH)$_2$ | 2': -SO$_3$H<br>4': -SO$_3$H |
| 6b (MRS2159) | -OPO(OH)$_2$ | 4': -CO$_2$H |
| 6c | -CH$_2$COOH | 4': -CO$_2$H |

| Compounds | R₁ | R₂ |
|---|---|---|
| 7a | -OH | -CO$_2$H |
| 7b | -OH | -CH=CHCO$_2$H |
| 7c | -H | -CH=CHCO$_2$H |

| P2X subfamily | % inhibition at 1 µM | % inhibition at 100 nM |
|---|---|---|
| hP2X3 receptor[a] | 60.7 ± 1.8% | 35.5 ± 3.5% |
| rP2X2/3 receptor[a] | 51.0 ± 3.0% | 32.0 ± 0.5% |

[a] The ion current responses evoked by 2 µM ATP in *Xenopus* oocytes expressing recombinant P2X receptors, and % inhibition values at 1 µM, 100 nM of compound 29 was measured for hP2X3, rP2X2/3 receptors (mean ± SEM, n ≥3).

5-HYDROXY PYRIDINE-BASED COMPOUND FOR USE AS P2X1 AND P2X3 RECEPTOR ANTAGONIST AND PHARMACEUTICAL COMPOSITION COMPRISING SAME

CROSS REFERENCE TO RELATED APPLICATION

This present application is a national stage filing under 35 U.S.C § 371 of PCT Application No. PCT/KR2018/002947 filed on Mar. 13, 2018 which is based upon and claims the benefit of priority to Korean Patent Application No. 10-2017-0031413 filed on Mar. 13, 2017 in the Korean Intellectual Property Office. The disclosures of the above-listed applications are hereby incorporated by reference herein in their entirety.

TECHNICAL FIELD

The present invention was made with the support of the Ministry of Science, ICT and Future Planning, under project No. 2014R1A2A1A11052300, which was conducted in the research project titled "Individual Key Studies (promoting technology commercialization)" within the project named "Study on Multitarget Control and Drug Design of Neuropathic Pain Signaling" by the Gwangju Institute of Science and Technology under the management of the National Research Foundation of Korea from Nov. 1, 2014 to Oct. 31, 2016.

This application claims the benefit of priority from Korean Patent Application No. 10-2017-0031413 filed on Mar. 13, 2017 with the Korean Intellectual Property Office, the full disclosure of which is incorporated herein by reference.

The present invention relates to novel 5-hydroxy pyridine-based compound for use as P2X1 and P2X3 receptor antagonist and pharmaceutical composition including same.

BACKGROUND ART

P2X receptors are ligand-gated cation channels that are activated in response to the binding of extracellular adenosine 5'-triphosphate (ATP). It is well known that when the transmembrane pores of P2X receptor is opened, cations such as $Ca^{2+}$, $Na^+$ and $K^+$ enter the cytoplasm, causing membrane depolarization and cell excitability. In mammals, seven P2X receptor subtypes are widely expressed in vascular smooth muscles, platelets, peripheral and central nervous systems and immune cells and mediate various physiological processes including synaptic transmission, synaptic pre-regulation, smooth muscle contraction, cell proliferation and cell death, visceral motility, platelet aggregation, taste, pain, and inflammation. Recent studies on X-ray crystal structures of the zebrafish P2X4 receptor have revealed a common topology of P2X receptors, which include two transmembrane domains (TM1 and TM2), an ATP binding site, and large glycosylated and cysteine-rich extracellular loops containing intracellular N- and C-terminus. It is also known that the gating mechanism when ATP binds to the zP2X4 receptor is determined by a conformational change between the apo and open states of the crystal structure.

Among the P2X receptor subtypes, the P2X3 receptor (P2X3R) is present as a homomeric P2X3 and heteromeric P2X2/3 receptor in small or medium diameter C- and Aδ-fibers primary afferent neurons, which provide a high degree of specificity to the pain-sensing system. Many studies, including knock-out animal studies, have shown that P2X3R is closely related to pain sensation. For example, administration of ATP or αβ-methylene ATP, an P2X3R-selective agonist, to the hind paw of rats induced pain, and in contrast, pain-related behaviors were significantly reduced in neuropathic or inflammatory pain animal models, when P2X3R was knocked-out, or a P2X3R selective antisense RNA or siRNA (short interfering RNA) was used. In addition, the pivotal role of P2X3R in pain sensation was examined using TNP-ATP (2',3'-O-(2,4,6-trinitrophenyl)adenosine-5'-triphosphate), a P2X3 receptor antagonist, and PPADS, and as a result, the pain reaction was reduced in chronic neuropathic pain animal models. Thus, these data suggest that the antagonistic action of P2X3R may be one of the potential therapeutic strategies for the management of chronic pain.

Over the last decade, potent and selective P2X3 receptor antagonists have been developed by the pharmaceutical industry and academic institutions, including the present inventors (FIG. 1a, FIG. 1b, FIG. 1c, FIG. 1d, FIG. 1e, FIG. 1f, FIG. 1g). Abbott Laboratories have disclosed A-317491 (Compound 1 of FIG. 1a), which is the first selective non-nucleotide dual P2X3-P2X2/3 antagonist that exhibits the effect of pain reduction in chronic and inflammatory pain animal models. Roche has reported RO-4 (Compound 2a of FIG. 1b), RO-51 (Compound 2b of FIG. 1b), and RO-85 (Compound 3 of FIG. 1c), which are diaminopyrimidine-based analogs, as the first allosteric antagonists with high efficacy and selectivity for P2X3-P2X2/3 receptors. AstraZeneca has conducted research on the structure-activity relationship (SAR) of the pyrrolo-pyrimidinone derivative (Compound 4 of FIG. 1d) to improve the efficacy and physicochemical properties of P2X3 receptor antagonists. AF-219, a potent, orally biocompatible and selective P2X3-P2X2/3 receptor antagonist, is a clinical drug candidate from Afferent Pharmaceuticals, which showed significant pharmacological effects in phase II clinical trials involving interstitial cystitis/bladder pain syndrome and chronic cough, as a result of proof-of-concept studies. The present inventors have reported Spinorphin (Compound 5 of FIG. 1e, $IC_{50}$=8.3 pM) and 5-hydroxy pyridine derivatives (Compounds 7a-c of FIG. 1g), which are selective and non-economical peptide antagonists, and these compounds have been developed by modifying strong anionic phosphate sulfonic acid groups and instable azo bonds (—N=N—) of PPAD (Compound 6a in FIG. 1f), a nonselective P2X antagonist, with weak anionic carboxylic acids and stable carbon-carbon bonds, respectively.

The present inventors introduced various substituents to carbon at various positions in order to optimize the drug properties of 5-hydroxy pyridine derivatives (Compounds 7a-c of FIG. 1g), and as a result, they have developed a novel hP2X3 receptor antagonist having higher biological stability and superior antagonistic activity.

A number of papers and patent documents have been referred to and their citations are indicated throughout the present specification. The content of the cited papers and patent documents is incorporated herein by reference in their entirety, and the level of technical field to which the present invention belongs and the contents of the present invention will be described more clearly.

DISCLOSURE

Technical Problem

The present inventors have made intensive efforts to develop novel antagonists for P2X1 and P2X3 receptors that play an important role in pain and inflammatory signaling. In this regard, the present inventors synthesized novel compounds having various substituents introduced on the carbon at various positions of 5-hydroxypyridine derivatives (Compounds 7a-c of FIG. 1g) and examined their pharmacokinetics and efficacy, and as a result, they have identified the novel compounds as hP2X3 receptor antagonists having higher biological stability and superior antagonist activity, thereby completing the present invention.

Accordingly, it is one object of the present invention to provide novel 5-hydroxy pyridine-based compounds used as P2X1 and P2X3 receptor antagonists, and pharmaceutical compositions including the same.

It is another object of the present invention to provide a method for treating chronic inflammatory diseases, neuropathic pain diseases or platelet aggregation-related diseases, including administering a pharmaceutical composition including the aforementioned novel 5-hydroxy pyridine-based compounds used as P2X1 and P2X3 receptor antagonists to a subject.

Other aspects and advantages of the present invention will become apparent from the following detailed description together with the appended claims and drawings.

Technical Solution

In one aspect of the present invention, there is provided a compound represented by General Formula 1 below, an isomer thereof, or a pharmaceutically acceptable salt thereof:

[General Formula 1]

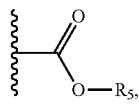

in the General Formula 1,

A is any one of substituents represented by Chemical Formula 1 or 2 below,

[Chemical Formula 1]

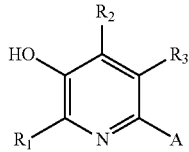

[Chemical Formula 2]

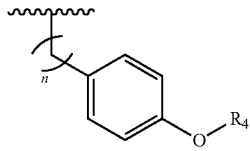

wherein n and m are each independently an integer from 0 to 5;

$R_1$ is a hydrogen atom, a straight or branched $C_1$-$C_6$ alkyl unsubstituted or substituted with carboxyl, sulfonyl, thioether (e.g., —$CH_2CH_2SCH_3$), benzyl, phenethyl;

$R_2$ is a hydrogen atom, a straight or branched $C_1$-$C_6$ alkyl unsubstituted or substituted with carboxyl, sulfonyl, cyano, amide, tetrazolyl or

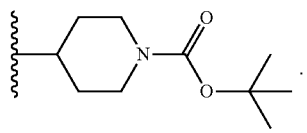 [SMILES: *C1CCN(C(=O)OC(C)(C)C)CC1]

or together with $R_3$ forms a hetero 5- or 6-membered ring including at least one atom selected from the group consisting of N, O, S;

$R_3$ is a hydrogen atom, a straight or branched $C_1$-$C_6$ alkyl unsubstituted or substituted with carboxyl, or together with $R_2$ forms a hetero 5- or 6-membered ring;

$R_4$ is a hydrogen atom or a straight or branched $C_1$-$C_6$ alkyl; and $R_5$ is a straight or branched $C_1$-$C_8$ alkyl unsubstituted or substituted with phenyl, pyrrolidinyl, piperidinyl, tetrahydrofuranyl, or 1,3-dioxo-1,3-dihydro-2H-isoindol-2-yl, $C_5$-$C_6$ cycloalkyl, or

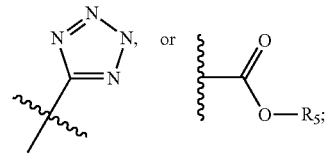

According to one embodiment of the present invention, $R_2$ of General Formula I may be a hydrogen atom, $C_1$-$C_6$ alkyl, —COOH, —CH=CHCOOH, —$CH_2CH_2$COOH, methylsulfonyl (—S(=O)$_2$—$CH_3$), cyano, amide (—$CONH_2$),

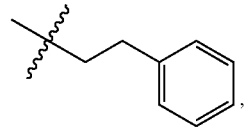

wherein $R_5$ may be

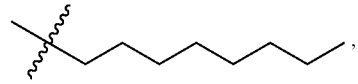

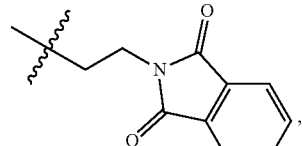

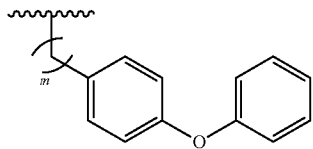

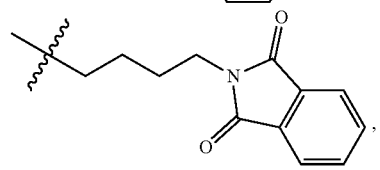

-continued

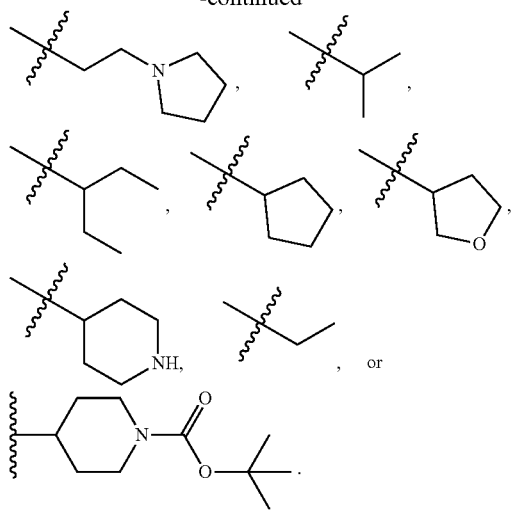

The compound group belonging to the General Formula I, when A of the compound represented by the General Formula I, is the compound of Chemical Formula 1, may include a compound group characterized in that, n is an integer from 0 to 5;

$R_1$ is a hydrogen atom, a straight or branched $C_1$-$C_4$ alkyl unsubstituted or substituted with carboxyl, sulfonyl, thioether (e.g., —$CH_2CH_2SCH_3$), benzyl or phenethyl;

$R_2$ is a hydrogen atom, a straight or branched $C_1$-$C_3$ alkyl unsubstituted or substituted with carboxyl, sulfonyl, cyano, amide, tetrazolyl or

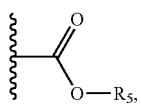

or together with $R_3$ forms a hetero 5- or 6-membered ring including at least one atom selected from the group consisting of N, O, S;

$R_3$ is a hydrogen atom, a straight or branched $C_1$-$C_3$ alkyl unsubstituted or substituted with carboxyl, or together with $R_2$ forms a hetero 5- or 6-membered ring; and $R_4$ is a hydrogen atom or a straight or branched $C_1$-$C_3$ alkyl.

Further, the compound group belonging to the General Formula I, when A of the compound represented by the General Formula I, is the compound of Chemical Formula 2, may include a compound group characterized in that, m is an integer from 0 to 5;

$R_1$ is a hydrogen atom, or a straight or branched $C_1$-$C_3$ alky;

$R_2$ is a hydrogen atom, a straight or branched $C_1$-$C_3$ alkyl unsubstituted or substituted with carboxyl, —$CH_2NH_2$, —$CH_2NH$—$S(=O)_2$—$CH_3$, cyano, or

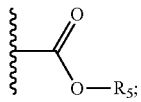

$R_3$ is a hydrogen atom, a straight or branched $C_1$-$C_3$ alkyl unsubstituted or substituted with carboxyl; and $R_5$ is

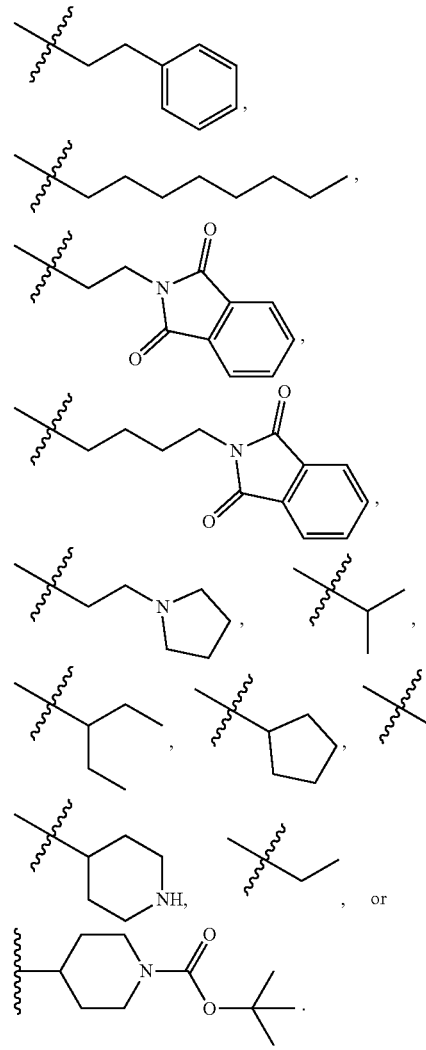

In addition, according to one embodiment of the present invention, there is provided a 5-hydroxy pyridine-based compound represented by General Formula Ia below, an isomer thereof, or a pharmaceutically acceptable salt thereof:

[General Formula Ia]

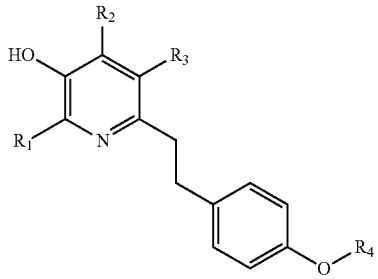

in the General Formula Ia, $R_1$ is a hydrogen atom, a straight or branched $C_1$-$C_4$ alky, carboxyl (—COOH), methylsulfonyl ethyl (—$CH_2CH_2$—$S(=O)_2$—$CH_3$), —$CH_2CH_2SCH_3$, benzyl, or phenethyl;

$R_2$ is a hydrogen atom, $C_1$-$C_3$ alkyl, —COOH, —CH=CHCOOH, —CH$_2$CH$_2$COOH, methylsulfonyl (—S(=O)$_2$—CH$_3$), cyano, amide (—CONH$_2$), or

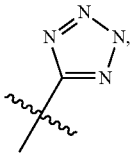

together with $R_3$ forms a hetero 5- or 6-membered ring including at least one atom selected from the group consisting of N, O, S;

$R_3$ is a hydrogen atom, $C_1$-$C_3$ alkyl or carboxyl, or together with $R_2$ forms a hetero 5- or 6-membered ring; and $R_4$ is a hydrogen atom or $C_1$-$C_3$ alkyl.

Further, according to another embodiment of the present invention, there is provided a 5-hydroxy pyridine-based compound represented by General Formula Ib below, an isomer thereof, or a pharmaceutically acceptable salt thereof:

[General Formula Ib]

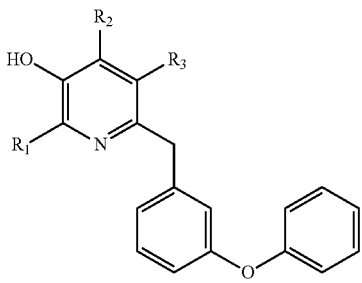

in the General Formula Ib, $R_1$ is a hydrogen atom, or a straight or branched $C_1$-$C_3$ alky;

$R_2$ is a hydrogen atom, a straight or branched $C_1$-$C_3$ alkyl, —COOH, —CH=CHCOOH, —CH$_2$CH$_2$COOH, —CH$_2$NH$_2$, sulfonyl (—CH$_2$NH—S(=O)$_2$—CH$_3$), cyano, or

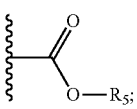

$R_3$ is a hydrogen atom, a straight or branched $C_1$-$C_3$ alkyl, or carboxyl (—COOH); and $R_5$ is

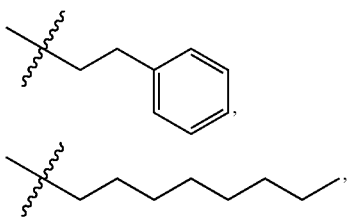

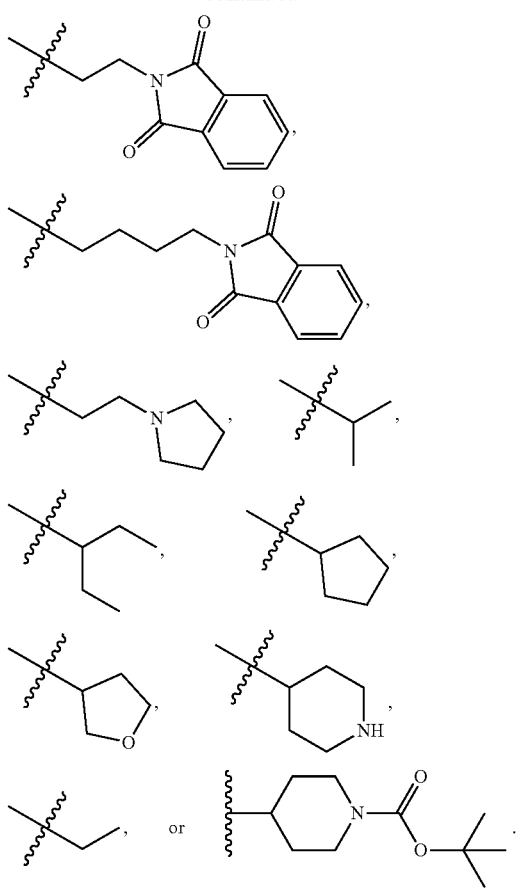

Furthermore, according to still another embodiment of the present invention, there is provided a 5-hydroxy pyridine-based compound represented by General Formula Ib' below, an isomer thereof, or a pharmaceutically acceptable salt thereof:

[General Formula Ib']

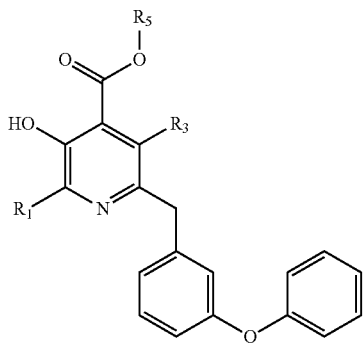

in the General Formula Ib', $R_1$ is a hydrogen atom, or a straight or branched $C_1$-$C_3$ alky;

$R_3$ is a hydrogen atom, or a straight or branched $C_1$-$C_3$ alkyl; and $R_5$ is

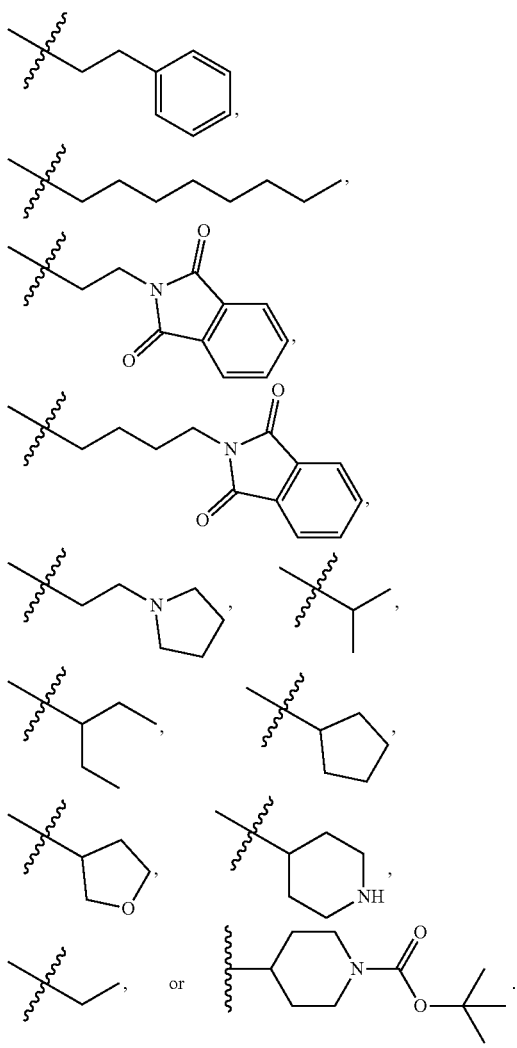

The compounds belonging to the General Formula Ia may include 5-Hydroxy-2-(4-methoxyphenethyl)pyridine-3,4-dicarboxylic acid (13a); 5-Hydroxy-2-(4-methoxyphenethyl)-6-methylpyridine-3,4-dicarboxylic acid (13b); 6-Ethyl-5-hydroxy-2-(4-methoxyphenethyl)pyridine-3,4-dicarboxylic acid (13c); 5-Hydroxy-2-(4-methoxyphenethyl)-6-propylpyridine-3,4-dicarboxylic acid (13d); 6-Butyl-5-hydroxy-2-(4-methoxyphenethyl)pyridine-3,4-dicarboxylic acid (13e); 5-Hydroxy-6-isopropyl-2-(4-methoxyphenethyl)pyridine-3,4-dicarboxylic acid (13f); 5-Hydroxy-6-isobutyl-2-(4-methoxyphenethyl)pyridine-3,4-dicarboxylic acid (13g); 6-Benzyl-5-hydroxy-2-(4-methoxyphenethyl)pyridine-3,4-dicarboxylic acid (13h); 5-Hydroxy-2-(4-methoxyphenethyl)-6-phenethylpyridine-3,4-dicarboxylic acid (13i); 3-Hydroxy-6-(4-methoxyphenethyl)pyridine-2,4,5-tricarboxylic acid (13j); 5-Hydroxy-2-(4-methoxyphenethyl)-6-(2-(methylthio)ethyl)pyridine-3,4-dicarboxylic acid (13k); 5-Hydroxy-2-(4-methoxyphenethyl)-6-(2-(methylsulfonyl)ethyl)pyridine-3,4-dicarboxylic acid (13l); Ethyl 4-cyano-5-hydroxy-2-(4-methoxyphenethyl)-6-methylnicotinate (14); Ethyl 5-hydroxy-2-(4-methoxyphenethyl)-6-methyl-4-(1H-tetrazol-5-yl)nicotinate (15); 4-Cyano-5-hydroxy-2-(4-methoxyphenethyl)-6-methylnicotinic acid (16); 5-Hydroxy-2-(4-methoxyphenethyl)-6-methyl-4-(1H-tetrazol-5-yl)nicotinic acid (17); 7-Hydroxy-4-(4-methoxyphenethyl)-6-methylfuro[3,4-c]pyridine-1,3-dione (18); 8-Hydroxy-5-(4-methoxyphenethyl)-7-methyl-2,3-dihydropyrido[3,4-d]pyridazine-1,4-dione (19); 6-(4-Methoxyphenethyl)-2-methyl-4-(methylsulfonyl)pyridin-3-ol (20); Methyl 3-hydroxy-6-(4-methoxyphenethyl)-2-methylisonicotinate (21a); Methyl 3-hydroxy-6-(4-methoxyphenethyl)-2,5-dimethylisonicotinate (21b); Methyl 3-hydroxy-6-(4-methoxyphenethyl)-5-methyl-2-propylisonicotinate (21c); 3-Hydroxy-6-(4-methoxyphenethyl)-2-methylisonicotinic acid (22a); 3-Hydroxy-6-(4-methoxyphenethyl)-2,5-dimethylisonicotinic acid (22b); 3-Hydroxy-6-(4-methoxyphenethyl)-5-methyl-2-propylisonicotinic acid (22c); and 5-Hydroxy-2-[2-(4-methoxyphenyl)ethyl]-3-methyl-6-propyl-pyridine-4-carboxamide (23).

The compounds belonging to the General Formula Ib or Ib' may include Dimethyl 5-hydroxy-2-(3-phenoxybenzyl)-6-propylpyridine-3,4-dicarboxylate (26); 5-Hydroxy-2-(3-phenoxybenzyl)-6-propylpyridine-3,4-dicarboxylic acid (27); Methyl 3-hydroxy-5-methyl-6-(3-phenoxybenzyl)-2-propylisonicotinate (28); 3-Hydroxy-5-methyl-6-(3-phenoxybenzyl)-2-propylisonicotinic acid (29); Methyl 3-(benzyloxy)-5-methyl-6-(3-phenoxybenzyl)-2-propylisonicotinate (30); (3-(Benzyloxy)-5-methyl-6-(3-phenoxybenzyl)-2-propylpyridin-4-yl)methanol (31); 4-(Hydroxymethyl)-5-methyl-6-(3-phenoxybenzyl)-2-propylpyridin-3-ol (32); 3-Hydroxy-5-methyl-6-(3-phenoxybenzyl)-2-propylisonicotinaldehyde (33); Ethyl (E)-3-(3-hydroxy-5-methyl-6-(3-phenoxybenzyl)-2-propylpyridin-4-yl)acrylate (34); (E)-3-(3-Hydroxy-5-methyl-6-(3-phenoxybenzyl)-2-propylpyridin-4-yl)acrylic acid (35); Ethyl 3-(3-hydroxy-5-methyl-6-(3-phenoxybenzyl)-2-propylpyridin-4-yl)propanoate (36); 3-(3-Hydroxy-5-methyl-6-(3-phenoxybenzyl)-2-propylpyridin-4-yl)propanoic acid (37) 3-Hydroxy-5-methyl-6-(3-phenoxybenzyl)-2-propylisonicotinonitrile (38); 3-(Benzyloxy)-5-methyl-6-(3-phenoxybenzyl)-2-propylisonicotinonitrile (39); (3-(Cyclohexa-2,4-dien-1-ylmethoxy)-5-methyl-6-(3-phenoxybenzyl)-2-propylpyridin-4-yl)methanamine (40); 4-(Aminomethyl)-5-methyl-6-(3-phenoxybenzyl)-2-propylpyridin-3-ol (41); N-((3-(Benzyloxy)-5-methyl-6-(3-phenoxybenzyl)-2-propylpyridin-4-yl)methyl)methanesulfonamide (42); N-((3-Hydroxy-5-methyl-6-(3-phenoxybenzyl)-2-propylpyridin-4-yl)methyl)methanesulfonamide (43); Phenethyl 3-hydroxy-5-methyl-6-(3-phenoxybenzyl)-2-propylisonicotinate (46a); Octyl 3-hydroxy-5-methyl-6-(3-phenoxybenzyl)-2-propylisonicotinate (46b); 2-phthalimidoethyl 3-hydroxy-5-methyl-6-(3-phenoxybenzyl)-2-propylisonicotinate (46c); 4-phthalimidobutyl 3-hydroxy-5-methyl-6-(3-phenoxybenzyl)-2-propylisonicotinate (46d); 2-(pyrrolidin-1-yl)ethyl 3-hydroxy-5-methyl-6-(3-phenoxybenzyl)-2-propylisonicotinate (46e); Isopropyl 3-hydroxy-5-methyl-6-(3-phenoxybenzyl)-2-propylisonicotinate (46f); Pentan-3-yl 3-hydroxy-5-methyl-6-(3-phenoxybenzyl)-2-propylisonicotinate (46g); Cyclopentyl 3-hydroxy-5-methyl-6-(3-phenoxybenzyl)-2-propylisonicotinate (46h); Tetrahydrofuran-3-yl 3-hydroxy-5-methyl-6-(3-phenoxybenzyl)-2-propylisonicotinate (46i); 1-(Tert-butoxycarbonyl)piperidin-4-yl 3-hydroxy-5-methyl-6-(3-phenoxybenzyl)-2-propylisonicotinate (46j); Piperidin-4-yl 3-hydroxy-5-methyl-6-(3-phenoxybenzyl)-2-propylisonicotinate (47); and Ethyl 3-hydroxy-5-methyl-6-(3-phenoxybenzyl)-2-propylisonicotinate (48).

The compounds represented by General Formula 1 according to the present invention may be prepared into pharmaceutically acceptable salts or solvates using typical methods known in the art.

An acid addition salt formed by a pharmaceutically acceptable free acid may be useful as the salt. The acid addition salt may be prepared by a conventional method, for example, by dissolving the compound in an excessive amount of acid aqueous solution, and then precipitating the salt using a water-miscible organic solvent such as methanol, ethanol, acetone or acetonitrile. An acid or alcohol (e.g., glycol monomethyl ether) in the equal molar amount of the compound and water may be heated, and then the mixture may be dried by evaporation, or the precipitated salt may be suction-filtered.

Herein, as the free acid, an organic acid and an inorganic acid may be used. As the inorganic acid, hydrochloric acid, phosphoric acid, sulfuric acid, nitric acid, tartaric acid, etc. may be used, and as the organic acid, methanesulfonic acid, p-toluenesulfonic acid, acetic acid, trifluoroacetic acid, citric acid, maleic acid, succinic acid, oxalic acid, benzoic acid, tartaric acid, fumaric acid, mandelic acid, propionic acid, lactic acid, glycolic acid, gluconic acid, galacturonic acid, glutamic acid, glutaric acid, glucuronic acid, aspartic acid, ascorbic acid, carbonic acid, vanillic acid, hydroiodic acid, etc. may be used.

Further, a pharmaceutically acceptable metal salt may be prepared using a base. An alkali metal salt or an alkaline earth metal salt is obtained, for example, by dissolving a compound in an excessive amount of an alkali metal hydroxide or an alkaline earth metal hydroxide solution, filtering undissolved compound salts, and then evaporating and drying the filtrate. Herein, it is preferable that a sodium, potassium or calcium salt is prepared as the metal salt in a pharmaceutical aspect. Also, a silver salt corresponding to the metal salt may be obtained by allowing an alkali metal salt or an alkaline earth metal salt to react with a suitable silver salt (e.g. silver nitrate).

The pharmaceutically acceptable salt of the 5-hydroxy pyridine-based compounds having the structure of General Formula I may include a salt of an acidic or a basic group, which can be present in the 5-hydroxy pyridine-based compounds having the structure of General Formula I, unless otherwise specifically indicated. For example, the pharmaceutically acceptable salt may include a sodium salt, a calcium salt, and a potassium salt of a hydroxy group, and other pharmaceutically acceptable salt of amino group may include hydrobromide, sulfate, hydrogen sulfate, phosphate, hydrogen phosphate, dihydrogen phosphate, acetate, succinate, citrate, tartrate, lactate, mandelate, methanesulfonate (mesylate), p-toluenesulfonate (tosylate), etc. and these salts may be prepared by a preparation method or preparation process known in the art.

Furthermore, the 5-hydroxy pyridine-based compounds having the structure of General Formula I has an asymmetric center and thus may be present in the form of different enantiomers, and all optical isomers and R or S stereoisomers of the 5-hydroxy pyridine-based compounds having the structure of General Formula I, and mixtures thereof fall within the scope of the present invention. The present invention includes the use of racemates, one or more enantiomers, one or more diastereomers or mixtures thereof, and also includes separation methods or preparation processes of isomers known in the art.

In another aspect of the present invention, there is provided a method for preparing the compound of General Formula I, and the compound may be chemically synthesized by the method shown in Reaction Schemes below, but is not limited to these examples.

The following Reaction Schemes illustrate a step-by-step preparation method of the representative compounds of the present invention, and various compounds of the present invention may be prepared by small modifications such as modifying the reagents, solvents, and reaction sequences used in the synthesis of Reaction Schemes 1 to 8.

Some compounds of the present invention have been synthesized according to the procedures not disclosed in the scope of the Reaction Schemes, and the detailed synthesis procedures for these compounds are described in their respective Examples.

(Reaction Scheme 1) Preparation of
3,4-Dicarboxypyridine derivatives

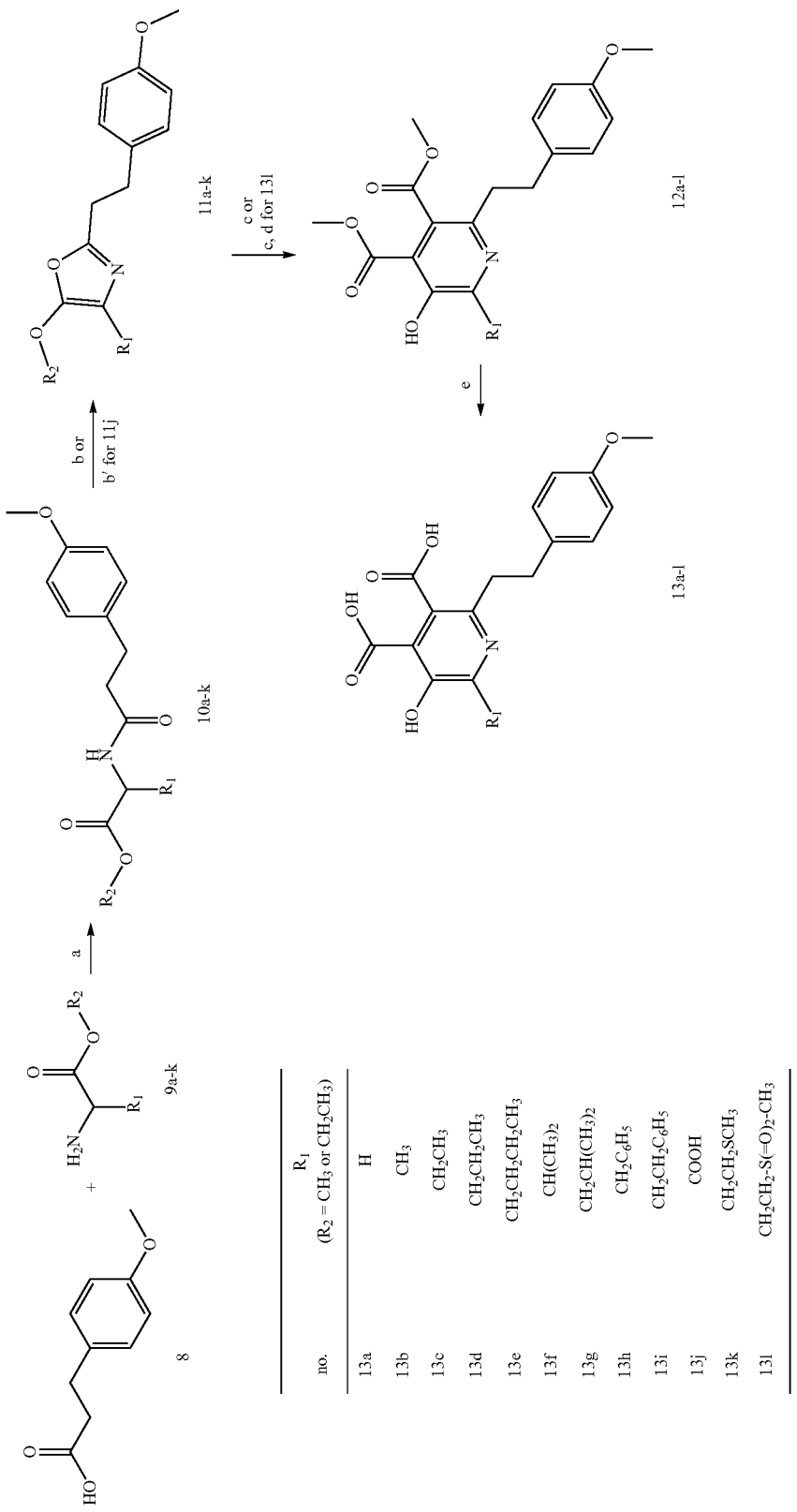

Reagents and Conditions for Reaction Scheme 1: (a) EDC, TEA, DCM, RT, 2 h, 55-99%; (b) P₂O₅, CHCl₃, reflux, 5 h, 58-99%; (b') triphenylphosphine, iodine, TEA, DCM, RT, 12 h, 50-63%; (c)dimethylmaleate, neat, reflux, 5 h, 21-52%; (d) Oxone®, MeOH/THF=3:1, RT, 4 h, 63-88%; (e) 20% KOH (aq), RT, 6 h, 35-90%.
(Reaction Scheme 2) Preparation of 5-Hydroxypyridine Derivatives (Compounds 16-19)
<Reaction Scheme 2-1>
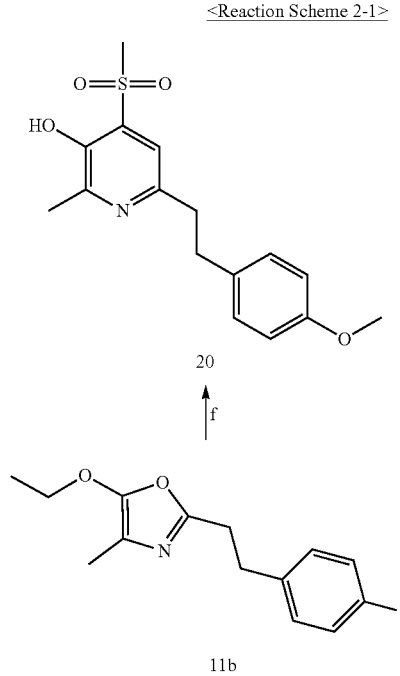
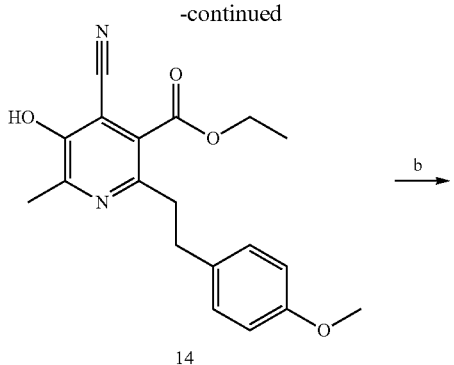
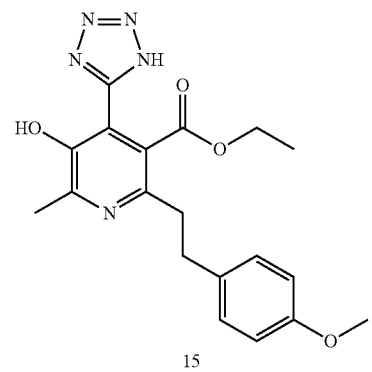
<Reaction Scheme 2-2>
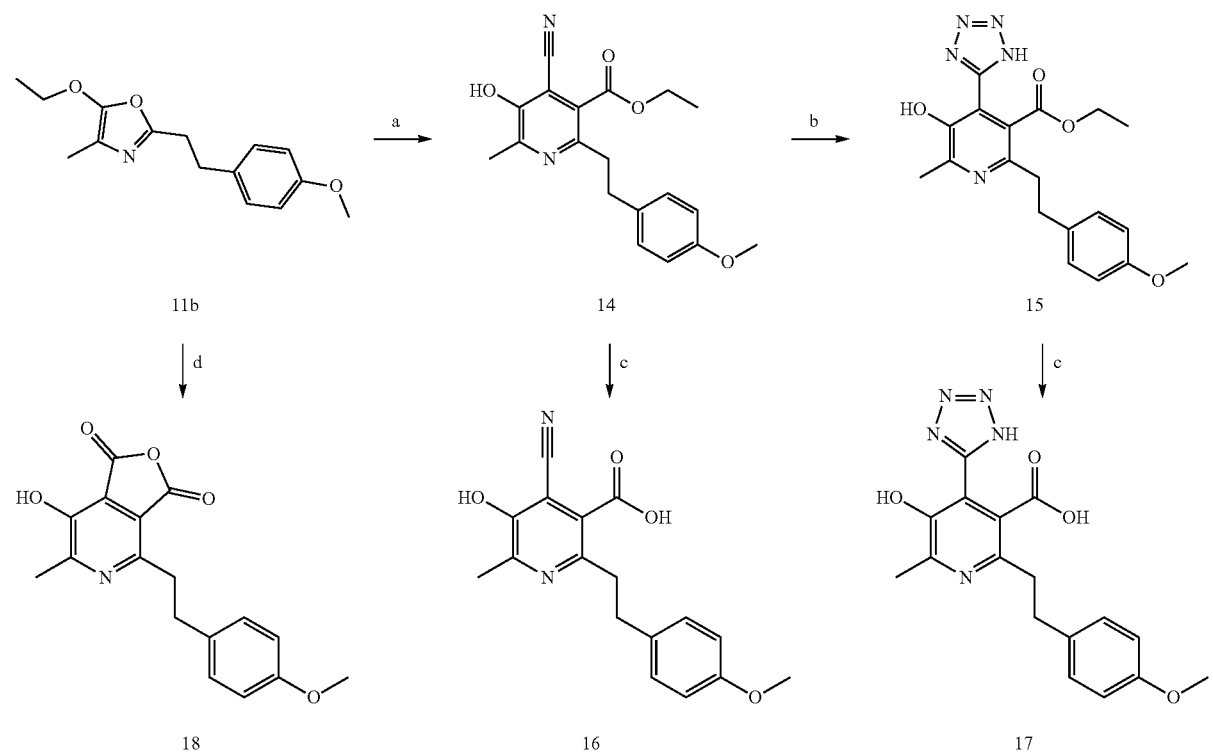

<Reaction Scheme 2-3>

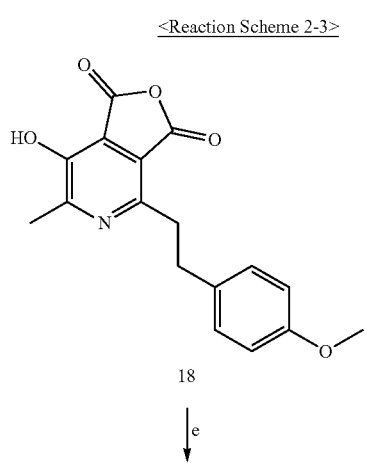

18

↓e

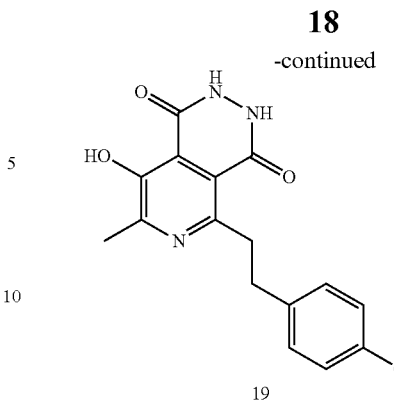

19

Reagents and Conditions for Reaction Scheme 2 (2-1 to 2-3): (a) cis-beta cyanoacrylate, neat, reflux, 5 h, 27-55%; (b) sodium azide, ammonium chloride, DMF, 90° C., 12 h, 48-62%; (c) 20% KOH (aq), RT, 6 h, 30-52%; (d) maleic anhydride, benzene, 60° C., 2 h, 43-54%; (e) hydrazine hydrate (aq), sodium acetate anhydrous, acetic acid, reflux, 2 h, 35-46%; (f) methyl vinyl sulfone, neat, reflux, 5 h, 49-55%.

(Reaction Scheme 3) Preparation of 5-Hydroxypyridine Derivatives (Compounds 21-23)

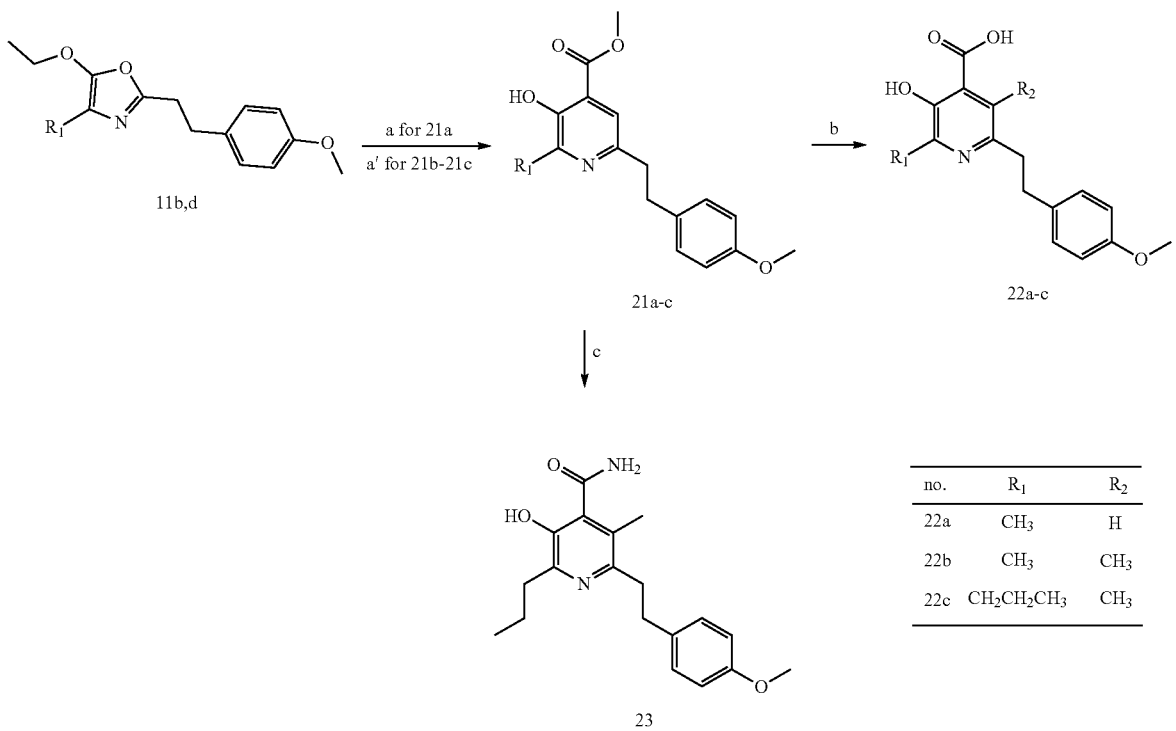

| no. | $R_1$ | $R_2$ |
|---|---|---|
| 22a | $CH_3$ | H |
| 22b | $CH_3$ | $CH_3$ |
| 22c | $CH_2CH_2CH_3$ | $CH_3$ |

Reagents and Conditions for Reaction Scheme 3: (a) methyl acrylate, neat, 5 h, 37-46%; (a') methyl crotonate, neat, 5 h, 32-52%; (b) 20% KOH (aq), RT, 6 h, 40-57%; (c) 30% ammonia (aq), RT, 12 h, 32-45%.

(Reaction Scheme 4) Preparation of 5-Hydroxypyridine Derivatives (Compounds 26-29, 33-37)
<Reaction Scheme 4-1>
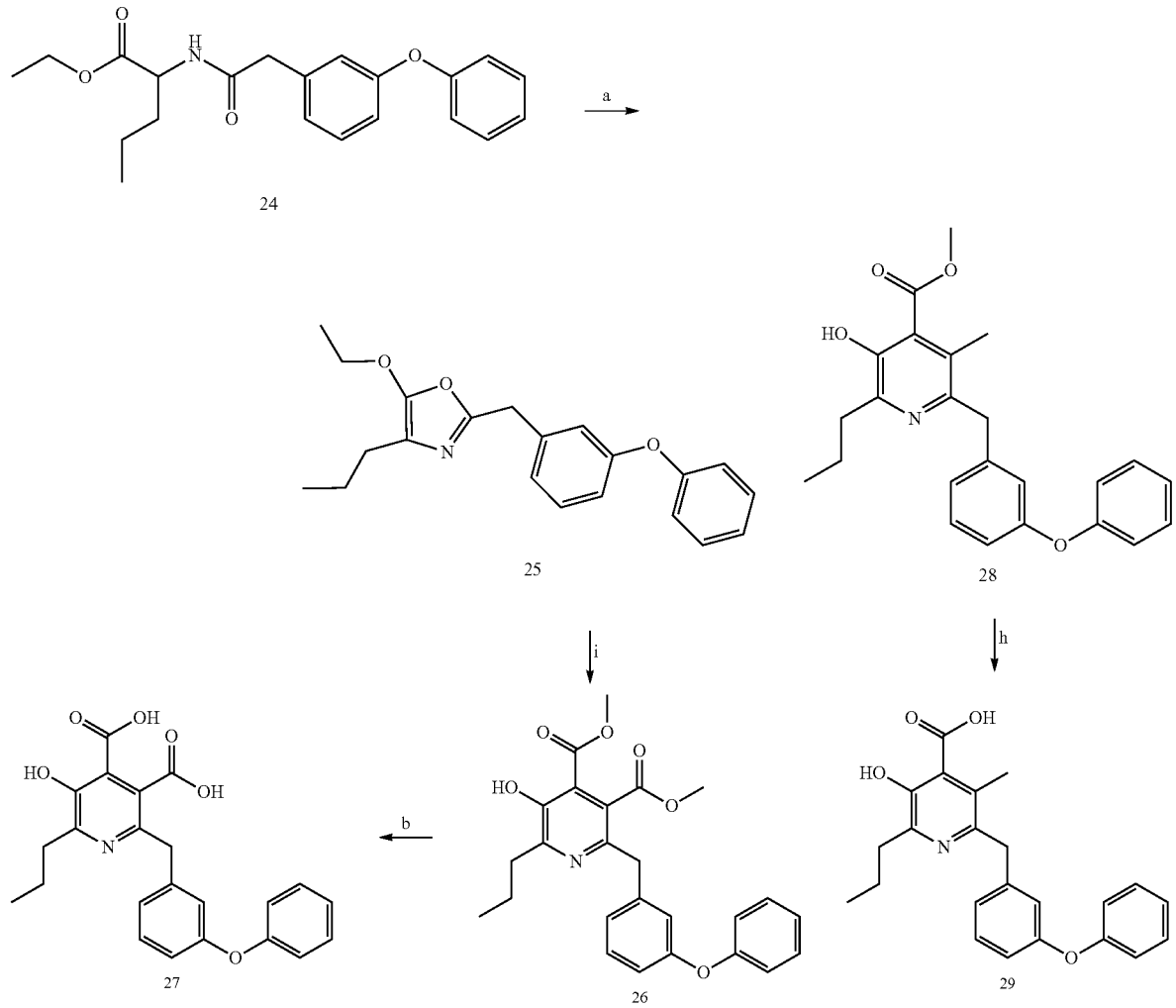
Reaction Scheme 4-2
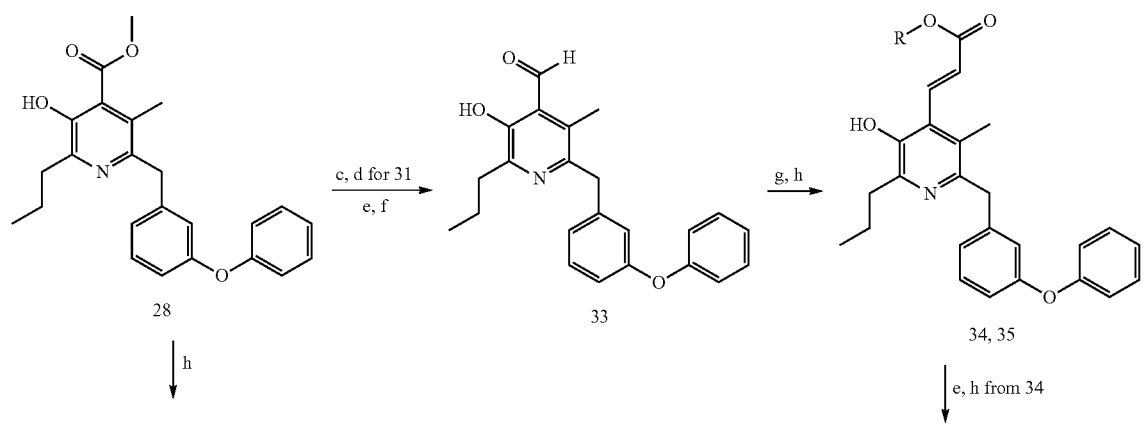

21

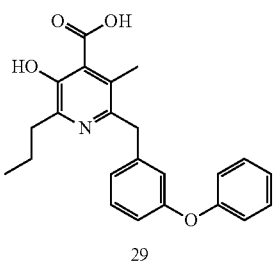

29

22

-continued

| no. | R |
|---|---|
| 34 | CH$_2$CH$_3$ |
| 35 | CH$_3$ |
| 36 | CH$_2$CH$_3$ |
| 37 | H |

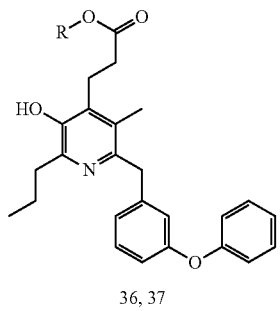

36, 37

Reagents and Conditions for Reaction Scheme 4: (a) P$_2$O$_5$, CHCl$_3$, reflux, 5 h, 85-99%; (b) methyl crotonate, neat, reflux, 5 h, 22-52%; (c) benzyl bromide, K$_2$CO$_3$, acetone, reflux, 2 h, 73-96%; (d) LAH, ether, 0° C., 1 h, 67-88%; (e) Pd/C, H$_2$, RT, 0.5 h, 54-91%; (f) MnO$_2$, DCM, RT, 2 h, 66-85%; (g) NaH, triethylphosphonoacetate, THF, RT, 1 h, 63-78%; (h) 20% KOH(aq), RT, 6 h, 37-94%; (i) dimethyl maleate, neat, reflux, 5 h, 32-54%.

(Reaction Scheme 5) Preparation of 5-Hydroxypyridine Derivatives (Compounds 38-43)

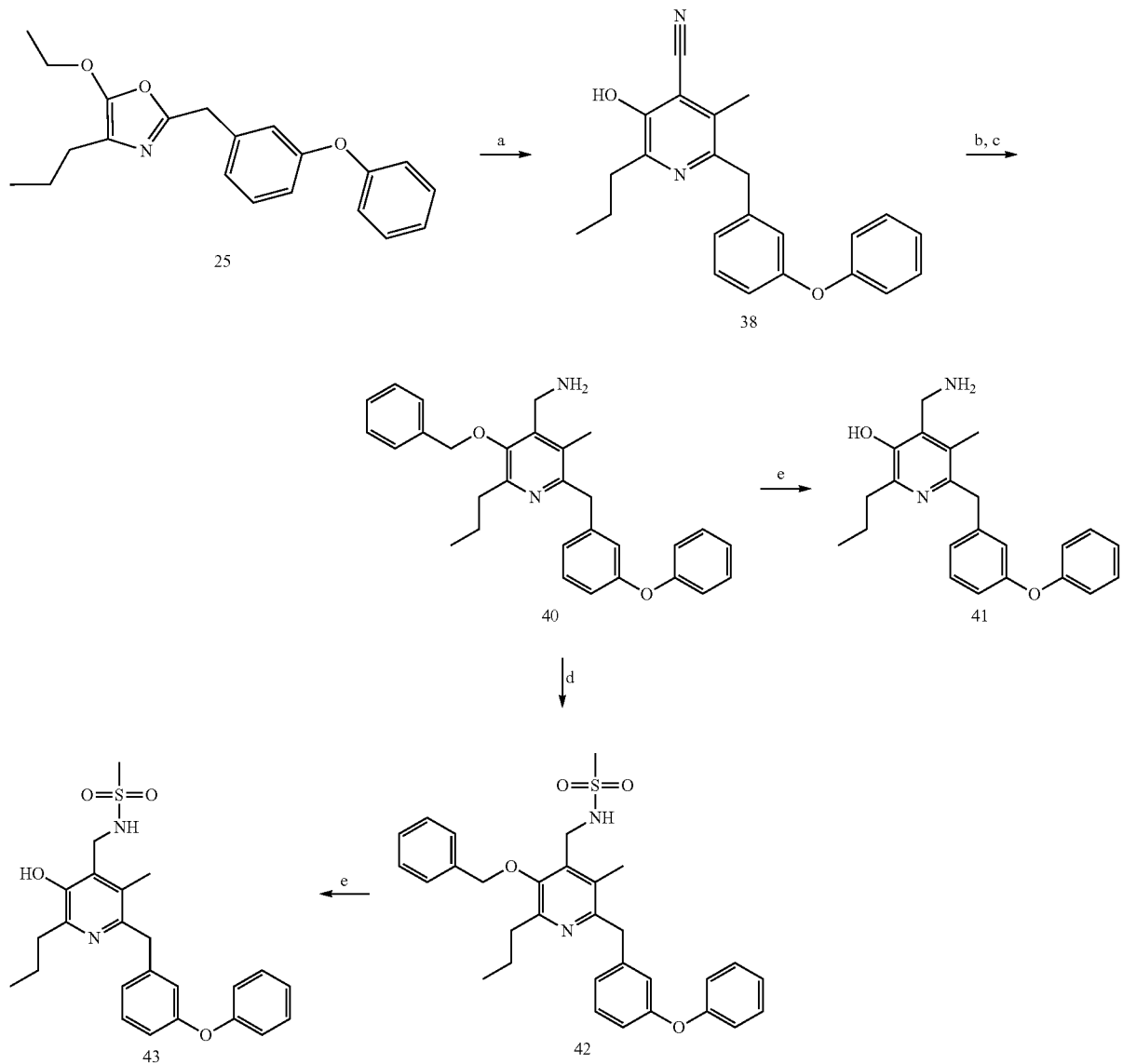

Reagents and Conditions for Reaction Scheme 5: (a) methyl crotononitrile, neat, reflux, 5 h, 52-74%; (b) benzyl bromide, $K_2CO_3$, acetone, reflux, 2 h, 62-86%; (c) LAH, ether, 0° C., 1 h, 52-74%; (d) methanesulfonyl chloride, TEA, DCM, RT, 1 h, 61-77%; (e) Pd/C, $H_2$, RT, 0.5 h, 60-91%.

(Reaction Scheme 6) Preparation of Compounds 46a-i

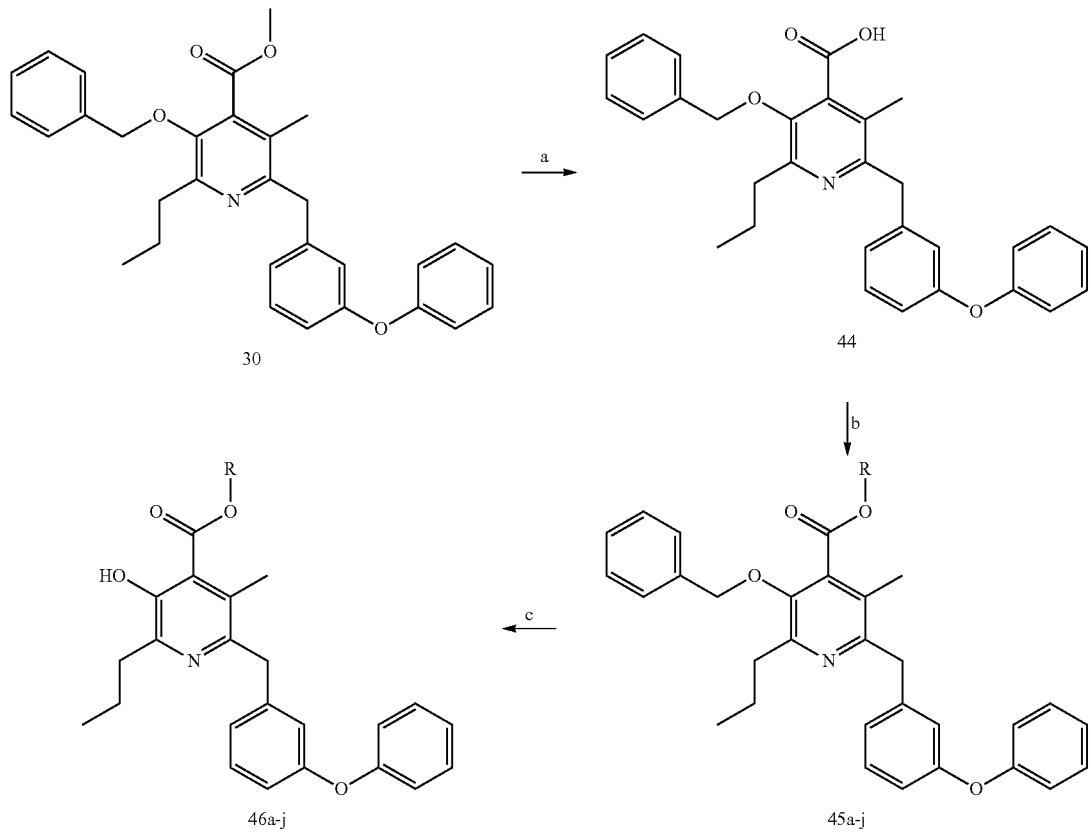

Reagents and Conditions for Reaction Scheme 6: (a) 20% KOH, methanol, 1,4-dioxane, 50° C., 2 d, 63%; (b) alkyl bromide, $NaHCO_3$, DMF, 60° C., 5 h, 35-89%; (c) Pd/C, $H_2$ (1 atm), DCM, methanol, RT, 30 min, 22-89%.

The substituents R of Compounds 45a-j and Compounds 46a-j are as shown in Table 1 below:

TABLE 1

| Compounds | R |
| --- | --- |
| 45a,46a | (3-phenylpropyl) |
| 45b,46b | (n-nonyl) |
| 45c,46c | (phthalimidopropyl) |
| 45d,46d | (phthalimidobutyl) |

TABLE 1-continued

| Compounds | R |
|---|---|
| 45e,46e | 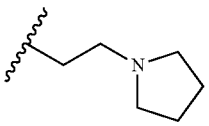 [SMILES: *CCN1CCCC1] |
| 45f,46f | 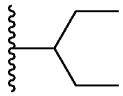 |
| 45g,46g |  |
| 45h,46h | 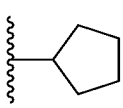 |
| 45i,46i | 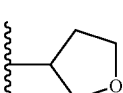 |
| 45j,46j | 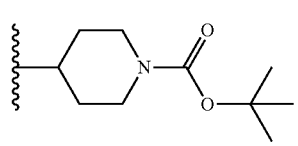 [SMILES: *C1CCN(C(=O)OC(C)(C)C)CC1] |

(Reaction Scheme 7) Preparation of 5-Hydroxypyridine Derivatives (Compound 47)

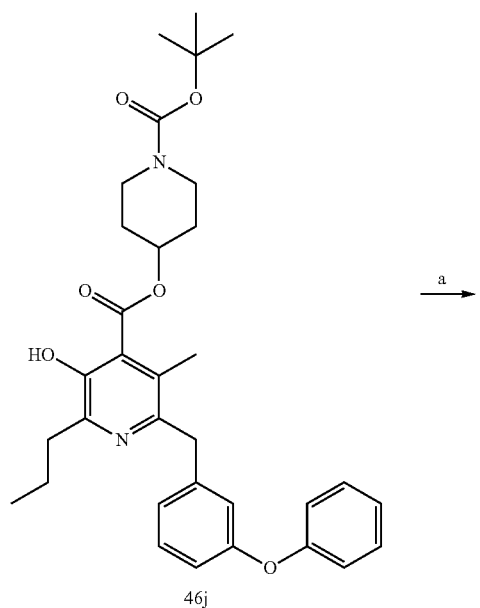

46j a →

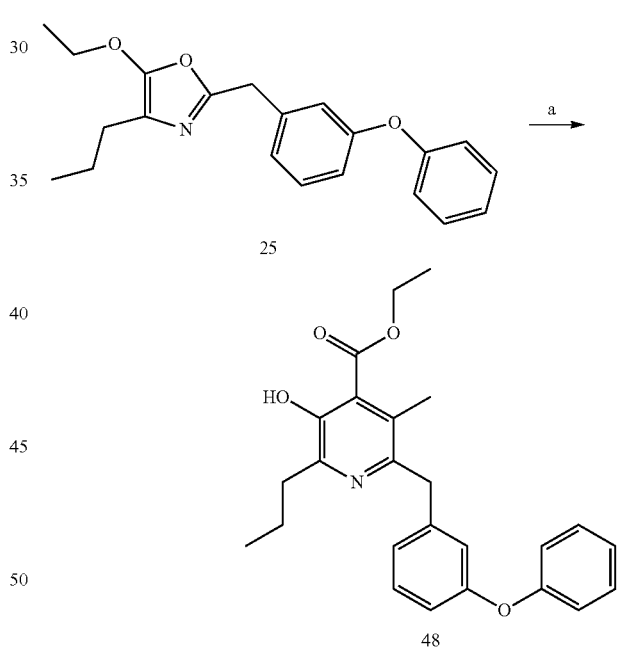

47

Reagents and Conditions for Boc-deprotection of Reaction Scheme 7: 20% TFA, DCM, RT, 1 h, 67%.

(Reaction Scheme 8) Preparation of 5-Hydroxypyridine Derivatives (Compound 48)

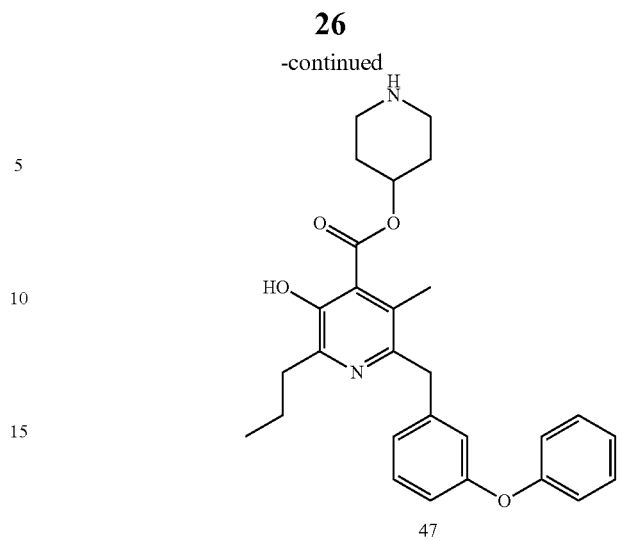

48

Reagents and Conditions for Diels-Alder reaction of Reaction Scheme 8: ethyl crotonate, neat, 5 h, 42%.

Since the compounds represented by the General Formula I of the present invention exhibit a potent antagonistic activity for P2X1 and P2X3 receptors, they may be effectively used as agents capable of preventing or treating diseases caused by P2X1 and P2X3 receptor activity, for example, chronic inflammatory diseases such as degenerative arthritis, rheumatoid arthritis, asthma, chronic obstructive pulmonary disease, or cystitis; neuropathic pain diseases such as neuropathic pain, allodynia, diabetic neuropathy, spontaneous pain, irritable pain, phantom limb pain, or complex regional pain syndrome; or platelet aggregation-related diseases such as arteriosclerosis, stroke, thrombosis, embolism, myocardial infarction, atherosclerosis, or peripheral blood circulation disorder.

Accordingly, the present invention provides a pharmaceutical composition for preventing or treating chronic inflammatory diseases, neuropathic pain diseases or platelet aggregation-related diseases caused by P2X1 and P2X3 receptor activity, including the compound of General Formula 1 as an active ingredient.

As defined herein, the chronic inflammatory diseases caused by P2X1 and P2X3 receptor activity include, for example, degenerative arthritis, rheumatoid arthritis, asthma, chronic obstructive pulmonary disease, or cystitis; the neuropathic pain diseases caused by P2X1 and P2X3 receptor activity include, for example, neuropathic pain, allodynia, diabetic neuropathy, spontaneous pain, irritable pain, phantom limb pain, or complex regional pain syndrome; and the platelet aggregation-related diseases caused by P2X1 and P2X3 receptor activity include, for example, arteriosclerosis, stroke, thrombosis, embolism, myocardial infarction, atherosclerosis, or peripheral blood circulation disorder.

Thus, the present invention provides an antagonist for P2X1 and P2X3 receptors, including a 5-hydroxy pyridine-based compound having the structure of General Formula I as an active ingredient.

The present inventors have found that the novel 5-hydroxypyridine-based compounds exhibit a potent antagonistic activity for P2X1 and P2X3 receptors, which was confirmed by the two-electrode voltage clamp assay (TEVC) in frog eggs (*Xenopus* oocytes) expressing cloned mouse P2X1 and human P2X3 receptors, and by analyzing ethidium bromide accumulation in human HEK293 cells expressing the human P2X7 receptor, it was confirmed that the compounds of the present invention have a high potential to be developed into a drug for treating and preventing chronic inflammatory diseases, neuropathic pain diseases or platelet aggregation-related diseases caused by P2X1 and P2X3 receptor activity, thereby completing the present invention.

In another aspect, the present invention relates to a pharmaceutical composition for preventing or treating diseases caused by P2X1 and P2X3 receptor activity, including a 5-hydroxy pyridine-based compound, and a method for treating the aforementioned diseases using a 5-hydroxy pyridine-based compound.

As used herein, the term "prevention" or "preventing" means all actions that are intended to inhibit or delay the onset of all diseases related to P2X1 and P2X3 receptor activity by administration of the composition including 5-hydroxypyridine-based compounds. Further, as used herein, the term "treatment" or "treating" means all actions that are intended to ameliorate or beneficially change all diseases related to P2X1, P2X3 and P2X7 receptor activity by administration of the pharmaceutical composition.

Compositions and therapeutic methods including the 5-hydroxy pyridine-based compounds of the present invention may be used not only for humans, but also mammal such as cattle, horses, sheep, pigs, goats, camels, antelopes, dogs, cats being at risk of having all diseases related to P2X1 and P2X3 receptor activity.

In addition, the present invention provides a pharmaceutical composition for treating or preventing all diseases related to P2X1 and P2X3 receptor activity, including the 5-hydroxy pyridine-based compounds having the structure of General Formula I as an active ingredient.

The composition including the compound of the present invention may further include a suitable carrier, an excipient or a diluent according to a conventional method known in the art.

The acceptable carrier, excipient or diluent that can be included in the composition of the present invention includes lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, talc, magnesium stearate and mineral oil.

The composition including the compound of the present invention may be used in the form of preparations for oral administration such as powders, granules, tablets, capsules, suspensions, emulsions, syrups, aerosols, etc., external application, suppositories or sterile injectable solution according to a conventional method known in the art.

Specifically, when formulated, the composition of the present invention may be prepared with commonly used diluents or excipients, such as fillers, extenders, binders, wetting agents, disintegrants, surfactants, etc. Examples of solid preparations for oral administration include tablets, pills, powders, granules, capsules, etc., and these solid formulations may be prepared by mixing the compound with at least one excipient, for example, starch, calcium carbonate, sucrose, lactose, gelatin, etc. In addition to simple excipients, lubricants such as magnesium stearate and talc may be used. Liquid preparations for oral administration include suspensions, solutions for internal use, emulsions, syrups, etc. In addition to water commonly used as a simple diluent and liquid paraffin, various excipients, for example, wetting agents, sweetening agents, flavors, preservatives, etc. may be included. Preparations for parenteral administration include sterilized aqueous solutions, non-aqueous solvents, suspending agents, emulsions, freeze-drying agents, and suppositories. Propylene glycol, polyethylene glycol, vegetable oils such as olive oil, injectable esters such as ethyl oleate may be used as non-aqueous solutions and suspending agents. As a base for the suppositories, witepsol, macrogol, tween 61, cacao butter, laurin butter, glycerinated gelatin, etc. may be used.

A preferable dose of the compound of the present invention may depend on the condition and body weight of the patient, the severity of the disease, drug forms, administration routes and duration, but may be appropriately selected by those skilled in the art. However, in order to achieve a preferable effect, the daily dosage of the compound of the present invention may be 0.0001 to 100 mg/kg, preferably 0.001 to 100 mg/kg, and the dosage may be administered once or several times a day. The compound of the present invention may be present in the composition in an amount of 0.0001 to 10% by weight, preferably 0.001 to 1% by weight based on the total weight of the composition.

In addition, as the pharmaceutical administration forms of the compound of the present invention, the composition may also be used in the form of a pharmaceutically acceptable salt thereof, and may be used alone or in combination with other pharmaceutically active compounds as well as in suitable assemblage.

The pharmaceutical composition of the present invention may be administered to mammals such as rats, mice, livestock, and humans by various routes. All modes of administration may be expected, for example, the composition may be administered by oral, rectal or intravenous, intramuscular, subcutaneous, intrauterine, or intracerebroventricular injection.

Advantageous Effects

The present invention provides novel 5-hydroxy pyridine-based compounds useful as P2X1 and P2X3 receptor antagonists and pharmaceutical compositions including the same.

The compounds according to the present invention strongly antagonize P2X1 and P2X3 receptors and thus may be effectively used as a drug for treating and preventing chronic inflammatory diseases or neuropathic pain diseases caused by P2X1 and P2X3 receptor activity.

DETAILED DESCRIPTION OF THE EMBODIMENTS

Figure 1A:
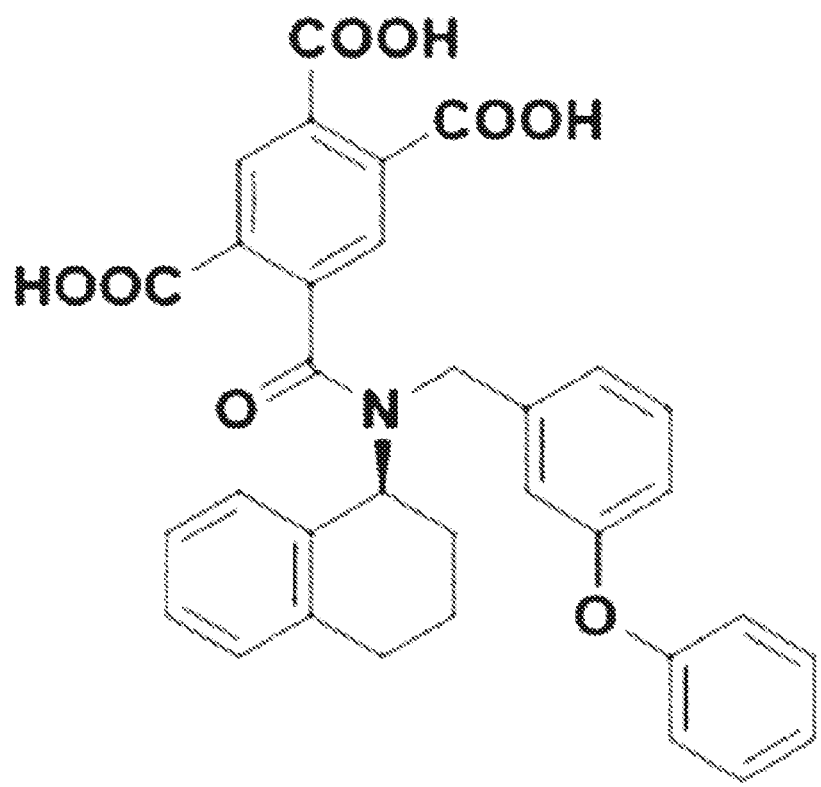
FIGS. 1a to 1g show antagonists for previously developed P2X receptors and P2X receptor antagonists reported by the present inventors.
Figure 1B:
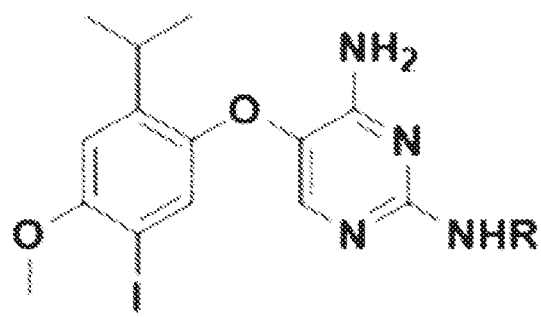
Figure 1C:
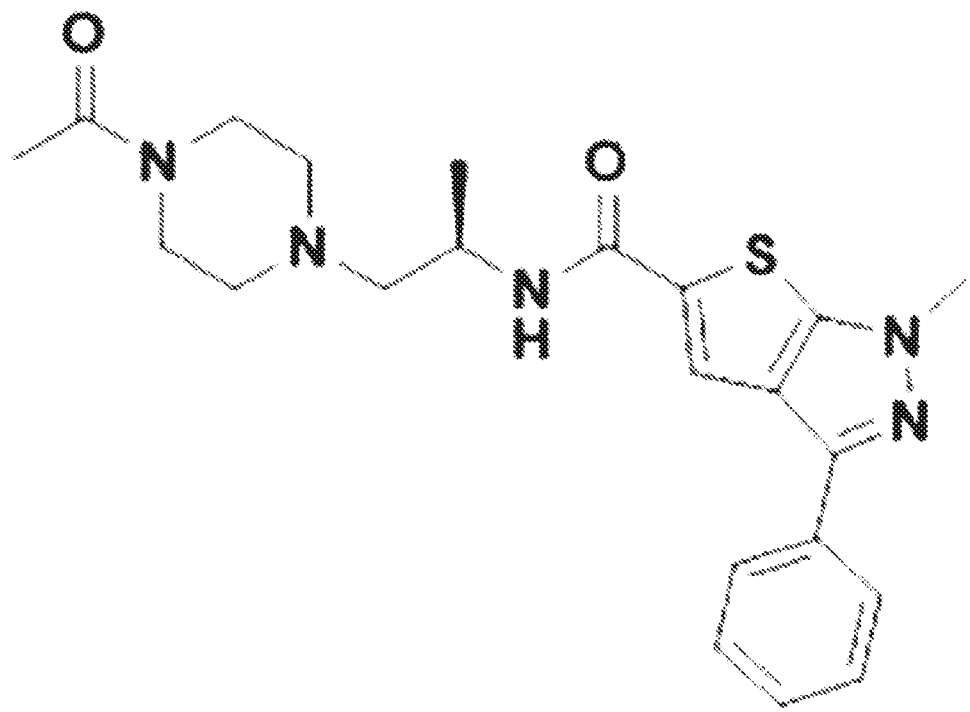
Figure 1D:
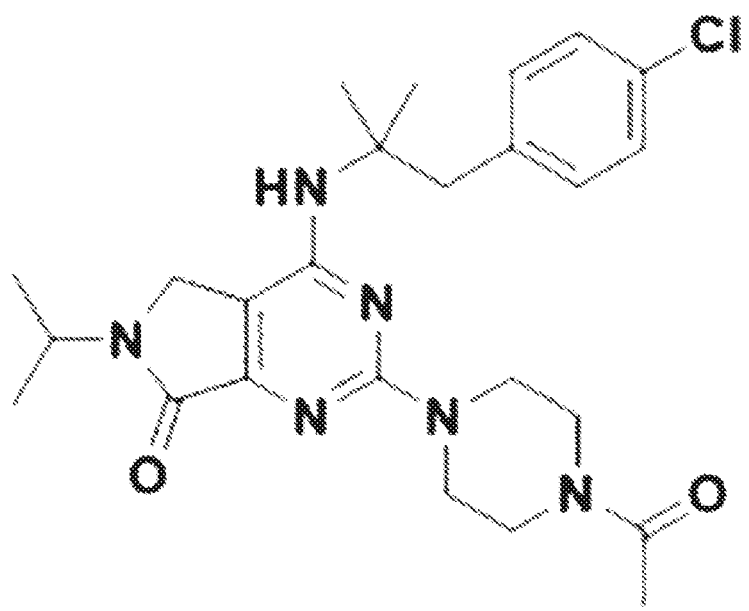
Figure 1E:
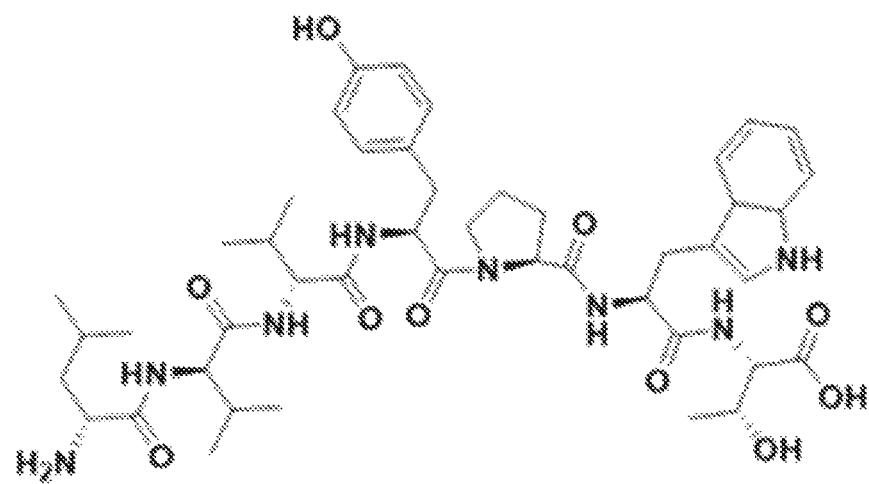
Figure 1F:
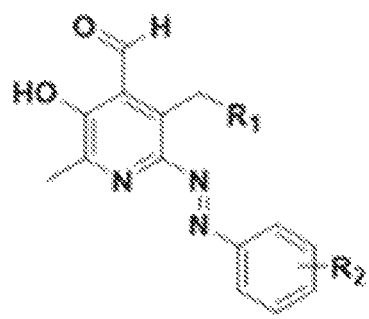
Figure 1G:
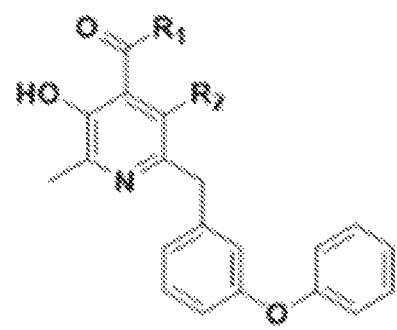

Hereinafter, the present invention will be described in further detail by way of Examples. It would be obvious to those skilled in the art that these Examples are intended to be more concretely illustrative and the scope of the present invention is not limited to or by the Examples.

Reference Example 1. Experiment Preparation

Abbreviations

The definitions of abbreviations used in the Examples are as follows:
ACN, acetonitrile;
ANOVA, analysis of variance;
ATP, adenosine 5-triphosphate;
BBB, blood brain barrier;
BzATP, 2'(3')-O-(4-benzoylbenzoyl)-ATP;
CIPN, chemotherapy-induced peripheral neuropathy;
CYP, cytochrome P450;
DMSO, dimethyl sulfoxide;
FBS, fetal bovine serum;
i.p., intraperitoneal administration;
i.v., intravenous administration;
MPE, maximal possible effect;
NeP, neuropathic pain;
PBS, phosphate buffered saline;
PEG, polyethylene glycol;
P2XR, P2X receptor;
SAR, structure-activity relationship;
SNL, spinal nerve ligation;
TEVC, two-electrode voltage clamp;
TM, transmembrane

Chemical Analysis $^1$H and $^{13}$C nuclear magnetic resonance (NMR) spectra were obtained on a Jeol JNM-LA 300 WB spectrometer at 300 MHz and on a Jeol JNM-ECX 400P spectrometer at 400 MHz, and the spectra were obtained in CDCl$_3$, DMSO-de or CD$_3$OD. Chemical shifts are expressed in units of δ and ppm (parts per million) relative to tetramethylsilane (TMS) as an internal standard. The data are reported as follows: chemical shift, integration, multiplicity (s=singlet, d=doublet, t=triplet, m=multiplet, br=broad). Coupling constants (Q) were measured in Hertz. Mass spectra were obtained on MALDI-TOF and ESI (electrospray ionization). In addition, high-resolution mass spectrometry (m/z) of selected compounds was performed on ESI (Electrospray ionization) at the National Development Institute of Korean Medicine (Jangheung-gun).

The purity of all final compounds was determined by HPLC (unless otherwise noted, the purity was at least 95%). The determination of purity was performed on a Shimadzu SCL-10A VP HPLC system using a Shimadzu Shim-pack C18 analytical column (250 mm 4.6 mm, 5 μm, 100 Å) in a two-solvent system. The solvent system was operated using 0.1% formic acid solution (H$_2$O):CH$_3$CN=90:10 to 1:100 over 30 min with flow rate=1 mL/min. Peaks were detected by UV absorption using a diode array detector.

Example 1. General Procedures for Preparation of Compounds 10a-k

Triethylamine (1.0 equiv) was added dropwise to a mixture of 3-(4-methoxyphenyl)propanoic acid 8 (1.0 equiv), various primary amine compounds 9a-k (1.0 equiv) and EDC (2.0 equiv) in anhydrous dichloromethane. The reaction mixture was stirred at room temperature for 2 hours and then diluted with saturated aqueous sodium bicarbonate solution. The organic layer was separated, and the aqueous layer was further extracted with dichloromethane. The combined organic extracts were dried over anhydrous Na$_2$SO$_4$, concentrated under vacuum and then purified by chromatography on silica gel with n-hexane/ethyl acetate=3:1 to give Compounds 10a-k as viscous oil.

Specific preparation method and physical properties of Compounds 10a-k are as follows.

1-1. Preparation of Ethyl 2-[3-(4-methoxyphenyl)propanoylamino]acetate (10a) Intermediate The intermediate was prepared from Compound 8 (1.0 g, 5.5 mmol) and glycine ethyl ester (0.77 g, 5.5 mmol) according to the general procedures for the synthesis of Compounds 10a-k described above.

Yield 1.4 g (97%); $^1$H NMR (CDCl$_3$, 300 MHz) δ ppm 1.28 (3H, t, J=7.2 Hz, CH$_3$), 2.48-2.95 (2H, m, 2×CH$_2$), 3.78 (3H, s, CH$_3$O), 4.00 (2H, d, J=5.1 Hz, CH$_2$), 4.20 (2H, q, J=7.2 Hz, CH$_2$), 6.00-6.08 (1H, m, NH), 6.79-6.85 (2H, m, phenyl), 7.12 (2H, m, phenyl); MS (ESI): m/z=266.3 [M+H].

1-2. Preparation of Ethyl 2-[3-(4-methoxyphenyl)propanoylamino]propanoate (10b) Intermediate The intermediate was prepared from Compound 8 (5.9 g, 32 mmol) and L-alanine ethyl ester (5.0 g, 32 mmol)

according to the general procedures for the synthesis of Compounds 10a-k described above.

Yield 7.3 g (82%); $^1$H NMR (CDCl$_3$, 300 MHz) δ 1.22 (3H, t, J=7.2 Hz, CH$_3$), 1.35 (3H, d, J=7.2 Hz, CH$_3$), 2.53 (2H, t, J=6.9 Hz, CH$_2$), 2.88 (2H, t, J=6.9 Hz, CH$_2$), 3.79 (3H, s, CH$_3$O), 4.15 (2H, q, J=7.2 Hz, CH$_2$), 4.52-4.59 (1H, m, CH), 5.96 (1H, d, J=5.4 Hz, NH), 6.82-7.19 (4H, m, phenyl); MS (ESI): m/z=280.2 [M+H].

1-3. Preparation of Methyl 2-[3-(4-methoxyphenyl) propanoylamino]butanoate (10c) Intermediate The intermediate was prepared from Compound 8 (0.96 g, 5.3 mmol) and DL-2-aminobutyric acid methyl ester (0.81 g, 5.3 mmol) according to the general procedures for the synthesis of Compounds (10a-o) described above.

Yield 1.4 g (92%); $^1$H NMR (DMSO-d$_6$, 400 MHz) δ 0.79 (3H, t, J=7.2 Hz, CH$_3$), 1.47-1.69 (2H, m, CH$_2$), 2.31-2.40 (2H, m, CH$_2$), 2.66-2.74 (2H, m, CH$_2$), 3.57 (3H, s, CH$_3$O), 3.67 (3H, s, CH$_3$O), 4.07-4.15 (1H, m, CH), 6.76-6.81 (2H, m, phenyl), 7.04-7.10 (2H, m, phenyl); MS (ESI): m/z=280.2 [M+H].

1-4. Preparation of Ethyl 2-[3-(4-methoxyphenyl) propanoylamino]pentanoate (10d) Intermediate The intermediate was prepared from Compound 8 (2.9 g, 17 mmol) and L-norvaline ethyl ester (3.0 g, 17 mmol) according to the general procedures for the synthesis of Compounds (10a-o) described above.

Yield 5.2 g (99%); $^1$H NMR (CDCl$_3$, 400 MHz) δ ppm 0.88 (3H, t, J=7.2 Hz, CH$_3$), 1.11-1.23 (2H, m, CH$_2$), 1.27 (3H, t, J=7.2 Hz, CH$_3$), 1.53-1.57 (2H, m, CH$_2$), 1.69-1.77 (2H, m, CH$_2$), 2.44-2.56 (2H, m, CH$_2$), 2.88-2.95 (2H, m, CH$_2$), 3.78 (3H, s, CH$_3$O), 4.17 (2H, q, J=7.2 Hz, CH$_2$), 4.55-4.60 (1H, m, CH), 5.84-5.86 (1H, m, NH), 6.81 (2H, d, J=8.8 Hz, phenyl), 7.11 (2H, d, J=8.8 Hz, phenyl); MS (ESI): m/z=308.3 [M+H].

1-5. Preparation of Methyl 2-[3-(4-methoxyphenyl) propanoylamino]hexanoate (10e) Intermediate The intermediate was prepared from Compound 8 (0.50 g, 2.8 mmol) and DL-norleucine methyl ester (0.5 g, 2.8 mmol) according to the general procedures for the synthesis of Compounds (10a-o) described above.

Yield 0.79 (89%); $^1$H NMR (CDCl$_3$, 400 MHz) δ ppm 0.85 (3H, t, J=7.2 Hz, CH$_3$), 1.12-1.16 (2H, m, CH$_2$), 1.21-1.28 (2H, m, CH$_2$), 1.54-1.58 (1H, m, CH), 1.71-1.75 (1H, m, CH), 2.43-2.51 (2H, m, CH$_2$), 2.87-2.92 (2H, m, CH$_2$), 3.71 (3H, s, CH$_3$O), 3.76 (3H, s, CH$_3$O), 4.55-4.60 (OH, m, CH), 5.81-5.83 (1H, m, NH), 6.79-6.82 (2H, m, phenyl), 7.10-7.12 (2H, m, phenyl); MS (ESI): m/z=308.1 [M+H].

1-6. Preparation of Ethyl 2-[3-(4-methoxyphenyl) propanoylamino]-3-methyl-butanoate (10f) Intermediate The intermediate was prepared from Compound 8 (2.9 g, 17 mmol) and L-valine ethyl ester (3.0 g, 17 mmol) according to the general procedures for the synthesis of Compounds (10a-o) described above.

Yield 5.00 g (99%); $^1$H NMR (CDCl$_3$, 400 MHz) δ ppm 0.82-0.86 (6H, m, 2×CH$_3$) 1.29 (3H, t, J=6.8 Hz, CH$_3$), 2.07-2.12 (1H, m, CH), 2.48-2.59 (2H, m, CH$_2$), 2.90-2.94 (2H, m, CH$_2$), 3.78 (3H, s, CH$_3$O), 4.16-4.22 (2H, m, CH$_2$), 4.52-4.55 (1H, m, CH), 5.84-5.86 (1H, m, NH), 6.85 (2H, d, J=8.8 Hz, phenyl), 7.16 (2H, d, J=8.4 Hz, phenyl); MS (ESI): m/z=308.7 [M+H].

1-7. Preparation of Ethyl 2-[3-(4-methoxyphenyl) propanoylamino]4-methyl-pentanoate (10g) Intermediate The intermediate was prepared from Compound 8 (2.7 g, 15 mmol) and L-leucine ethyl ester (3.0 g, 15 mmol) according to the general procedures for the synthesis of Compounds (10a-o) described above.

Yield 4.9 g (99%); $^1$H NMR (CDCl$_3$, 400 MHz) δ ppm 0.92 (6H, t, J=6.4 Hz, 2×CH$_3$) 1.25 (3H, t, J=7.2 Hz, CH$_3$), 1.42-1.48 (2H, m, CH$_2$), 1.53-1.57 (1H, m, CH), 2.43-2.53 (2H, m, CH$_2$), 2.87-2.94 (2H, m, CH$_2$), 3.77 (3H, s, CH$_3$O), 4.13 (2H, q, J=7.2 Hz, CH$_{12}$), 4.57 (1H, m, CH), 5.71-5.73 (1H, m, NH), 6.80 (2H, d, J=8.8 Hz, phenyl), 7.10 (2H, d, J=8.4 Hz, phenyl); MS (ESI): m/z=322.7 [M+H].

1-8. Preparation of Ethyl 2-[3-(4-methoxyphenyl) propanoylamino]-3-phenyl-propanoate (10h) Intermediate The intermediate was prepared from Compound 8 (2.3 g, 13 mmol) and L-phenylalanine ethyl ester (3.0 g, 13 mmol) according to the general procedures for the synthesis of Compounds (10a-o) described above.

Yield 4.60 g (99%); $^1$H NMR (CDCl$_3$, 400 MHz) δ ppm 1.22 (3H, t, J=6.8 Hz, CH$_3$) 2.42-2.50 (2H, m, CH$_2$), 2.86-2.91 (2H, m, CH$_2$), 3.06-3.07 (2H, m, CH$_2$), 3.77 (3H, s, CH$_3$O), 4.13-4.19 (2H, m, CH$_2$), 4.86-4.88 (11H, m, CH), 5.84-5.86 (1H, m, NH), 6.81-6.85 (2H, m, phenyl), 6.95-6.98 (2H, m, phenyl), 7.09-7.13 (2H, m, phenyl), 7.22-7.25 (3H, m, phenyl); MS (ESI): m/z=356.3 [M+H].

1-9. Preparation of Ethyl 2-[3-(4-methoxyphenyl) propanoylamino]-4-phenyl-butanoate (10i) Intermediate The intermediate was prepared from Compound 8 (2.2 g, 12 mmol) and D-homophenylalanine ethyl ester (3.0 g, 12 mmol) according to the general procedures for the synthesis of Compounds (10a-o) described above.

Yield 2.40 g (55%); $^1$H NMR (CDCl$_3$, 400 MHz) δ ppm 1.27 (3H, t, J=7.2 Hz, CH$_3$) 1.87-2.16 (2H, m, CH$_2$), 2.41-2.56 (4H, m, 2×CH$_2$), 2.86-2.93 (2H, m, CH$_2$), 3.73 (3H, s, CH$_3$O), 4.14 (2H, q, J=7.2 Hz, CH$_2$), 4.62-4.68 (1H, m, CH), 5.90 (1H, m, NH), 6.81 (2H, d, J=8.4 Hz, phenyl), 7.11-7.15 (4H, m, phenyl), 7.18-7.21 (1H, m, phenyl), 7.26-7.30 (2H, m, phenyl); MS (ESI): m/z=370.3 [M+H].

1-10. Preparation of Diethyl 2-[3-(4-methoxyphenyl)propanoylamino]propanedioate (10j) Intermediate The intermediate was prepared from Compound 8 (2.5 g, 14 mmol) and diethyl aminomalonate (3.0 g, 14 mmol) according to the general procedures for the synthesis of Compounds (10a-o) described above.

Yield 4.40 g (92%); $^1$H NMR (CDCl$_3$, 400 MHz) δ 1.27 (6H, t, J=7.2 Hz, 2×CH$_3$), 2.53-2.57 (2H, m, CH$_2$), 2.88-2.92 (2H, m, CH$_2$), 3.77 (3H, m, CH$_3$), 4.21-4.28 (4H, m, 2×CH$_2$), 5.12-5.13 (1H, m, CH), 6.80-6.82 (2H, d, J=8.4 Hz, phenyl), 7.10-7.12 (2H, d, J=6.8 Hz, phenyl); MS (ESI): m/z=338.1 [M+H].

1-11. Preparation of Ethyl 2-[3-(4-methoxyphenyl)propanoylamino]-4-methylsulfanyl-butanoate (10k) Intermediate The intermediate was prepared from Compound 8 (2.5 g, 14 mmol) and DL-methionine ethyl ester (3.0 g, 14 mmol) according to the general procedures for the synthesis of Compounds (10a-o) described above.

Yield 4.7 g (99%); $^1$H NMR (CDCl$_3$, 400 MHz) δ ppm 1.31 (3H, t, J=6.8 Hz, CH$_3$), 2.08 (3H, s, CH$_3$S), 2.10-2.15 (2H, m, CH$_2$), 2.31-2.61 (4H, m, 2×CH$_2$), 2.91-2.99 (2H, m, CH$_2$), 3.82 (3H, s, CH$_3$O), 4.22-4.26 (2H, q, J=6.8 Hz, CH$_2$), 4.69-4.73 (1H, m, CH), 6.06-6.08 (1H, m, NH), 6.85-6.88 (2H, m, phenyl), 7.15-7.17 (2H, m, phenyl); MS (ESI): m/z=340.2 [M+H].

Example 2. General Procedures for Preparation of Compounds 11a-k

Phosphorous pentoxide (2.0 equiv) was added to a solution of Compounds 10a-k (1.0 equiv) in dried dichloromethane. The mixture was refluxed for 5 hours, cooled to room temperature, and then treated with 20% aqueous KOH solution and vigorously stirred for 30 minutes. The mixture was transferred to a separatory funnel and then extracted three times with dichloromethane. The combined organic extracts were dried over anhydrous Na$_2$SO$_4$, concentrated under vacuum and then purified by chromatography on silica gel with n-hexane/ethyl acetate=3:1 to give Compounds 11a-k as viscous oil.

2-1. Preparation of 5-Ethoxy-2-(4-methoxyphenethyl)oxazole (11a)

The compound was prepared from Compound 10a (1.3 g, 4.9 mmol) and phosphorous pentoxide (2.8 g, 9.8 mmol) according to the general procedures for the synthesis of Compounds 11a-k described above.

Yield 1.3 g (99%); $^1$H NMR (CDCl$_3$, 300 MHz) δ 1.29 (3H, t, J=7.2 Hz, CH$_3$), 2.01 (3H, s, CH$_3$), 3.94 (2H, s, CH$_2$), 4.05 (2H, q, J=7.2 Hz, CH$_2$), 7.23-34 (5H, m, phenyl); MS (ESI): m/z=248.3 [M+H].

2-2. Preparation of S-Ethoxy-2-(4-methoxyphenethyl)-4-methyloxazole (11b)

The compound was prepared from Compound 10b (6.4 g, 22 mmol) and phosphorous pentoxide (13 g, 44 mmol) according to the general procedures for the synthesis of Compounds 11a-k described above.

Yield 5.3 g (91%); $^1$H NMR (CDCl$_3$, 300 MHz) δ 1.31 (3H, t, J=7.2 Hz, CH$_3$), 2.01 (3H, s, CH$_3$), 2.83 (2H, t, J=6.0 Hz, CH$_2$), 2.90 (2H, t, J=6.0 Hz, CH$_2$), 4.05 (3H, s, OCH$_3$), 4.32 (2H, q, J=7.2 Hz, CH$_2$), 6.81 (2H, d, J=8.7 Hz, phenyl), 7.10 (2H, d, J=8.7 Hz, phenyl); MS (ESI): m/z=262.4 [M+H].

2-3. Preparation of 4-Ethyl-5-methoxy-2-(4-methoxyphenethyl)oxazole (11c)

The compound was prepared from Compound 10c (1.4 g, 4.9 mmol) and phosphorous pentoxide (2.8 g, 9.8 mmol) according to the general procedures for the synthesis of Compounds 11a-k described above.

Yield 1.1 g (88%); $^1$H NMR (CDCl$_3$, 400 MHz) δ 1.16 (3H, t, J=7.2 Hz, CH$_3$), 2.38 (2H, q, J=7.2 Hz, CH$_2$), 2.83-3.00 (4H, m, 2×CH$_2$), 3.77 (3H, s, OCH$_3$), 3.84 (3H, s, OCH$_3$), 6.79-6.85 (2H, m, phenyl), 7.06-7.13 (2H, m, phenyl); MS (ESI): m/z=262.4 [M+H].

2-4. Preparation of 5-Ethoxy-2-(4-methoxyphenethyl)-4-propyloxazole (11d)

The compound was prepared from Compound 10d (1.0 g, 3.3 mmol) and phosphorous pentoxide (1.9 g, 6.5 mmol) according to the general procedures for the synthesis of Compounds 11a-k described above.

Yield 0.55 g (58%); $^1$H NMR (CDCl$_3$, 400 MHz) δ ppm 0.83-0.96 (3H, m, CH$_3$), 1.25-1.37 (3H, m, CH$_3$), 1.52-1.64 (2H, m, CH$_2$), 2.25-2.36 (2H, m, CH$_2$), 2.80-3.00 (4H, m, 2×CH$_2$), 3.77 (3H, s, CH$_3$O), 4.01-4.12 (2H, m, CH$_2$), 6.75-6.84 (2H, m, phenyl), 7.03-7.13 (2H, m, phenyl); MS (ESI): m/z=290.0 [M+H].

2-5. Preparation of 4-Butyl-5-methoxy-2-(4-methoxyphenethyl)oxazole (11e)

The compound was prepared from Compound 10e (0.78 g, 2.4 mmol) and phosphorous pentoxide (1.4 g, 4.9 mmol) according to the general procedures for the synthesis of Compounds 11a-k described above.

Yield 0.67 g (91%); $^1$H NMR (CDCl$_3$, 400 MHz) δ ppm 0.88 (3H, t, J=7.2 Hz, CH$_3$), 1.29-1.34 (2H, m, CH$_2$), 1.52-1.58 (2H, m, CH$_2$), 2.84-2.89 (2H, m, CH$_2$), 2.93-2.98 (2H, m, CH$_2$), 3.77 (3H, s, CH$_3$O), 3.84 (3H, s, CH$_3$O), 6.80-6.82 (2H, m, phenyl), 7.08-7.10 (2H, m, phenyl); MS (ESI): m/z=290.2 [M+H].

2-6. Preparation of S-Ethoxy-4-isopropyl-2-(4-methoxyphenethyl)oxazole (11f)

The compound was prepared from Compound 10f (3.0 g, 9.8 mmol) and phosphorous pentoxide (5.5 g, 20 mmol) according to the general procedures for the synthesis of Compounds 11a-k described above.

Yield 2.4 g (84%); $^1$H NMR (CDCl$_3$, 400 MHz) δ ppm 1.18-1.20 (6H, m, 2×CH$_3$), 1.33 (3H, t, J=7.2 Hz, CH$_3$), 2.74-2.81 (1H, m. CH), 2.84-2.89 (2H, m, CH$_2$), 2.93-2.98 (2H, m, CH$_2$), 3.78 (3H, s, CH$_3$O), 4.11 (2H, q, J=7.2 Hz, CH$_2$), 6.81 (2H, d, J=8.4 Hz, phenyl), 7.09 (2H, d, J=8.8 Hz, phenyl); MS (ESI): m/z=290.7 [M+H].

2-7. Preparation of 5-Ethoxy-4-isobutyl-2-(4-methoxyphenethyl)oxazole (11g)

The compound was prepared from Compound 10g (3.0 g, 9.3 mmol) and phosphorous pentoxide (5.3 g, 19 mmol) according to the general procedures for the synthesis of Compounds 11a-k described above.

Yield 2.7 g (94%); $^1$H NMR (CDCl$_3$, 400 MHz) δ ppm 0.89 (6H, d, J=6.8 Hz, 2×CH$_3$), 1.24 (3H, t, J=7.2 Hz, CH$_3$), 1.40-1.53 (2H, m, CH$_2$), 1.53-1.58 (1H, m, CH), 2.44-2.57 (2H, m, CH$_2$), 2.89-2.96 (2H, m, CH$_2$), 3.78 (3H, s, CH$_3$O), 4.15 (2H, q, J=7.2 Hz, CH$_2$), 5.72-5.74 (1H, m, NH), 6.82 (2H, d, J=8.4 Hz, phenyl), 7.12 (2H, d, J=8.4 Hz, phenyl); MS (ESI): m/z=303.8 [M+H].

2-8. Preparation of 4-Benzyl-S-ethoxy-2-(4-methoxyphenethyl) oxazole (11h)

The compound was prepared from Compound 10h (5.1 g, 14 mmol) and phosphorous pentoxide (8.2 g, 28 mmol) according to the general procedures for the synthesis of Compounds 11a-k described above.

Yield 4.0 g (82%); $^1$H NMR (CDCl$_3$, 400 MHz) δ ppm 1.29 (3H, t, J=7.2 Hz, CH$_3$), 2.86-2.98 (2H, m, 2×CH$_2$), 3.73 (2H, s, CH$_2$), 3.79 (3H, s, CH$_3$O), 4.05 (2H, q, J=7.2 Hz, CH$_2$), 6.81 (2H, d, J=8.8 Hz, phenyl), 7.09 (2H, d, J=8.8 Hz, phenyl), 7.19-7.31 (5H, m, phenyl); MS (ESI): m/z=338.4 [M+H].

2-9. Preparation of 5-Ethoxy-2-(4-methoxyphenethyl)-4-phenethyloxazole (11i)

The compound was prepared from Compound 10i (2.5 g, 6.7 mmol) and phosphorous pentoxide (3.8 g, 13 mmol) according to the general procedures for the synthesis of Compounds 11a-k described above.

Yield 2.3 g (98%); $^1$H NMR (CDCl$_3$, 400 MHz) δ ppm 1.20 (3H, t, J=7.2 Hz, CH$_3$) 2.65 (2H, m, CH$_2$), 2.88-3.01 (4H, m, 2×CH$_2$), 3.79 (3H, s, CH$_3$O), 3.82 (2H, q, J=7.2 Hz, CH$_3$), 6.85 (2H, d, J=8.8 Hz, phenyl), 7.13 (2H, d, J=8.8 Hz, phenyl), 7.15-7.19 (3H, m, phenyl), 7.24-7.28 (2H, m, phenyl); MS (ESI): m/z=352.4 [M+H].

2-10. Preparation of Ethyl 5-ethoxy-2-(4-methoxyphenethyl)oxazole-4-carboxylate (11j)

Iodine (3.9 g, 15 mmol), triethylamine (4.3 mL, 31 mmol), and anhydrous dichloromethane solution containing Compound 10j (2.6 g, 8.0 mmol) were added to anhydrous dichloromethane solution containing triphenylphosphine (4.1 g, 15 mmol). The mixture was stirred overnight at room temperature and then washed with water. The organic layer was dried over anhydrous Na$_2$SO$_4$, concentrated under vacuum and then purified by chromatography on silica gel with n-hexane/ethyl acetate=3:1 to give Compound 11j as viscous oil.

Yield 1.6 g (63%); $^1$H NMR (CDCl$_3$, 400 MHz) δ 1.33 (3H, t, J=7.2 Hz, CH$_3$), 1.40 (3H, t, J=7.2 Hz, CH$_3$), 2.93-2.96 (4H, m, 2×CH$_2$), 3.77 (3H, s, CH$_3$), 4.31 (2H, q, J=7.2 Hz, CH$_2$), 4.38 (2H, q, J=7.2 Hz, CH$_2$), 6.81 (2H, d, J=8.8 Hz, phenyl), 7.08 (2H, d, J=8.8 Hz, phenyl); MS (ESI): m/z=320.2 [M+H].

2-11. Preparation of 5-Ethoxy-2-(4-methoxyphenethyl)-4 (2-(methylthio)ethyl)oxazole (11k)

The compound was prepared from Compound 10k (4.7 g, 13 mmol) and phosphorous pentoxide (7.9 g, 28 mmol) according to the general procedures for the synthesis of Compounds 11a-k described above.

Yield 2.7 g (61%); $^1$H NMR (CDCl$_3$, 300 MHz) δ 1.32 (3H, t, J=6.0 Hz, CH$_3$), 2.01 (3H, s, CH$_3$), 2.91 (2H, t, J=5.4 Hz, CH$_2$), 3.04 (2H, t, J=5.4 Hz, CH$_2$), 3.91 (3H, s, COOCH$_3$), 4.06 (2H, q, J=6.0 Hz, CH$_2$), 7.27 (2H, d, J=8.1 Hz, phenyl), 7.95 (2H, d, J=8.1 Hz, phenyl); MS (ESI): m/z=322.5 [M+H].

Example 3. General Procedures for Preparation of Compounds 12a-k

Dimethyl maleate (2.0 equiv) was added to pure Compounds 11a-k (1.0 equiv). The mixture was refluxed for 5 hours and cooled to room temperature. Subsequently, the mixture was diluted with saturated aqueous sodium bicarbonate and then extracted three times with dichloromethane. The combined organic extracts were dried over anhydrous Na$_2$SO$_4$, concentrated under vacuum and then purified by chromatography on silica gel with n-hexane/ethyl acetate=7:1 to give Compounds 12a-k as viscous oil.

3-1. Preparation of Dimethyl 5-hydroxy-2-(4-methoxyphenethyl)pyridine-3,4-dicarboxylate (12a)

The compound was prepared from Compound 11a (0.84 g, 3.4 mmol) and dimethyl maleate (0.85 g, 6.8 mmol) according to the general procedures for the synthesis of Compounds 12a-k described above.

Yield 0.35 g (30%); $^1$H NMR (CDCl$_3$, 400 MHz) δ ppm 2.92 (4H, s, 2×CH$_2$), 3.78 (3H, s, CH$_3$O), 3.89 (3H, s, CH$_3$O), 3.96 (3H, s, CH$_3$O), 6.81-6.83 (2H, m, phenyl), 7.09-7.11 (2H, m, phenyl), 8.53 (1H, s, CH); MS (ESI): m/z=346.3 [M+H].

3-2. Preparation of Dimethyl 5-hydroxy-2-(4-methoxyphenethyl)-6-methylpyridine-3,4-dicarboxylate (12b)

The compound was prepared from Compound 11b (1.5 g, 4.2 mmol) and dimethyl maleate (1.0 g, 8.4 mmol) according to the general procedures for the synthesis of Compounds 12a-k described above.

Yield 0.56 g (37%); $^1$H NMR (CDCl$_3$, 300 MHz) δ 3.02 (3H, s, CH$_3$), 3.04 (2H, t, J=4.8 Hz, CH$_2$), 3.32 (2H, t, J=4.8 Hz, CH$_2$), 3.79 (3H, s, CH$_3$O), 4.00 (3H, s, CH$_3$O), 4.08 (3H, s, CH$_3$O), 6.83 (2H, d, J=5.4 Hz, phenyl), 7.27 (1H, d, J=5.4 Hz, phenyl); MS (ESI): m/z=360.4 [M+H].

3-3. Preparation of Dimethyl 6-ethyl-5-hydroxy-2-(4-methoxyphenethyl)pyridine-3,4-dicarboxylate (12c)

The compound was prepared from Compound 11c (1.3 g, 4.3 mmol) and dimethyl maleate (1.1 g, 8.6 mmol) according to the general procedures for the synthesis of Compounds 12a-k described above.

Yield 0.83 g (52%); $^1$H NMR (CDCl$_3$, 400 MHz) δ 1.27 (3H, t, J=7.2 Hz, CH$_3$), 2.86-2.97 (6H, m, 3×CH$_2$), 3.77 (3H, s, CH$_3$O), 3.86 (3H, s, CH$_3$O), 3.93 (3H, s, CH$_3$O), 6.78-6.84 (2H, m, phenyl), 7.07-7.14 (2H, m, phenyl), 10.53 (1H, s, OH); MS (ESI): m/z=373.5 [M+H].

3-4. Preparation of Dimethyl 5-hydroxy-2-(4-methoxyphenethyl)-6-propylpyridine-3,4-dicarboxylate (12d)

The compound was prepared from Compound 11d (0.55 g, 1.9 mmol) and dimethyl maleate (0.48 g, 3.8 mmol) according to the general procedures for the synthesis of Compounds 12a-k described above.

Yield 0.23 g (30%); $^1$H NMR (CDCl$_3$, 400 MHz) δ 0.98 (3H, t, J=7.6 Hz, CH$_3$), 1.69-1.78 (2H, m, CH$_2$), 2.25-2.36 (2H, m, CH$_2$), 2.85-2.93 (6H, m, 3×CH$_2$), 3.78 (3H, s, CH$_3$O), 3.85 (3H, s, CH$_3$O), 3.93 (3H, s, CH$_3$O), 6.77-6.84 (2H, m, phenyl), 7.06-7.14 (2H, m, phenyl), 10.52 (1H, s, CH); MS (ESI): m/z=388.2 [M+H].

3-5. Preparation of Dimethyl 6-butyl-5-hydroxy-2-(4-methoxyphenethyl)pyridine-3,4-dicarboxylate (12e)

The compound was prepared from Compound 11e (0.67 g, 2.2 mmol) and dimethyl maleate (0.55 g, 4.4 mmol) according to the general procedures for the synthesis of Compounds 12a-k described above.

Yield 0.24 g (27%); $^1$H NMR (CDCl$_3$, 400 MHz) δ 0.92 (3H, t, J=7.2 Hz, CH$_3$), 1.36-1.44 (2H, m, CH$_2$), 1.64-1.71 (2H, m, CH$_2$), 2.86-2.93 (6H, m, 3×CH$_2$), 3.78 (3H, s, CH$_3$O), 3.85 (3H, s, CH$_3$O), 3.92 (3H, s, CH$_3$O), 6.78-6.81 (2H, m, phenyl), 7.08-7.11 (2H, m, phenyl), 10.51 (1H, s, OH); MS (ESI): m/z=402.1 [M+H].

3-6. Preparation of Dimethyl 5-hydroxy-6-isopropyl-2-(4-methoxyphenethyl)pyridine-3,4-dicarboxylate (12f)

The compound was prepared from Compound 11f (2.0 g, 6.9 mmol) and dimethyl maleate (1.7 g, 14 mmol) according to the general procedures for the synthesis of Compounds 12a-k described above.

Yield 0.56 g (21%); $^1$H NMR (CDCl$_3$, 400 MHz) δ ppm 1.23-1.33 (6H, m, 2×CH$_3$), 2.89-2.96 (4H, m, CH$_2$), 3.51-3.56 (1H, m, CH), 3.77 (3H, s, CH$_3$O), 3.85 (3H, s, CH$_3$O), 3.92 (3H, s, CH$_3$O), 6.79 (2H, d, J=8.4 Hz, phenyl), 7.08 (2H, d, J=8.8 Hz, phenyl), 10.55 (1H, s, OH); MS (ESI): m/z=387.7 [M+H].

3-7. Preparation of Dimethyl 5-hydroxy-6-isobutyl-2-(4-methoxyphenethyl)pyridine-3,4-dicarboxylate (12g)

The compound was prepared from Compound 11g (2.0 g, 6.6 mmol) and dimethyl maleate (2.2 g, 13 mmol) according to the general procedures for the synthesis of Compounds 12a-k described above.

Yield 0.86 g (34%); $^1$H NMR (CDCl$_3$, 400 MHz) δ ppm 0.97 (6H, d, J=6.8 Hz, 2×CH$_3$), 2.15-2.22 (1H, m, CH), 2.77 (2H, d, J=7.2 Hz, CH$_2$), 2.92 (4H, s, CH$_2$), 3.77 (3H, s, CH$_3$O), 3.85 (3H, s, CH$_3$O), 3.93 (3H, s, CH$_3$O), 6.80 (2H, d, J=8.4 Hz, phenyl), 7.10 (2H, d, J=8.8 Hz, phenyl), 10.50 (1H, s, OH); MS (ESI): m/z=401.7 [M+H].

3-8. Preparation of Dimethyl 6-benzyl-5-hydroxy-2-(4-methoxyphenethyl)pyridine-3,4-dicarboxylate (12h)

The compound was prepared from Compound 11h (3.9 g, 12 mmol) and dimethyl maleate (3.0 g, 24 mmol) according to the general procedures for the synthesis of Compounds 12a-k described above.

Yield 1.4 g (27%); $^1$H NMR (CDCl$_3$, 400 MHz) δ ppm 2.90-2.96 (4H, m, 2×CH$_2$), 3.78 (3H, s, CH$_3$O), 3.85 (3H, s, CH$_3$O), 3.91 (3H, s, CH$_3$O), 4.24 (2H, s, CH$_2$), 6.80 (2H, d, J=8.4 Hz, phenyl), 7.09 (2H, d, J=8.8 Hz, phenyl), 7.18-7.34 (4H, m, CH), 10.51 (1H, s, OH); MS (ESI): m/z=436.3 [M+H].

3-9. Preparation of Dimethyl 5-hydroxy-2-(4-methoxyphenethyl)-6-phenethylpyridine-3,4-dicarboxylate (12i)

The compound was prepared from Compound 11i (1.0 g, 2.9 mmol) and dimethyl maleate (0.71 g, 5.8 mmol) according to the general procedures for the synthesis of Compounds 12a-k described above.

Yield 0.36 g (28%); $^1$H NMR (CDCl$_3$, 400 MHz) δ ppm 2.91 (4H, s, 2×CH$_2$), 3.03-3.07 (2H, m, CH$_2$), 3.21-3.25 (2H, m, CH$_2$), 3.79 (3H, s, CH$_3$O), 3.87 (3H, s, CH$_3$O), 3.95 (3H, s, CH$_3$O), 6.84 (2H, d, J=8.8 Hz, phenyl), 7.12 (2H, d, J=8.8 Hz, phenyl), 7.27-7.30 (5H, m, CH), 10.56 (1H, s, OH); MS (ESI): m/z=450.2 [M+H].

3-10. Preparation of 2-Ethyl 4,5-dimethyl 3-hydroxy-6-(4-methoxyphenethyl)pyridine-2,4,5-tricarboxylate (12j)

The compound was prepared from Compound 11j (1.0 g, 3.1 mmol) and dimethyl maleate (0.78 g, 6.2 mmol) according to the general procedures for the synthesis of Compounds 12a-k described above.

Yield 0.32 g (24%); $^1$H NMR (CDCl$_3$, 400 MHz) δ 1.26 (3H, t, J=7.2 Hz, CH$_3$), 2.50-2.59 (2H, m, CH$_2$), 3.16-3.23 (2H, m, CH$_2$), 3.77 (3H, s, CH$_3$O), 3.78 (3H, s, CH$_3$O), 3.81 (3H, s, CH$_3$O), 4.20-4.29 (2H, m, CH$_2$), 6.80-6.84 (2H, m, phenyl), 7.06-7.12 (2H, m, phenyl); MS (ESI): m/z=416.0 [M−H].

3-11. Preparation of Dimethyl-hydroxy-2-[2-(4-methoxyphenyl)ethyl]-6-(2-methylsulfanylethyl)pyridine-3,4-dicarboxylate (12k)

The compound was prepared from Compound 11k (1.0 g, 3.1 mmol) and dimethyl maleate (0.78 g, 6.2 mmol) according to the general procedures for the synthesis of Compounds 12a-k described above.

Yield 0.47 g (36%); $^1$H NMR (CDCl$_3$, 400 MHz) δ ppm 2.18 (3H, s, CH$_3$S), 2.89-2.97 (6H, m, 3×CH$_2$), 3.19-3.23 (2H, m, CH$_2$), 3.79 (3H, s, CH$_3$O), 3.87 (3H, s, CH$_3$O), 3.95 (3H, s, CH$_3$O), 6.82 (2H, d, J=8.8 Hz, phenyl), 7.10 (2H, d, J=8.8 Hz, phenyl), 10.57 (1H, s, OH); MS (ESI): m/z=420.3 [M+H].

3-12. Preparation of Dimethyl 5-hydroxy-2-(4-methoxyphenethyl)-6-(2-(methylsulfonyl)ethyl)pyridine-3,4-dicarboxylate (12l)

Water (0.5 mL), in which Oxone® was dissolved (221 mg, 0.36 mmol), was added to a methanol:tetra hydrofuran (3:1, 0.5 mL) solution, in which Compound 12k (50 mg, 0.12 mmol) was dissolved, at 0° C. The mixture was stirred at room temperature for 4 hours. Subsequently, the mixture was poured over saturated aqueous sodium bicarbonate and extracted with chloroform.

The combined organic extracts were dried over anhydrous Na$_2$SO$_4$, concentrated under vacuum and then purified by chromatography on silica gel with n-hexane/ethyl acetate=1:1 to give Compound 12l as viscous oil.

Yield 48 mg (88%); $^1$H NMR (DMSO-d$_6$, 400 MHz) δ ppm 2.80-2.82 (2H, m, CH$_2$), 2.89-2.91 (2H, m, CH$_2$), 2.99 (3H, s, CH$_3$S) 3.17-3.20 (2H, m, CH$_2$), 3.44-3.48 (2H, m, CH$_2$), 3.66 (3H, s, CH$_3$O), 3.72 (3H, s, CH$_3$O), 3.77 (3H, s, CH$_3$O), 6.85-6.88 (2H, d, J=8.8 Hz, phenyl), 7.02-7.04 88 (2H, d, J=8.8 Hz, phenyl); MS (ESI): m/z=452.0 [M+H].

Example 4. General Procedures for Preparation of Compounds 13a-l

The solution of Compounds 12a-l in 20% aqueous KOH solution was stirred vigorously for 6 hours. Concentrated HCl solution was added to the mixture for acidification, and the precipitated product was filtered with excess of water and chloroform. The product was then dried to give Compounds 13a-l as a white solid.

4-1. Preparation of 5-Hydroxy-2-(4-methoxyphenethyl)pyridine-3,4-dicarboxylic add (13a)

The compound was prepared from Compound 12a (0.20 g, 0.63 mmol) and 20% aqueous KOH solution (5.0 mL)

according to the general procedures for the synthesis of Compounds (13a-1) described above.

Yield 0.11 g (52%); $^1$H NMR (DMSO-d$_6$, 300 MHz) δ ppm 2.79-3.00 (4H, m, 2×CH$_2$), 3.71 (3H, s, CH$_3$O), 6.82-6.85 (2H, m, phenyl), 7.09-7.12 (2H, m, phenyl), 8.30 (1H, s, CH); MS (ESI): m/z=318.2 [M+H]; HRMS (ESI) [M+H]$^+$ (C$_{16}$H$_{15}$NO$_6$): calcd. 318.0972, found. 318.0957; Purity 98.1%.

4-2. Preparation of 5-Hydroxy-2-(4-methoxyphenethyl)-6-methylpyridine-3,4-dicarboxylic acid (13b)

The compound was prepared from Compound 12b (0.20 g, 0.55 mmol) and 20% aqueous KOH solution (5.0 mL) according to the general procedures for the synthesis of Compounds (13a-1) described above.

Yield 0.12 g (65%); $^1$H NMR (DMSO-d, 300 MHz) δ 2.25 (3H, s, CH$_3$), 2.80-2.95 (4H, m, 2×CH$_2$), 3.80 (3H, s, CH$_3$O), 6.91 (2H, d, J=8.7 Hz, phenyl), 7.21 (2H, d, J=8.7 Hz, phenyl); $^{13}$C NMR (DMSO-d$_6$, 400 MHz) 19.07, 35.48, 37.68, 55.43, 114.12, 120.40, 128.32, 129.68, 135.06, 142.99, 144.39, 157.83, 166.88, 171.98, 175.15; MS (ESI): m/z=332.3 [M+H]; HRMS (ESI) [M+H]$^+$ (C$_{17}$H$_{17}$NO$_6$): calcd. 332.1129, found. 332.1115; Purity 98.1%.

4-3. Preparation of 6-Ethyl-5-hydroxy-2-(4-methoxyphenethyl)pyridine-3,4-dicarboxylic acid (13c)

The compound was prepared from Compound 12c (0.30 g, 0.80 mmol) and 20% aqueous KOH solution (5.0 mL) according to the general procedures for the synthesis of Compounds (13a-1) described above.

Yield 97 mg (35%); $^1$H NMR (DMSO-d$_6$, 400 MHz) δ 1.14 (3H, t, J=7.2 Hz, CH$_3$), 2.43-2.92 (6H, m, 3×CH$_2$), 3.67 (3H, s, CH$_3$O), 6.79-6.85 (2H, m, phenyl), 7.02-7.08 (2H, m, phenyl); MS (ESI): m/z=345.7 [M+H]; HRMS (ESI) [M+H]$^+$ (C$_{18}$H$_{19}$NO$_6$): calcd. 346.1285, found. 346.1266; Purity 97.1%.

4-4. Preparation of 5-Hydroxy-2-(4-methoxyphenethyl)-6-propylpyridine-3,4-dicarboxylic acid (13d)

The compound was prepared from Compound 12d (0.20 g, 0.52 mmol) and 20% aqueous KOH solution (5.0 mL) according to the general procedures for the synthesis of Compounds (13a-1) described above.

Yield 0.10 g (51%); $^1$H NMR (DMSO-d$_6$, 400 MHz) δ 0.90 (3H, t, J=7.2 Hz, CH$_3$), 1.54-1.64 (2H, m, CH$_2$), 2.73-2.80 (4H, m, 2×CH$_2$), 2.85-2.89 (2H, m, CH$_2$), 3.67 (3H, s, CH$_3$O), 6.78-6.85 (2H, m, phenyl), 7.02-7.08 (2H, m, phenyl); $^{13}$C NMR (DMSO-d$_6$, 400 MHz) δ 13.8, 21.1, 31.3, 34.4, 34.7, 55.2, 113.9, 114.0, 123.8, 129.3, 129.4, 132.4, 149.9, 157.9, 167.3, 167.8; MS (ESI): m/z=359.8 [M+H]; HRMS (ESI) [M+H]$^+$ (C$_{19}$H$_{21}$NO$_6$): calcd. 360.1442, found. 360.1421; Purity 97.3%.

4-5. Preparation of 6-Butyl-5-hydroxy-2-(4-methoxyphenethyl)pyridine-3,4-dicarboxylic acid (13e)

The compound was prepared from Compound 12e (0.24 g, 0.59 mmol) and 20% aqueous KOH solution (5.0 mL) according to the general procedures for the synthesis of Compounds (13a-1) described above.

Yield 0.12 g (57%); $^1$H NMR (DMSO-ds, 400 MHz) δ 0.84 (3H, t, J=7.2 Hz, CH$_2$), 1.24-1.30 (2H, m, CH$_2$), 1.51-1.55 (2H, m, CH$_2$), 2.45-2.47 (2H, m, CH$_2$), 2.76-2.82 (2H, m, CH$_2$), 2.85-2.90 (2H, m, CH$_2$), 3.67 (3H, s, CH$_3$O), 6.80-6.82 (2H, m, phenyl), 7.03-7.05 (2H, m, phenyl); MS (ESI): m/z=374.1 [M+H]; HRMS (ESI) [M+H]$^+$ (C$_{20}$H$_{23}$NO$_6$): calcd. 374.1598, found. 374.1575; Purity 97.4%.

4-6. Preparation of 5-Hydroxy-6-isopropyl-2-(4-methoxyphenethyl)pyridine-3,4-dicarboxylic acid (13f)

The compound was prepared from Compound 12f (0.30 g, 0.77 mmol) and 20% aqueous KOH solution (5.0 mL) according to the general procedures for the synthesis of Compounds (13a-1) described above.

Yield 0.14 g (52%); $^1$H NMR (DMSO-d$_6$, 400 MHz) δ ppm 1.16-1.18 (6H, m, 2×CH$_3$), 2.81-2.90 (4H, m, CH$_2$), 3.37-3.43 (1H, m, CH), 3.67 (3H, s, CH$_3$O), 6.79 (2H, d, J=8 Hz, phenyl), 7.04 (2H, d, J=8.4 Hz, phenyl); $^{13}$C NMR (DMSO-d$_6$, 400 MHz) δ 22.3, 27.8, 34.1, 34.6, 37.8, 55.1, 114.0, 124.0, 129.4, 132.2, 149.1, 157.9, 167.2, 167.7; MS (ESI): m/z=359.5 [M+H]; HRMS (ESI) [M+H]$^+$ (C$_{19}$H$_{21}$NO$_6$): calcd. 360.1442, found. 360.1423; Purity 96.1%.

4-7. Preparation of 5-Hydroxy-6-isobutyl-2-(4-methoxyphenethyl)pyridine-3,4-dicarboxylic acid (13g)

The compound was prepared from Compound 12g (0.86 g, 2.2 mmol) and 20% aqueous KOH solution (5.0 mL) according to the general procedures for the synthesis of Compounds (13a-1) described above.

Yield 0.35 g (43%); $^1$H NMR (DMSO-d, 400 MHz) δ ppm 0.82 (6H, d, J=6.8 Hz, 2×CH$_3$), 1.99-2.02 (1H, m, CH), 2.68 (2H, m, CH$_2$), 2.78-2.92 (4H, m, CH$_2$), 3.67 (3H, s, CH$_3$O), 6.82 (2H, d, J=8.4 Hz, phenyl), 7.04 (2H, d, J=8.4 Hz, phenyl); MS (ESI): m/z=374.5 [M+H]; HRMS (ESI) [M+H]+ (C20H23NO6): calcd. 374.1598, found. 374.1572; Purity 98.0%.

4-8. Preparation of 6-Benzyl-5-hydroxy-2-(4-methoxyphenethyl)pyridine-3,4-dicarboxylic acid (13h)

The compound was prepared from Compound 12h (0.45 g, 1.0 mmol) and 20% aqueous KOH solution (5.0 mL) according to the general procedures for the synthesis of Compounds (13a-1) described above.

Yield 0.39 g (90%); $^1$H NMR (DMSO-d$_6$, 400 MHz) δ ppm 2.80-2.92 (4H, m, 2×CH$_2$), 3.68 (3H, s, CH$_3$O), 4.13 (2H, s, CH$_2$), 6.78 (2H, d, J=8.8 Hz, phenyl), 7.04 (2H, d, J=8.4 Hz, phenyl), 7.15-7.26 (5H, m, phenyl); $^{13}$C NMR (DMSO-d$_6$, 400 MHz) δ 34.7, 35.5, 36.7, 55.4, 114.3, 126.9, 128.9, 129.1, 129.7, 133.0, 138.1, 149.4, 158.1, 168.1, 168.4; MS (ESI): m/z=408.2 [M+H]; HRMS (ESI) [M+H]$^+$ (C$_{23}$H$_{21}$NO$_6$): calcd. 408.1442, found. 408.1442; Purity 98.6%.

4-9. Preparation of 5-Hydroxy-2-(4-methoxyphenethyl)-6-phenethylpyridine-3,4-dicarboxylic acid (13i)

The compound was prepared from Compound 12i (0.15 g, 0.33 mmol) and 20% aqueous KOH solution (5.0 mL) according to the general procedures for the synthesis of Compounds (13a-1) described above.

Yield 88 mg (63%); $^1$H NMR (DMSO-d$_6$, 400 MHz) δ ppm 2.72-2.76 (2H, m, CH$_2$), 2.84-2.92 (4H, m, 2×CH$_2$), 3.06-3.10 (2H, m, CH$_2$), 3.67 (3H, s, CH$_3$O), 6.81 (2H, d, J=8.8 Hz, phenyl), 7.04 (2H, d, J=8.4 Hz, phenyl), 7.16-7.20 (3H, m, phenyl), 7.25-7.28 (2H, m, phenyl); MS (ESI): m/z=421.0 [M–H]; HRMS (ESI) [M+H]$^+$ (C$_{24}$H$_{23}$NO$_6$): calcd. 422.1598, found. 422.1572; Purity 95.0%.

4-10. Preparation of 3-Hydroxy-6-(4-methoxyphenethyl)pyridine-2,4,5-tricarboxylic acid (13j)

The compound was prepared from Compound 12j (0.20 g, 0.48 mmol) and 20% aqueous KOH solution (5.0 mL) according to the general procedures for the synthesis of Compounds (13a-1) described above.

Yield 0.10 g (55%); $^1$H NMR (DMSO-de, 400 MHz) δ 2.66-2.70 (2H, m, CH$_2$), 3.05-3.09 (2H, m, CH$_2$), 3.65 (3H, s, CH$_3$), 6.78 (2H, d, J=7.6 Hz, phenyl), 7.06 (2H, d, J=8.0 Hz, phenyl); MS (ESI): m/z=362.1 [M+H].

4-11. Preparation of 5-Hydroxy-2-(4-methoxyphenethyl)$_6$-(2-(methylthio)ethyl)pyridine-3,4-dicarboxylic acid (13k)

The compound was prepared from Compound 12k (0.47 g, 1.1 mmol) and 20% aqueous KOH solution (5.0 mL) according to the general procedures for the synthesis of Compounds (13a-1) described above.

Yield 0.22 g (52%); $^1$H NMR (DMSO-4 400 MHz) δ ppm 2.06 (3H, s, CH$_3$S), 2.76-2.90 (6H, m, 3×CH$_2$), 3.04-3.08 (2H, m, CH$_2$), 3.68 (3H, s, CH$_3$O), 6.81 (2H, d, J=8.4 Hz, phenyl), 7.05 (2H, d, J=8.4 Hz, phenyl); MS (ESI): m/z=392.4 [M+H]; HRMS (ESI) [M+H]$^+$ (C$_{19}$H$_{21}$NO$_6$S): calcd. 392.1162, found. 392.1142; Purity 95.4%.

4-12. Preparation of 5-Hydroxy-2-(4-methoxyphenethyl)-6-(2-(methylsulfonyl)ethyl)pyridine-3,4-dicarboxylic add (13l)

The compound was prepared from Compound 12l (70 mg, 0.16 mmol) and 20% aqueous KOH solution (5.0 mL) according to the general procedures for the synthesis of Compounds (13a-1) described above.

Yield 32 mg (47%); $^1$H NMR (DMSO-d$_6$, 400 MHz) δ ppm 2.80-2.83 (2H, m, CH$_2$), 2.85-2.87 (2H, m, CH$_2$), 3.00 (3H, s, CH$_3$S), 3.16-3.20 (2H, m, CH$_2$), 3.43-3.47 (2H, m, CH$_2$), 3.67 (3H, s, CH$_3$O), 6.80-6.82 (2H, d, J=8.8 Hz, phenyl), 7.06-7.08 (2H, d, J=8.8 Hz, phenyl); $^{13}$C NMR (DMSO-d$_6$, 400 MHz) δ 24.0, 34.5, 36.2, 40.4, 51.1, 55.1, 113.9, 122.0, 128.3, 129.3, 129.4, 133.3, 147.3, 157.7, 168.3, 168.6; MS (ESI): m/z=423.8 [M+H]; HRMS (ESI) [M+H]$^+$ (C$_{19}$H$_{21}$NO$_8$S): calcd. 424.1061, found. 424.1038; Purity 96.8%.

Example 5. Preparation of Ethyl 4-cyano-5-hydroxy-2-(4-methoxyphenethyl)-6-methylnicotinate (14)

The compound was prepared from Compound 11b (0.49 g, 1.9 mmol) and ethyl cis-beta-cyanoacrylate (0.23 mL, 1.9 mmol) according to the general procedures for the synthesis of Compounds 12a-k described above.

Yield 0.18 g (27%); $^1$H NMR (CDCl$_3$, 400 MHz) δ 1.38 (3H, t, J=7.2 Hz, CH$_3$), 2.58 (3H, s, CH$_3$), 2.88-2.95 (2H, m, CH$_2$), 3.17-3.21 (2H, m, CH$_2$), 3.77 (3H, s, CH$_3$), 4.38-4.34 (2H, m, CH$_2$), 6.79-6.81 (2H, m, phenyl), 7.08-7.11 (2H, m, phenyl); MS (ESI): m/z=341.5 [M+H].

Example 6. Preparation of Ethyl 5-hydroxy-2-(4-methoxyphenethyl)-6-methyl-4-(1H-tetrazol-5-yl)nicotinate (15)

A mixture of Compound 14 (0.18 g, 0.52 mmol), sodium azide (33 mg, 0.52 mmol) and ammonium chloride (28 mg, 0.52 mmol) in DMF (10 mL) was added to a round bottom flask and stirred overnight at 90° C. After completion of the reaction, the reaction mixture was cooled. 1N aqueous HCl solution (17 mL) was added to the reaction mixture to induce the formation of precipitates. The precipitated product was obtained by filtration, and the thus-obtained precipitate was washed with excess water and chloroform. The product was then dried to give Compound 15 as a white solid.

Yield 95 mg (48%); $^1$H NMR (CDCl$_3$, 400 MHz) δ 0.96 (3H, t, J=7.2 Hz, CH$_3$), 2.52 (3H, s, CH$_3$), 2.80-2.85 (2H, m, CH$_2$), 2.88-2.96 (2H, m, CH$_2$), 3.67 (3H, s, CH$_3$), 4.05-4.12 (2H, m, CH$_2$), 6.80-6.82 (2H, m, phenyl), 7.05-7.08 (2H, m, phenyl); MS (ESI): m/z=384.3 [M+H].

Example 7. Preparation of 4-Cyano-5-hydroxy-2-(4-methoxyphenethyl)-6-methylnicotinic acid (16)

The compound was prepared from Compound 14 (0.10 g, 0.30 mmol) and 20% aqueous KOH solution (3.0 mL) according to the general procedures for the synthesis of compound (13a-1) described above.

Yield 30 mg (30%); $^1$H NMR (DMSO-d$_6$, 400 MHz) δ 2.44 (3H, s, CH$_3$), 2.83-2.87 (2H, m, CH$_2$), 3.03-3.07 (2H, m, CH$_2$), 3.67 (3H, s, CH$_3$), 6.78-6.82 (2H, m, phenyl), 7.04-7.10 (2H, m, phenyl); 13C NMR (DMSO-4, 400 MHz) δ 17.4, 35.1, 37.8, 55.2, 113.8, 113.9, 114.0, 122.6, 129.3, 129.4, 133.3, 146.9, 157.7, 169.1; MS (ESI): m/z=311.3 [M–H]; HRMS (ESI) [M+H]$^+$ (C$_{17}$H$_{16}$N$_2$O$_4$): calcd. 313.1183, found. 313.1167; Purity 97.6%.

Example 8. Preparation of 5-Hydroxy-2-(4-methoxyphenethyl)-6-methyl-4-(1H-tetrazol-5-yl)nicotinic acid (17)

The compound was prepared from Compound 15 (0.10 g, 0.30 mmol) and 20% aqueous KOH solution (3.0 mL) according to the general procedures for the synthesis of compound (13a-1) described above.

Yield 31 mg (30%); $^1$H NMR (DMSO-d$_6$, 400 MHz) δ 2.51 (3H, s, CH$_3$), 2.81-2.86 (2H, m, CH$_2$), 2.92-2.97 (2H, m, CH$_2$), 3.68 (3H, s, CH$_3$), 6.80-6.84 (2H, m, phenyl), 7.08-7.11 (2H, m, phenyl); MS (ESI): m/z=354.4 [M–H]; HRMS (ESI) [M+H]$^+$ (C$_{17}$H$_{17}$N$_5$O$_4$): calcd. 356.1353, found. 356.1335; Purity 98.7%.

Example 9. Preparation of 7-Hydroxy-4-(4-methoxyphenethyl)-6-methylfuro[3,4-c]pyridine-1,3-dione (18)

A mixture of Compound 11b (0.50 g, 1.9 mmol) and maleic anhydride (0.19 g, 1.9 mmol) in benzene (6 mL) was heated at 60° C. for 2 hours. After completion of the reaction, the reaction mixture was cooled. The precipitated product was obtained by filtration, and thus-obtained precipitate was washed with excess diethyl ether. The product was then dried to give Compound 18.

Yield 0.32 g (54%); $^1$H NMR (DMSO-d$_6$, 400 MHz) δ 2.52 (3H, s, CH$_3$), 2.82-2.86 (2H, m, CH$_2$), 3.16-3.20 (2H, m, CH$_2$), 3.67 (3H, s, CH$_3$), 6.79-6.81 (2H, m, phenyl), 7.09-7.11 (2H, m, phenyl); $^{13}$C NMR (DMSO-d$_6$, 400 MHz) δ 16.6, 34.8, 35.3, 55.5, 114.2, 114.4, 123.9, 129.6, 132.9, 147.3, 158.2, 167.5, 168.1; MS (ESI): m/z=314.3 [M+H].

Example 10. Preparation of 8-Hydroxy-5-(4-methoxyphenethyl)-7-methyl-2,3-dihydropyrido[3,4]pyridazine-1,4-dione (19)

Acetic acid (300 μL), in which Compound 18 (0.29 g, 0.92 mmol) was dissolved, was added dropwise to a solution of hydrazine hydrate (36 μL, 1.2 mmol) in water (400 μL). Sodium acetate anhydride (0.098 g, 1.2 mmol) was added thereto, and the reaction mixture was heated to reflux for 2 hours. After completion of the reaction, the reaction mixture was cooled. The thus-prepared mixture was diluted with ethyl acetate and washed with water and brine. The combined organic layers were dried over anhydrous Na$_2$SO$_4$, concentrated under vacuum and then purified by chromatography on silica gel with chloroform/methanol=10:1 to give Compound 19.

Yield 0.14 g (46%); $^1$H NMR (CDCl$_3$, 400 MHz) δ 2.47 (3H, s, CH$_3$), 2.79-2.83 (2H, m, CH$_2$), 3.51-3.55 (2H, m, CH$_2$), 3.73 (3H, s, CH$_3$), 6.77-6.79 (2H, m, phenyl), 7.18-7.20 (2H, m, phenyl); MS (ESI): m/z=328.1 [M+H]; HRMS (ESI) [M+H]$^+$ (C$_7$H$_{17}$N$_3$O$_4$): calcd. 328.1292, found. 328.1277; Purity 95.1%.

Example 11. Preparation of 6-(4-Methoxyphenethyl)-2-methyl-4-(methylsulfonyl)pyridin-3-ol (20)

The compound was synthesized from Compound 11b (0.50 g, 1.9 mmol) and methyl vinyl sulfone (0.41 mL, 3.8 mmol) according to the general procedures for the synthesis of Compounds 12a-k.

Yield 0.30 g (49%); $^1$H NMR (CD$_3$OD, 400 MHz) δ 2.49 (3H, s, CH$_3$), 2.88 (2H, m, CH$_2$), 2.98 (2H, m, CH$_2$), 3.22 (3H, s, SCH$_3$), 3.72 (3H, s, OCH$_3$), 6.76-6.81 (2H, m, phenyl), 7.02-7.06 (2H, m, phenyl), 7.31 (1H, s, phenyl); MS (ESI): m/z=322.2 [M+H]; HRMS (ESI) [M+H]$^+$ (C$_{16}$H$_{19}$NO$_4$S): calcd. 322.1108, found. 322.1100; Purity 96.8%.

Example 12. Preparation of Methyl 3-hydroxy-6-(4-methoxyphenethyl)-2-methylisonicotinate (21a)

The compound was synthesized from Compound 11b (1.0 g, 3.8 mmol) and methyl acrylate (0.68 mL, 7.6 mmol) according to the general procedures for the synthesis of Compounds 12a-k.

Yield 0.43 g (37%); $^1$H NMR (CDCl$_3$, 400 MHz) δ 2.54 (3H, s, CH$_3$), 2.91-3.01 (4H, m, 2×CH$_2$), 3.77 (3H, s, CH$_3$O), 3.95 (3H, s, CH$_3$O), 6.79-6.84 (2H, m, phenyl), 7.09-7.14 (2H, m, phenyl). 7.24 (1H, s, phenyl), 10.43 (1H, s, OH); MS (ESI): m/z=302.1 [M+H].

Example 13. Preparation of Methyl 3-hydroxy-6-(4-methoxyphenethyl)-2,5-dimethylisonicotinate (21b)

The compound was synthesized from Compound 11b (1.2 g, 4.4 mmol) and methyl crotonate (0.93 mL, 8.8 mmol) according to the general procedures for the synthesis of Compounds 12a-k.

Yield 0.49 g (35%); $^1$H NMR (CDCl$_3$, 300 MHz) δ 2.36 (3H, s, CH), 2.51 (3H, s, CH$_3$), 2.84-2.92 (2H, m, CH$_2$), 3.00-3.08 (2H, m, CH$_2$), 3.79 (3H, s, CH$_3$O), 3.99 (3H, s, CH$_3$O), 6.80-6.85 (2H, m, phenyl), 7.10-7.16 (2H, m, phenyl); MS (ESI): m/z=316.2 [M+H].

Example 14. Preparation of Methyl 3-hydroxy-6-(4-methoxyphenethyl)-5-methyl-2-propylisonicotinate (21c)

The compound was synthesized from Compound 11b (1.6 g, 5.5 mmol) and methyl crotonate (1.2 mL, 11 mmol) according to the general procedures for the synthesis of Compounds 12a-k.

Yield 0.64 g (34%); $^1$H NMR (CDCl$_3$, 400 MHz) δ 0.98 (3H, t, J=7.2 Hz, CH$_3$), 1.68-1.76 (2H, m, CH$_2$), 2.33 (3H, s, CH$_3$), 2.78-2.85 (2H, m, CH$_2$), 2.85-2.93 (2H, m, CH$_2$), 3.00-3.07 (2H, m, CH$_2$), 3.77 (3H, s, CH$_3$O), 3.97 (3H, s, CH$_3$O), 6.79-6.82 (2H, m, phenyl), 7.08-7.12 (2H, m, phenyl), 10.21 (1H, s, OH); MS (ESI): m/z=344.0 [M+H].

Example 15. Preparation of 3-Hydroxy-6-(4-methoxyphenethyl)-2-methylisonicotinic acid (22a)

A solution of Compound 21a (0.19 mg, 0.63 mmol) in 20% aqueous KOH solution (3.0 mL) was stirred vigorously for 6 hours. Concentrated HCl solution was added to the mixture for acidification, and the mixture was concentrated under vacuum. KCl salt was removed by filtration. Subsequently, the filtrate was concentrated under vacuum, and the residue was purified by chromatography on silica gel with chloroform/methanol=20:1 to give Compound 22a.

Yield 87 mg (48%;) $^1$H NMR (DMSO-d$_6$, 300 MHz) 2.51 (3H, s, CH$_3$), 2.74-2.82 (2H, m, CH$_2$), 3.15-3.20 (2H, m, CH$_2$), 3.71 (3H, s, CH$_3$O), 6.80-6.86 (2H, m, phenyl), 7.11-7.16 (2H, m, phenyl); $^{13}$C NMR (DMSO-d, 400 MHz) δ 14.9, 34.4, 55.1, 114.0, 122.9, 129.5, 132.2, 144.6, 157.8, 167.9; MS (ESI): m/z=288.2 [M+H]; HRMS (ESI) [M+H]$^+$ (C$_{16}$H$_{17}$NO$_4$): calcd. 288.1230, found. 288.1213; Purity 97.3%.

Example 16. Preparation of 3-Hydroxy-6-(4-methoxyphenethyl)-2,5-dimethylisonicotinic acid (22b)

The compound was synthesized from Compound 21b (65 mg, 0.21 mmol) and 20% aqueous KOH solution (3.0 mL) according to the synthesis procedures of Compound 22a.

Yield 27 mg (43%;) $^1$H NMR (DMSO-d$_6$, 400 MHz) δ 2.41 (3H, s, CH$_3$), 2.43 (3H, s, CH$_3$), 2.71-2.78 (2H, m, CH$_2$), 2.93-3.01 (2H, m, CH$_2$), 3.68 (3H, s, CH$_3$O), 6.80-6.85 (2H, m, phenyl), 7.06-7.12 (2H, m, phenyl); MS (ESI): m/z=302.1 [M+H]; HRMS (ESI) [M+H]$^+$ (C$_{17}$H$_{19}$NO$_4$): calcd. 302.1387, found. 302.1370; Purity 95.2%.

Example 17. Preparation of 3-Hydroxy-6-(4-methoxyphenethyl)-5-methyl-2-propylisonicotinic acid (22c)

The compound was synthesized from Compound 21c (0.12 g, 0.35 mmol) and 20% aqueous KOH solution (3.0 mL) according to the synthesis procedures of Compound 22a.

Yield 54 mg (47%); $^1$H NMR (DMSO-d$_6$, 400 MHz) δ 0.85 (3H, t, J=7.2 Hz, CH$_3$), 1.51-1.61 (2H, m, CH$_2$), 2.46 (3H, s, CH$_3$), 2.62-2.70 (2H, m, CH$_2$), 2.72-2.79 (2H, m, CH$_2$), 2.87-2.97 (2H, m, CH$_2$), 3.00-3.07 (2H, m, CH$_2$), 3.67 (3H, s, CH$_3$O), 6.76-6.81 (2H, m, phenyl), 7.03-7.08 (2H, m, phenyl); $^{13}$C NMR (DMSO-d, 400 MHz) δ 14.1, 15.8, 21.3, 33.0, 34.2, 36.2 55.1, 113.8, 125.9, 129.5, 129.6, 133.8, 145.0, 146.0, 157.6, 172.4; MS (ESI): m/z=329.9 [M+H]; HRMS (ESI) [M+H]$^+$ (C$_9$H$_{23}$NO$_4$): calcd. 330.1700, found. 330.1681; Purity 96.9%.

Example 18. Preparation of 5-Hydroxy-2-[2-(4-methoxyphenyl)ethyl]-3-methyl-6-propyl-pyridine-4-carboxamide (23)

Compound 21c (50 mg, 0.15 mmol) was dissolved in 30% ammonia water (3.0 mL). The reaction mixture was stirred for 12 hours. After completion of the reaction, the thus-prepared mixture was diluted with ethyl acetate and washed with water and brine. The combined organic layers were dried over anhydrous Na$_2$SO$_4$, concentrated under vacuum and then purified by chromatography on silica gel with chloroform/methanol=20:1 to give Compound 23.

Yield 16 mg (32%); $^1$H NMR (DMSO-d&, 400 MHz) δ 0.88 (3H, t, J=7.2 Hz, CH$_3$), 1.54-1.63 (2H, m, CH$_2$), 2.07 (3H, s, CH$_3$), 2.60-266 (2H, m, CH$_2$), 2.77-2.82 (4H, m, 2×CH$_2$), 3.67 (3H, s, CH$_3$O), 6.77-6.82 (2H, m, phenyl), 7.09-7.13 (2H, m, phenyl); MS (ESI): m/z=328.9 [M+H].

Example 19. Preparation of Ethyl 2-(2-(3-phenoxyphenyl)acetamido)pentanoate (24)

The compound was prepared from 3-phenoxyphenylacetic acid (3.8 g, 17 mmol) and L-norvaline ethyl ester (3.1 g, 17 mmol) according to the general procedures for the synthesis of Compounds 10a-k.

Yield 5.2 g (86%); $^1$H NMR (CDCl$_3$, 400 MHz) δ ppm 0.87 (3H, t, J=7.2 Hz, CH$_3$), 1.16-1.28 (2H, m, CH$_2$), 1.24 (3H, t, J=7.6 Hz, CH$_3$), 1.52-1.62 (2H, m, CH$_2$), 1.71-1.82 (2H, m, CH$_2$), 3.54 (3H, t, CH$_3$), 4.11-4.20 (2H, m, CH$_2$), 4.52-4.60 (2H, m, CH$_2$), 5.88-5.95 (1H, m, NH), 6.89-6.95 (2H, m, phenyl), 6.98-7.03 (3H, m, phenyl), 7.07-7.13 (1H, m, phenyl), 7.28-7.36 (3H, m, phenyl); MS (ESI): m/z=355.9 [M+H].

Example 20. Preparation of 5-Ethoxy-2-(3-phenoxybenzyl)-4-propyloxazole (25)

The compound was synthesized from Compound 24 (4.7 g, 13 mmol) and phosphorous pentoxide (7.5 g, 26 mmol) according to the general procedures for the synthesis of Compounds 11a-k.

Yield 4.8 g (97%); $^1$H NMR (CDCl$_3$, 400 MHz) δ ppm 0.91 (3H, t, J=7.2 Hz, CH$_3$), 1.24 (3H, t, J=7.2 Hz, CH$_3$), 1.55-1.63 (2H, m, CH$_2$), 2.31-2.35 (2H, m, CH$_2$), 3.91 (2H, s, CH$_2$), 4.01-4.10 (2H, m, CH$_2$), 6.90-6.94 (1H, m, phenyl), 6.90-6.94 (1H, m, phenyl), 6.96-7.02 (3H, m, phenyl), 7.06-7.13 (1H, m, phenyl), 7.22-7.29 (1H, m, phenyl), 7.29-7.35 (2H, m, phenyl); MS (ESI): m/z=337.9 [M+H].

Example 21. Preparation of Dimethyl 5-hydroxy-2-(3-phenoxybenzyl)-6-propylpyridine-3,4-dicarboxylate (26)

The compound was synthesized from Compound 25 (2.1 g, 6.2 mmol) and dimethyl maleate (2.3 mL, 18 mmol) according to the general procedures for the synthesis of Compound 12a-k.

Yield 1.0 g (37%); $^1$H NMR (CDCl$_3$, 400 MHz) δ ppm 0.94 (3H, t, J=7.6 Hz, CH$_3$), 1.64-1.75 (2H, m, CH$_2$), 2.81-2.87 (2H, m, CH$_2$), 3.78 (3H, s, CH$_3$O), 3.92 (3H, s, CH$_3$O), 4.02 (2H, s, CH$_2$), 6.78-6.83 (2H, m, phenyl), 6.88-6.91 (1H, m, phenyl), 6.94-6.99 (2H, m, phenyl), 7.05-7.10 (1H, m, phenyl), 7.17-7.22 (1H, m, phenyl), 7.27-7.33 (2H, m, phenyl), 10.33 (1H, s, OH); MS (ESI): m/z=436.8 [M+H].

Example 22. Preparation of 5-Hydroxy-2-(3-phenoxybenzyl)-6-propylpyridine-3,4-dicarboxylic acid (27)

The compound was synthesized from Compound 26 (93 mg, 0.21 mmol) and 20% aqueous KOH solution (20 mL) according to the general procedures for the synthesis of Compounds 13a-1.

Yield 33 mg (38%); $^1$H NMR (DMSO-d$_6$, 400 MHz) δ ppm 0.86 (3H, t, J=7.6 Hz, CH$_3$), 1.55-1.65 (2H, m, CH$_2$), 2.71-2.78 (2H, m, CH$_2$), 4.03 (2H, s, CH$_2$), 6.78-6.82 (1H, m, phenyl), 6.87-6.89 (1H, m, phenyl), 6.94-6.98 (3H, m, phenyl), 7.10-7.15 (1H, m, phenyl), 7.23-7.29 (1H, m, phenyl), 7.33-7.39 (2H, m, phenyl); MS (ESI): m/z=407.8 [M+H]; HRMS (ESI) [M+H]$^+$ (C$_{23}$H$_{21}$NO$_6$): calcd. 408.1442, found. 408.1423; Purity 99.0%.

Example 23. Preparation of Methyl 3-hydroxy-5-methyl-6-(3-phenoxybenzyl)-2-propylisonicotinate (28)

The compound was synthesized from Compound 25 (3.6 g, 11 mmol) and methyl crotonate (2.2 mL, 22 mmol) according to the general procedures for the synthesis of Compounds 12a-k.

Yield 0.92 g (22%); $^1$H NMR (CDCl$_3$, 400 MHz) δ ppm 0.96 (3H, t, J=7.6 Hz, CH$_3$), 1.64-1.75 (2H, m, CH$_2$), 2.32 (3H, s, CH$_3$), 2.77-2.84 (2H, m, CH$_2$), 3.95 (3H, s, CH$_3$O), 4.16 (2H, s, CH$_2$), 6.76-6.80 (2H, m, phenyl), 6.84-6.87 (1H, m, phenyl), 6.93-6.97 (2H, m, phenyl), 7.04-7.09 (1H, m, phenyl), 7.15-7.20 (1H, m, phenyl), 7.26-7.32 (2H, m, phenyl), 10.32 (1H, s, OH); $^{13}$C NMR (DMSO-d$_6$, 400 MHz) δ 14.2, 15.5, 21.6, 33.6, 52.8, 116.6, 118.7, 119.1, 123.9, 125.9, 130.4, 131.3, 142.1, 145.8, 148.0, 148.8, 156.9, 157.2, 167.6; MS (ESI): m/z=392.0 [M+H].

Example 24. Preparation of 3-Hydroxy-5-methyl-6-(3-phenoxybenzyl)-2-propylisonicotinic acid (29)

The compound was synthesized from Compound 28 (0.67 g, 1.7 mmol) and 20% aqueous KOH solution (10 mL) according to the general procedures for the synthesis of Compound 22a.

Yield 0.31 g (48%); $^1$H NMR (DMSO-d$_6$, 400 MHz) δ ppm 0.84 (3H, t, J=7.6 Hz, CH), 1.50-1.65 (2H, m, CH$_2$), 2.29 (3H, s, CH$_3$), 2.68-2.82 (2H, m, CH$_2$), 4.12 (2H, s, CH$_2$), 6.77-6.82 (2H, m, phenyl), 6.84-6.87 (1H, m, phenyl), 6.91-6.96 (2H, m, phenyl), 7.06-7.12 (1H, m, phenyl), 7.23-7.28 (1H, m, phenyl), 7.30-7.36 (2H, m, phenyl); $^{13}$C NMR (DMSO-d. 400 MHz) δ 14.1, 16.0, 21.5, 31.4, 117.0, 118.5, 119.2, 123.6, 124.1, 130.4, 130.5, 130.7, 156.8, 157.4, 168.7; MS (ESI): m/z=377.9 [M+H]; HRMS (ESI) [M+H]$^+$ (C$_{23}$H$_{23}$NO$_4$): calcd. 378.1700, found. 378.1674; Purity 95.6%.

Example 25. Preparation of Methyl 3-(benzyloxy)-5-methyl-6-(3-phenoxybenzyl)-2-propylisonicotinate (30)

Benzyl bromide (0.73 mL, 6.1 mmol) was added to a solution of Compound 28 (2.0 g, 5.1 mmol) in dry acetone (15 mL) in the presence of K$_2$CO$_3$ (2.1 g, 15.3 mmol). The reaction mixture was refluxed for 2 hours. After completion of the reaction, the reaction mixture was cooled, neutralized with NH₄Cl, and then extracted twice with dichloromethane. The combined organic layers were dried over anhydrous Na₂SO₄, concentrated under vacuum and then purified by chromatography on silica gel with n-hexane/ethyl acetate=5:1 to give Compound 30.

Yield 1.8 g (73%); $^1$H NMR (CDCl₃, 400 MHz) δ ppm 0.93 (3H, t, J=7.6 Hz, CH₃), 1.65-1.77 (2H, m, CH₂), 2.12 (3H, s, CH₃), 2.73-2.80 (2H, m, CH₂), 3.82 (3H, s, CH₃), 4.13 (2H, s, CH₂), 4.89 (2H, s, CH₂), 6.78-6.86 (2H, m, phenyl), 6.89-6.93 (1H, m, phenyl), 6.94-7.00 (2H, m, phenyl), 7.05-7.10 (1H, m, phenyl), 7.17-7.24 (1H, m, phenyl), 7.27-7.38 (3H, m, phenyl)), 7.38-7.39 (2H, m, phenyl)), 7.39-7.41 (2H, m, phenyl); MS (ESI): m/z=482.2 [M+H].

Example 26. Preparation of (3-(Benzyloxy)-5-methyl-6-(3-phenoxybenzyl)-2-propylpyridin-4-yl)methanol (31)

A suspension of LiAlH₄ (0.23 g, 6.2 mmol) in dry diethyl ether (5 mL) was added dropwise to a solution of Compound 30 (0.50 g, 1.0 mmol) in diethyl ether at 0° C. over 0.5 hour. After completion of the addition, the reaction mixture was stirred at 0° C. under N₂ atmosphere for 1 hour. Unreacted LiAlH₄ was quenched with saturated aqueous NH₄C₁ solution, and the reaction mixture was extracted three times with dichloromethane. The combined organic extracts were dried over anhydrous Na₂SO₄ and the mixture was filtered through a celite pad. The thus-filtered mixture was concentrated under vacuum and purified by chromatography on silica gel with n-hexane/ethyl acetate=2:1 to give Compound 31.

Yield 0.35 g (75%); $^1$H NMR (CD₃OD, 400 MHz) δ ppm 0.88 (3H, t, J=7.6 Hz, CH₃), 1.54-1.65 (2H, m, CH₂), 2.12 (3H, s, CH₃), 2.67-2.75 (2H, m, CH₂), 4.15 (2H, s, CH₂), 4.68 (2H, s, CH₂), 4.90 (2H, s, CH₂), 6.67-6.70 (1H, m, phenyl), 6.75-6.78 (1H, n, phenyl), 6.87-6.92 (3H, m, phenyl), 7.02-7.08 (1H, m, phenyl), 7.19-7.24 (1H, m, phenyl), 7.26-7.41 (5H, m, phenyl), 7.43-7.47 (2H, m, phenyl); MS (ESI): m/z=454.9 [M+H].

Example 27. Preparation of 4-(Hydroxymethyl)-5-methyl-6-(3-phenoxybenzyl)-2-propylpyridin-3-ol (32)

10% Pd/C (15 mg) was added to a solution of Compound 31 (0.10 g, 0.22 mmol) in methanol. The reaction mixture was stirred under H₂ atmosphere for 0.5 hour. After completion of the reaction, the mixture was filtered through a celite pad. The filtrate was concentrated in vacuum and purified by chromatography on silica gel with chloroform/methanol=20:1 to give Compound 32.

Yield 50 mg (62%); $^1$H NMR (CD₃OD, 400 MHz) δ ppm 0.91 (3H, t, J=7.6 Hz, CH₃), 1.52-1.66 (2H, m, CH₂), 2.05 (3H, s, CH₃), 2.62-2.76 (2H, m, CH₂), 3.20-3.25 (2H, m, CH₂), 4.08 (2H, s, CH₂), 4.81 (3H, s, CH₃), 6.62-6.66 (1H, m, phenyl), 6.73-6.77 (1H, m, phenyl), 6.81-6.91 (3H, m, phenyl), 7.02-7.08 (1H, m, phenyl), 7.16-7.22 (1H, m, phenyl), 7.25-7.32 (2H, m, phenyl); MS (ESI): m/z=364.1 [M+H].

Example 28. Preparation of 3-Hydroxy-5-methyl-6-(3-phenoxybenzyl)-2-propylisonicotinaldehyde (33)

Compound 32 (50 mg, 0.14 mmol) was dissolved in dry dichloromethane, and activated manganese dioxide (85 mg, 0.98 mmol) was added to the solution. The reaction mixture was stirred vigorously for 2 hours at room temperature under N₂ atmosphere. After completion of the reaction, the mixture was filtered through a celite pad. The filtrate was concentrated in vacuum and purified by chromatography on silica gel with n-hexane/ethyl acetate=3:1.

Yield 43 mg (85%); $^1$H NMR (CDCl₃, 400 MHz) δ ppm 0.96 (3H, t, J=7.6 Hz, CH₃), 1.64-1.75 (2H, m, CH₂), 2.45 (3H, s, CH₃), 2.77-2.86 (2H, m, CH₂), 4.16 (2H, s, CH₂), 6.77-6.82 (2H, m, phenyl), 6.85-6.91 (1H, m, phenyl), 6.92-6.95 (1H, m, phenyl), 6.95-6.98 (1H, m, phenyl), 7.04-7.10 (1H, m, phenyl), 7.15-7.23 (1H, m, phenyl), 7.26-7.34 (2H, m, phenyl), 10.42 (1H, s, CHO); MS (ESI): m/z=361.7 [M+H].

Example 29. Preparation of Ethyl (E)-3-(3-hydroxy-5-methyl-6-(3-phenoxybenzyl)-2-propylpyridin-4-yl)acrylate (34)

Triethyl phosphonoacetate (24 μL, 0.12 mmol) was added dropwise to a suspension of NaH (5.0 mg, 0.48 mmol, 60% oil suspension) in anhydrous THF. After stirring the suspension for 5 minutes, anhydrous THE solution, in which Compound 33 (40 mg, 0.11 mmol) was dissolved, was added thereto. The reaction mixture was stirred for 1 hour. After completion of the reaction, the thus-prepared mixture was diluted with dichloromethane and washed with water and brine. The organic layer was dried over anhydrous Na₂SO₄, concentrated under vacuum and purified by chromatography on silica gel with n-hexane/ethyl acetate=3:1.

Yield 33 mg (70%); $^1$H NMR (CDCl₃, 400 MHz) δ ppm 0.93 (3H, t, J=7.6 Hz, CH₃), 1.30 (3H, t, J=7.2 Hz, CH₃), 1.69 (2H, q, J=7.6 Hz, CH₂), 2.13 (3H, s, CH₃), 2.71-2.79 (2H, m, CH₂), 4.11 (2H, s, CH₂), 4.27 (2H, q, J=7.2 Hz, CH₂), 6.38 (1H, d, J=16.4 Hz, =CH), 6.75-6.80 (2H, m, phenyl), 6.80-6.82 (1H, m, phenyl), 6.92-6.98 (2H, m, phenyl), 7.02-7.09 (1H, m, phenyl), 7.14-7.21 (1H, m, phenyl), 7.26-7.33 (2H, m, phenyl), 7.64 (1H, d, J=16.4 Hz, =CH); MS (ESI): m/z=432.0 [M+H].

Example 30. Preparation of (E)-3-(3-Hydroxy-5-methyl-6-(3-phenoxybenzyl)-2-propylpyridin-4-yl)acrylic acid (35)

The compound was synthesized from Compound 34 (35 mg, 0.081 mmol) and 20% aqueous KOH solution (7 mL) according to the general procedures for the synthesis of Compound 22a.

Yield 12 mg (37%); $^1$H NMR (CD₃OD, 400 MHz) δ ppm 0.90 (3H, t, J=7.6 Hz, CH₃), 1.56 (2H, q, J=7.6 Hz, CH₂), 2.11 (3H, s, CH₃), 2.70-2.77 (2H, m, CH₂), 4.09 (2H, s, CH₂), 6.61-6.78 (3H, m, phenyl & =CH), 6.86-6.92 (3H, m, phenyl), 7.04-7.08 (1H, m, phenyl), 7.14-7.24 (1H, m, phenyl), 7.26-7.31 (2H, m, phenyl), 7.56 (1H, d, J=16.4 Hz, =CH); MS (ESI): m/z=403.6 [M+H].

Example 31. Preparation of Ethyl 3-(3-hydroxy-5-methyl-6-(3-phenoxybenzyl)-2-propylpyridin-4-yl)propanoate (36)

The compound was synthesized from Compound 34 (0.10 g, 0.23 mmol) and 10% Pd/C (15 mg) according to the synthesis procedures of Compound 32.

Yield 59 mg (59%); $^1$H NMR (CDCl₃, 400 MHz) δ ppm 0.96 (3H, t, J=7.2 Hz, CH₃), 1.23 (3H, t, J=7.2 Hz, CH₃), 1.61-1.72 (2H, m, CH₂), 2.06 (3H, s, CH₃), 2.62-2.70 (2H, m, CH₂), 2.73-2.82 (2H, m, CH₂), 2.86-2.92 (2H, m, CH₂), 4.09 (2H, s, CH₂), 4.14 (2H, q, J=7.2 Hz, CH₂), 6.74-6.84

(2H, m, phenyl), 6.92-6.97 (2H, m, phenyl), 7.03-7.09 (1H, m, phenyl), 7.14-7.20 (1H, m, phenyl), 7.26-7.28 (1H, m, phenyl), 7.28-7.32 (2H, m, phenyl); MS (ESI): m/z=434.0 [M+H].

Example 32. Preparation of 3-(3-Hydroxy-5-methyl-6-(3-phenoxybenzyl)-2-propylpyridin-4-yl) propanoic acid (37)

The compound was synthesized from Compound 36 (59 mg, 0.143 mmol) and 20% aqueous KOH solution (7 mL) according to the general procedures for the synthesis of Compound 22a.

Yield 52 mg (94%); $^1$H NMR (CDCl$_3$, 400 MHz) δ ppm 0.93 (3H, t, J=7.6 Hz, CH$_3$), 1.59-1.70 (2H, m, CH$_2$), 2.17 (3H, s, CH$_3$), 2.51-2.59 (2H, m, CH$_2$), 2.80-2.90 (2H, m, CH$_2$), 2.96-3.06 (2H, m, CH$_2$), 4.21 (2H, s, CH$_2$), 6.55-6.60 (1H, m, phenyl), 6.79-6.84 (2H, m, phenyl), 6.88-6.93 (2H, m, phenyl), 7.06-7.12 (1H, m, phenyl), 7.23-7.34 (3H, m, phenyl); $^{13}$C NMR (DMSO-d$_6$, 400 MHz) δ 14.3, 14.5, 21.9, 22.2, 33.0, 33.7, 116.5, 118.7, 119.1, 123.9, 130.3, 130.5, 142.6, 146.1, 156.9, 157.1, 174.7; MS (ESI): m/z=406.1 [M+H]; HRMS (ESI) [M+H]$^+$ (C$_{23}$H$_{27}$NO$_4$): calcd. 406.2013, found. 406.1990; Purity 97.8%.

Example 33. Preparation of 3-Hydroxy-5-methyl-6-(3-phenoxybenzyl)-2-propylisonicotinonitrile (38)

The compound was synthesized from Compound 25 (0.50 g, 1.5 mmol) and methyl crotononitrile (0.24 mL, 3.0 mmol) according to the general procedures for the synthesis of Compounds 12a-k.

Yield 0.36 g (67%); $^1$H NMR (CDCl$_3$, 400 MHz) δ ppm 0.91 (3H, t, J=7.6 Hz, CH$_3$), 1.64-1.74 (2H, m, CH$_2$), 2.34 (3H, s, CH$_3$), 2.74-2.81 (2H, m, CH$_2$), 4.09 (2H, m, CH$_2$), 6.78-6.82 (2H, m, phenyl), 6.85-6.88 (1H, m, phenyl), 6.93-6.98 (2H, m, phenyl), 7.06-7.12 (1H, m, phenyl), 7.17-7.22 (1H, m, phenyl), 7.27-7.33 (2H, m, phenyl); MS (ESI): m/z=359.1 [M+H].

Example 34. Preparation of 3-(Benzyloxy)-5-methyl-6-(3-phenoxybenzyl)-2-propylisonicotinonitrile (39)

The compound was synthesized from Compound 38 (0.20 g, 0.56 mmol) and benzyl bromide (80 μL, 0.67 mmol) according to the synthesis procedures of Compound 30.

Yield 0.025 g (99%); $^1$H NMR (CDCl$_3$, 400 MHz) δ ppm 0.90 (3H, t, J=7.6 Hz, CH$_3$), 1.60-1.70 (2H, m, CH$_2$), 2.39 (3H, s, CH$_3$), 2.69-2.77 (2H, m, CH$_2$), 4.14 (2H, s, CH$_2$), 5.08 (2H, s, CH$_2$), 6.79-6.85 (2H, m, phenyl), 6.89-6.90 (1H, m, phenyl), 6.94-6.99 (2H, m, phenyl), 7.06-7.11 (1H, m, phenyl), 7.18-7.24 (1H, m, phenyl), 7.28-7.34 (2H, m, phenyl), 7.36-7.44 (3H, m, phenyl), 7.46-7.51 (2H, m, phenyl); MS (ESI): m/z=449.1 [M+H].

Example 35. Preparation of (3-(Cyclohexa-2,4-dien-1-ylmethoxy)-5-methyl-6-(3-phenoxybenzyl)-2-propylpyridin-4-yl) methanamine (40)

The compound was synthesized from Compound 39 (51 mg, 0.11 mmol) and LiAlH$_4$ (0.23 g, 6.2 mmol) according to the synthesis procedures of Compound 31.

Yield 33 mg (66%); $^1$H NMR (CDCl$_3$, 400 MHz) δ ppm 0.94 (3H, t, J=7.6 Hz, CH$_3$), 1.68-1.79 (2H, m, CH$_2$), 2.19 (3H, s, CH$_3$), 2.74-2.82 (2H, m, CH$_2$), 3.83 (2H, s, CH$_2$), 4.14 (2H, s, CH$_2$), 4.86 (2H, s, CH$_2$), 6.78-6.84 (2H, m, phenyl), 6.90-6.98 (3H, m, phenyl), 7.04-7.09 (1H, m, phenyl), 7.16-7.22 (1H, m, phenyl), 7.26-7.33 (2H, m, phenyl), 7.35-7.47 (5H, m, phenyl); MS (ESI): m/z=455.2 [M+H].

Example 36. Preparation of 4-(Aminomethyl)-5-methyl-6-(3-phenoxybenzyl)-2-propylpyridin-3-ol (41)

The compound was synthesized from Compound 40 (0.12 g, 0.26 mmol) and 10% Pd/C (15 mg) according to the synthesis procedures of Compound 32.

Yield 67 mg (71%); $^1$H NMR (CD$_3$OD, 400 MHz) δ ppm 0.91 (3H, t, J=7.2 Hz, CH$_3$), 1.54-1.65 (2H, m, CH$_2$), 2.03 (3H, s, CH$_3$), 2.64-2.75 (2H, m, CH$_2$), 4.03-4.09 (4H, m, 2×CH$_2$), 6.62-6.66 (2H, m, phenyl), 6.74-6.77 (1H, m, phenyl), 6.82-6.90 (2H, m, phenyl), 7.04-7.08 (1H, m, phenyl), 7.16-7.21 (1H, m, phenyl), 7.30-7.36 (2H, m, phenyl); MS (ESI): m/z=363.06 [M+H]; HRMS (ESI) [M+H]$^+$ (C$_{23}$H$_{26}$N$_2$O$_2$): calcd. 363.2067, found. 363.2043; Purity 96.6%.

Example 37. Preparation of N-((3-(Benzyloxy)-5-methyl-6-(3-phenoxybenzyl)-2-propylpyridin-4-yl) methyl)methanesulfonamide (42)

Anhydrous dichloromethane (3 mL) solution including compound 40 (33 mg, 0.073 mmol) and triethylamine (12 μL, 0.087 mmol) was cooled to 0° C. and methane sulfonyl chloride (7 μL, 0.087 mmol) was added dropwise thereto. The reaction mixture was stirred at room temperature for 1 hour, and subsequently, the mixture was diluted with ethyl acetate and washed with brine. The organic layer was dried over anhydrous Na$_2$SO$_4$, concentrated under vacuum and then purified by chromatography on silica gel with chloroform/methanol=20:1 to give Compound 42.

Yield 26 mg (67%); $^1$H NMR (CDCl$_3$, 400 MHz) δ ppm 0.95 (3H, t, J=7.3 Hz, CH$_3$), 1.70-1.80 (2H, m, CH$_2$), 2.19 (3H, s, CH$_3$), 2.62 (3H, s, CH$_3$), 2.79-2.85 (2H, m, CH$_2$), 4.13-4.17 (4H, m, 2×CH$_2$), 4.86-4.90 (2H, m, CH$_2$), 6.75-6.83 (2H, m, phenyl), 6.88-6.92 (1H, m, phenyl), 6.93-6.98 (2H, m, phenyl), 7.05-7.10 (1H, m, phenyl), 7.17-7.23 (1H, m, phenyl), 7.27-7.33 (2H, m, phenyl), 7.37-7.44 (3H, m, phenyl), 7.37-7.44 (2H, m, phenyl); MS (ESI): m/z=531.1 [M+H].

Example 38. Preparation of N-((3-Hydroxy-5-methyl-6-(3-phenoxybenzyl)-2-propylpyridin-4-yl) methyl) methanesulfonamide (43)

The compound was synthesized from Compound 42 (21 mg, 0.040 mmol) and 10% Pd/C (5.0 mg) according to the synthesis procedures of Compound 32.

Yield 11 mg (62%); $^1$H NMR (CDCl$_3$, 400 MHz) δ ppm 0.96 (3H, t, J=7.6 Hz, CH$_3$), 1.63-1.74 (2H, m, CH$_2$), 2.19 (3H, s, CH$_3$), 2.72-2.77 (2H, m, CH$_2$), 2.82 (3H, s, CH$_3$), 4.12 (2H, s, CH$_2$), 4.33 (2H, s, CH$_2$), 6.74-6.81 (2H, m, phenyl), 6.85-6.88 (1H, m, phenyl), 6.92-6.96 (2H, m, phenyl), 7.04-7.10 (1H, m, phenyl), 7.16-7.21 (1H, m, phenyl), 7.26-7.32 (2H, m, phenyl); $^{13}$C NMR (DMSO-d$_6$, 400 MHz) δ 14.4, 14.6, 21.8, 34.2, 38.3, 41.4, 116.4, 118.9, 119.1, 123.9, 124.0, 129.2, 130.2, 130.5, 131.7, 142.9, 147.0, 148.0, 157.0, 157.1; MS (ESI): m/z=441.0 [M+H]; HRMS (ESI) [M+H]$^+$ (C$_{24}$H$_{28}$N$_2$O$_4$S): calcd. 441.1843, found. 441.1818; Purity 98.3%.

Example 39. Preparation of 3-(Benzyloxy)-5-methyl-6-(3-phenoxylbenzyl)-2-propylisonicotinic acid (44)

20% aqueous KOH solution was added to a solution of Compound 30 (120.8 mg, 0.25 mmol) in 1,4-dioxane (1 ml) and methanol (1 ml). The reaction mixture was stirred vigorously at 50° C. for two days. After cooling to room temperature, the reaction mixture was diluted with brine and extracted three times with EA. The organic layer was dried over anhydrous $Na_2SO_4$. The mixture was filtered and concentrated under vacuum and then purified by chromatography on silica gel with chloroform:methanol=10:1, as an eluent, to give Compound 44 (74.4 mg).

Yield 63%; $^1$H NMR (DMSO-$d_6$, 400 MHz) δ 0.82 (3H, t, J=7.3 Hz, $CH_3$), 1.50-1.59 (2H, m, J=7.0 Hz, 7.3 Hz, 7.9 Hz, $CH_2$), 2.07 (3H, s, $CH_3$), 2.57 (2H, t, J=7.3 Hz, 7.9 Hz, $CH_2$), 4.00 (2H, s, $CH_2$), 4.99 (2H, s, $CH_2$), 6.80 (2H, d, J=7.9 Hz, phenyl), 6.85 (1H, s, phenyl), 6.98 (2H, d, J=7.9 Hz, phenyl), 7.12 (1H, t, J=7.3 Hz, 7.6 Hz, phenyl), 7.25-7.33 (2H, m, J=7.6 Hz, phenyl), 7.37 (4H, t, J=7.3 Hz, phenyl), 7.44 (2H, d, J=7.6 Hz, phenyl); MS (ESI): m/z=468.1 [M+H].

Example 40. General Procedures for Preparation of Compounds 45a-j $NaHCO_3$ (3.0 equiv) was added to a solution of Compound 44 (1.0 equiv) in 20% DMF, and the mixture was stirred at room temperature for 30 minutes. Various alkyl halides (3.0 equiv) were added to the reaction mixture and stirred at 50° C. overnight. After cooling to room temperature, the reaction mixture was diluted with brine and extracted three times with DCM. The organic layer was dried over anhydrous $Na_2SO_4$. After filtration, the mixture was concentrated under vacuum and then purified by silica gel chromatography using n-hexane:EA=5:1, as an eluent, to give Compounds 45a-j.

40-1. Preparation of Phenethyl 3-(benzyloxy)-5-methyl-6-(3-phenoxybenzyl)-2-propylisonicotinate (45a)

Compound 45a (19.1 mg) was obtained by the reaction between Compound 44 (20.3 mg, 0.043 mmol, 1.0 equiv) and (2-bromoethyl)benzene (24.1 mg, 0.130 mmol, 3.0 equiv) according to the general procedures for the synthesis of Compounds 45a-j described above.

Yield 77%; $^1$H NMR (CDCl$_3$, 400 MHz) δ 0.94 (3H, t, J=7.3 Hz, $CH_3$), 1.69-1.75 (2H, m, J=7.6 Hz, $CH_2$), 2.00 (3H, s, $CH_3$), 2.77 (2H, t, J=7.6 Hz, 7.9 Hz, $CH_2$), 2.94 (2H, t, J=7.0 Hz, 7.3 Hz, $CH_2$), 4.12 (2H, s, $CH_2$), 4.64 (2H, t, J=7.0 Hz, 7.3 Hz, $CH_2$), 4.88 (2H, s, $CH_2$), 6.83 (1H, d, J=7.9 Hz, phenyl), 6.86 (1H, s, phenyl), 6.91 (1 H, d, J=7.6 Hz, phenyl), 6.98 (2H, d, J=7.9 Hz, phenyl), 7.08 (1H, t, J=7.3 Hz, 7.6 Hz, phenyl), 7.16-7.25 (5H, br, phenyl), 7.27-7.41 (8H, br, phenyl); MS (MALDI-TOF): m/z=571.5 [M+H].

40-2. Preparation of Octyl 3-(benzyloxy)-5-methyl-6-(3-phenoxybenzyl)-2-propylisonicotinate (45b)

Compound 45b (32.7 mg) was obtained by the reaction between Compound 44 (30.0 mg, 0.064 mmol, 1.0 equiv) and 1-bromooctane (24.1 mg, 0.130 mmol, 3.0 equiv) according to the general procedures for the synthesis of Compounds 45a-j described above.

Yield 77%; $^1$H NMR (CDCl$_3$, 400 MHz) δ 0.94 (3H, t, J=7.3 Hz, $CH_3$), 1.69-1.75 (2H, m, J=7.6 Hz, $CH_2$), 2.00 (3H, s, $CH_3$), 2.77 (2H, t, J=7.6 Hz, 7.9 Hz, $CH_2$), 2.94 (2H, t, J=7.0 Hz, 7.3 Hz, $CH_2$), 4.12 (2H, s, $CH_2$), 4.64 (2H, t, J=7.0 Hz, 7.3 Hz, $CH_2$), 4.88 (2H, s, $CH_2$), 6.83 (1H, d, J=7.9 Hz, phenyl), 6.86 (1H, s, phenyl), 6.91 (1H, d, J=7.6 Hz, phenyl), 6.98 (2H, d, J=7.9 Hz, phenyl), 7.08 (1H, t, J=7.3 Hz, 7.6 Hz, phenyl), 7.16-7.25 (5H, br, phenyl), 7.27-7.41 (8H, br, phenyl); MS (MALDI-TOF): m/z=571.5 [M+H].

40-3. Preparation of 2-phthalimidoethyl 3-(benzyloxy)-5-methyl-6-(3-phenoxybenzyl)-2-propylisonicotinate (45c)

Compound 45c (26.0 mg) was obtained by the reaction between Compound 44 (30.0 mg, 0.064 mmol, 1.0 equiv) and N-(2-bromoethyl)phthalimide (48.8 mg, 0.192 mmol, 3.0 equiv) according to the general procedures for the synthesis of Compounds 45a-j described above.

Yield=63%; $^1$H NMR (CDCl$_3$, 400 MHz) δ 0.91 (3H, t, J=7.3 Hz, $CH_3$), 1.65-1.71 (2H, m, J=7.6 Hz, $CH_2$), 2.09 (3H, s, $CH_3$), 2.72 (2H, t, J=7.6 Hz, 7.9 Hz, $CH_2$), 4.00 (2H, t, J=5.5 Hz, $CH_2$), 4.11 (2H, s, $CH_2$), 4.49 (2H, t, J=5.5 Hz, 5.8 Hz, $CH_2$), 4.85 (2H, s, $CH_2$), 6.82 (1H, d, J=8.2 Hz, phenyl), 6.85 (1H, s, phenyl), 6.89 (1H, d, J=7.6 Hz, phenyl), 6.98 (2H, d, J=8.0 Hz, phenyl), 7.08 (1H, t, J=7.3 Hz, phenyl), 7.21 (1H, d, J=7.6 Hz, 7.9 Hz, phenyl), 7.30-7.38 (7H, br, phenyl), 7.67-7.71 (2H, m, J=2.4 Hz, 3.0 Hz, phthalimidyl), 7.76-7.80 (2H, m, J=2.4 Hz, 3.0 Hz, phthalimidyl); MS (ESI): m/z=640.9 [M+H].

40-4. Preparation of 4-phthalimidobutyl 3-(benzyloxy)-5-methyl-6-(3-phenoxybenzyl)-2-propylisonicotinate (45d)

Compound 45d (38.6 mg) was obtained by the reaction between Compound 44 (30.0 mg, 0.064 mmol, 1.0 equiv) and N-(4-bromobutyl)phthalimide (4.2 mg, 0.192 mmol, 3.0 equiv) according to the general procedures for the synthesis of Compounds 45a-j described above.

Yield=89%; $^1$H NMR (CDCl$_3$, 400 MHz) δ 0.94 (3H, t, J=7.3 Hz, $CH_3$), 1.67-1.74 (6H, br, J=7.6 Hz, 7.9 Hz, $CH_2$), 2.12 (3H, s, $CH_3$), 2.76 (2H, t, J=7.6 Hz, 7.9 Hz, $CH_2$), 3.63 (2H, t, J=6.4 Hz, $CH_2$), 4.13 (2H, s, $CH_2$), 4.27 (2H, t, J=5.8 Hz, $CH_2$), 4.90 (2H, s, $CH_2$), 6.82 (1H, d, J=8.2 Hz, phenyl), 6.87 (1H, s, phenyl), 6.92 (1H, d, J=7.6 Hz, phenyl), 6.98 (2H, d, J=7.6 Hz, phenyl), 7.08 (1H, t, J=7.3 Hz, phenyl), 7.21 (1H, d, J=7.6 Hz, 7.9 Hz, phenyl), 7.30-7.41 (7H, br, phenyl), 7.70-7.73 (2H, m, J=2.1 Hz, 3.1 Hz, 3.4 Hz, phthalimidyl), 7.81-7.84 (2H, m, J=3.1 Hz, phthalimidyl); MS (ESI): m/z=669.0 [M+H].

40-5. Preparation of 2-(pyrrolidin-1-yl)ethyl 3-(benzyloxy)-5-methyl-6-(3-phenoxybenzyl)-2-propylisonicotinate (45e)

Compound 45e (26.7 mg) was obtained by the reaction between Compound 44 (30.0 mg, 0.064 mmol, 1.0 equiv) and N-(2-chloroethyl)pyrrolidine hydrochloride (32.7 mg, 0.192 mmol, 3.0 equiv) according to the general procedures for the synthesis of Compounds 45a-j described above.

Yield=74%; $^1$H NMR (CDCl$_3$, 400 MHz) δ 0.94 (3H, t, J=7.3 Hz, 7.6 Hz, $CH_3$), 1.65-1.74 (6H, br, $CH_2$), 2.15 (3H, s, $CH_3$), 2.48 (3H, s, $CH_3$), 2.71-2.78 (4H, br, $CH_2$), 4.13 (2H, s, $CH_2$), 4.39 (2H, t, J=6.1 Hz, $CH_2$), 4.92 (2H, s, $CH_2$), 6.82 (1H, d, J=8.2 Hz, phenyl), 6.87 (1H, s, phenyl), 6.92

(1H, d, J=7.6 Hz, phenyl), 6.98 (2H, d, J=7.6 Hz, phenyl), 7.09 (1H, t, J=7.3 Hz, phenyl), 7.22 (1H, d, J=7.6 Hz, phenyl), 7.30-7.43 (7H, br, phenyl); MS (ESI): m/z=565.0 [M+H].

40-6. Preparation of Isopropyl 3-(benzyloxy)-5-methyl-6-(3-phenoxybenzyl)-2-propylisonicotinate (45f)

Compound 45f was obtained by the reaction between Compound 44 (30.0 mg, 0.064 mmol, 1.0 equiv) and 2-iodopropane (19.2 μl, 0.192 mmol) according to the general procedures for the synthesis of Compounds 45a-j described above.

Yield 22.8 mg (70%); $^1$H NMR (CDCl$_3$, 400 MHz) δ ppm 7.41-7.43 (2H, m, phenyl), 7.35-7.39 (2H, m, phenyl), 7.29-7.34 (3H, m, phenyl), 7.21 (1H, t, J=7.8 Hz, phenyl), 7.06-7.10 (1H, m, phenyl), 6.97-6.99 (2H, m, phenyl), 6.93 (1H, d, J=6.9 Hz, phenyl), 6.81-6.83 (1H, m, phenyl), 5.24-4.27 (1H, m, J=6.4 Hz, CH), 4.93 (2H, s, CH$_2$), 4.14 (2H, s, CH$_2$), 2.73-2.77 (2H, m, CH$_2$), 2.14 (3H, s, CH$_3$), 1.28 (6H, d, J=6 Hz, CH$_3$), 0.93 (3H, m, CH$_3$); MS (ESI): m/z=509.5 [M+H].

40-7. Preparation of Pentan-3-yl 3-(benzyloxy)-5-methyl-6-(3-phenoxybenzyl)-2-propylisonicotinate (45g)

Compound 45g was obtained by the reaction between Compound 44 (30.0 mg, 0.064 mmol, 1.0 equiv) and 3-bromopentane (24.0 μl, 0.192 mmol) according to the general procedures for the synthesis of Compounds 45a-j described above.

Yield 12.2 mg (35%); $^1$H NMR (CDCl$_3$, 400 MHz) δ ppm 7.39-7.42 (3H, m, phenyl), 7.36-7.38 (1H, m, phenyl), 7.33-7.36 (1H, m, phenyl), 7.29-7.31 (2H, m, phenyl), 7.22 (1H, t, J=7.9 Hz, phenyl), 7.06-7.10 (1H, m, J=7.6 Hz, phenyl), 6.97-6.99 (2H, m, phenyl), 6.93-6.94 (1H, m, J=7.6 Hz, phenyl), 6.88 (1H, t, J=2.0 Hz, phenyl), 6.81-6.84 (1H, m, phenyl), 4.96-5.02 (1H, m, J=6.4 Hz, CH), 4.92 (2H, s, CH$_2$), 4.14 (2H, s, CH$_2$), 2.73-2.77 (2H, m, CH$_2$), 2.16 (3H, s, CH$_3$), 1.69-1.74 (2H, m, J=8.0 Hz, CH$_2$), 1.58-1.65 (4H, m, J=6.4 Hz, CH$_2$), 0.93 (3H, t, J=7.6 Hz, CH$_3$), 0.87 (6H, t, J=7.2 Hz, CH$_3$); MS (ESI): m/z=537.2 [M+H].

40-8. Preparation of Cyclopentyl 3-(benzyloxy)-5-methyl-6-(3-phenoxybenzyl)-2-propylisonicotinate (45h)

Compound 45h was obtained by the reaction between Compound 44 (30.0 mg, 0.064 mmol, 1.0 equiv) and bromocyclopentane (41.1 μl, 0.384 mmol, 6.0 equiv) according to the general procedures for the synthesis of Compounds 45a-j described above.

Yield 20.2 mg (59%); $^1$H NMR (CDCl$_3$, 400 MHz) δ ppm 7.39-7.43 (3H, m, phenyl), 7.33-7.37 (2H, m, phenyl), 7.30-7.33 (2H, m, phenyl), 7.22 (1H, t, J=8 Hz, phenyl), 7.07-7.10 (1H, m, J=7.2 Hz, phenyl), 6.97-7.00 (2H, m, phenyl), 6.92-6.94 (1H, m, phenyl), 6.88 (1H, t, J=1.6 Hz, phenyl), 6.81-6.84 (1H, m, phenyl), 5.36-5.41 (1H, m, J=3.2 Hz, CH), 4.92 (2H, s, CH$_2$), 4.13 (2H, s, CH$_2$), 2.74-2.77 (2H, m, J=8 Hz, CH$_2$), 2.14 (3H, s, CH$_3$), 1.85-1.92 (4H, m, CH$_2$), 1.65-1.76 (4H, m, CH$_2$), 1.25 (2H, s, CH$_2$), 0.94 (3H, t, J=7.2 Hz, CH$_3$); MS (ESI): m/z=535.1 [M+H].

40-9. Preparation of Tetrahydrofuran-3-yl 3-(benzyloxy)-5-methyl-6-(3-phenoxybenzyl)-2-propylisonicotinate (45i)

Compound 45i was obtained by the reaction between Compound 44 (30.0 mg, 0.064 mmol, 1.0 equiv) and 3-bromohydrofuran (36.2 μl, 0.384 mmol, 6.0 equiv) according to the general procedures for the synthesis of Compounds 45a-j described above.

Yield 11.7 mg (89%); $^1$H NMR (CDCl$_3$, 400 MHz) δ ppm 7.39-7.41 (3H, m, phenyl), 7.36 (1H, t, J=2 Hz, phenyl), 7.33-7.35 (1H, m, phenyl), 7.31-7.32 (1H, m, phenyl), 7.30 (1H, t, J=2 Hz, phenyl), 7.22 (1H, t, J=8 Hz, phenyl), 7.07-7.11 (1H, m, J=7.6 Hz, phenyl), 6.97-7.00 (2H, m, phenyl), 6.91-6.94 (1H, m, phenyl), 6.87 (1H, t, J=2 Hz, phenyl), 6.81-6.84 (1H, m, phenyl), 5.44-5.48 (1H, m, J=4.4 Hz, CH), 4.92 (2H, s, CH$_2$), 4.14 (2H, s, CH$_2$), 3.84-3.92 (2H, m, CH$_2$), 3.77-3.82 (2H, m, CH$_2$), 2.75-2.79 (2H, m, J=7.6 Hz, 2 Hz, CH$_2$), 2.14 (3H, s, CH$_3$), 1.96-2.03 (2H, br, CH$_2$), 1.68-1.78 (2H, m, J=1.6 Hz, 8 Hz, CH$_2$), 0.943 (3H, t, J=7.2 Hz, CH$_3$); MS (ESI): m/z=537.6 [M+H].

40-10. Preparation of 1-(Tert-butoxycarbonyl)piperidin-4-yl 3-(benzyloxy)-5-methyl-6-(3-phenoxybenzyl)-2-propylisonicotinate (45j)

Compound 45j was obtained by the reaction between Compound 44 (30.0 mg, 0.064 mmol, 1.0 equiv) and bromocyclopentane (101.4 mg, 0.384 mmol, 6.0 equiv) according to the general procedures for the synthesis of Compounds 45a-j described above.

Yield 27.8 mg (67%); $^1$H NMR (CDCl$_3$, 400 MHz) δ ppm 7.39-7.41 (4H, m, phenyl), 7.35-7.37 (1H, m, phenyl), 7.30-7.34 (2H, m, phenyl), 7.22 (1H, t, J=8 Hz, phenyl), 7.07-7.11 (1H, m, J=1.2 Hz, 7.6 Hz, phenyl), 6.97-6.99 (2H, m, J=1.2 Hz, 7.6 Hz, phenyl), 6.92-6.95 (1H, m, J=1.2 Hz, 7.6 Hz, phenyl), 6.87-6.88 (1H, m, J=1.6 Hz, phenyl), 6.81-6.84 (1H, m, J=0.8 Hz, 7.6 Hz, phenyl), 5.11-5.16 (1H, m, J=3.6 Hz, CH), 4.91 (2H, s, CH$_2$), 4.14 (2H, s, CH$_2$), 3.60-3.70 (2H, br, CH$_2$), 3.13-3.20 (2H, m, J=3.6 Hz, 9.2 Hz, CH$_2$), 2.75-2.79 (2H, m, J=2 Hz, 8 Hz, CH$_2$), 2.14 (3H, s, CH$_3$), 1.79-1.88 (2H, br, CH$_2$), 1.72-1.76 (2H, m, J=1.6 Hz, 7.6 Hz, CH$_2$), 1.57-1.58 (2H, d, J=5.2 Hz, CH$_2$), 1.44-1.46 (9H, m, CH$_3$), 0.95 (3H, t, J=7.2 Hz, CH$_3$); MS (ESI): m/z=649.5 [M+H].

Example 41. General Procedures for Preparation of Compounds 46a-j

Pd/C was added to a solution of Compounds 45a-j (1.0 equiv) in DCM/methanol (1:3) mixed solution, and the mixture was stirred at room temperature for 30 minutes under H$_2$ atmosphere (1 atm). After filtration through a celite filter, the mixture was concentrated under vacuum and purified by silica gel column chromatography using n-hexane:EA=3:1, as an eluent, to give Compounds 46a-j.

41-1. Preparation of Phenethyl 3-hydroxy-5-methyl-6-(3-phenoxybenzyl)-2-propylisonicotinate (46a)

Compound 46a (3.0 mg) was obtained by reacting Compound 45a (16.1 mg, 0.028 mmol) according to the general procedures for the synthesis of Compounds 46a-j described above.

Yield 22%; $^1$H NMR (CDCl$_3$, 400 MHz) δ 0.96 (3H, t, J=7.3 Hz, CH$_3$), 1.56 (3H, s, CH$_3$), 1.69-1.75 (2H, m, J=7.6 Hz, CH$_2$), 2.21 (3H, s, CH$_3$), 2.80 (2H, t, J=7.6 Hz, 7.9 Hz, CH$_2$), 3.08 (2H, t, J=7.0 Hz, CH$_2$), 4.14 (2H, s, CH$_2$), 4.62 (2H, t, J=7.0 Hz, CH$_2$), 6.79 (2H, s, phenyl), 6.85 (1H, d, J=7.6 Hz, phenyl), 6.96 (2H, d, J=8.5 Hz, phenyl), 7.08 (1H, t, J=7.3 Hz, 7.6 Hz, phenyl), 7.16-7.25 (5H, br, phenyl), 7.27-7.41 (8H, br, phenyl); MS (ESI): m/z=481.9 [M+H].

41-2. Preparation of Octyl 3-hydroxy-5-methyl-6-(3-phenoxybenzyl)-2-propylisonicotinate (46b)

Compound 46b (15.4 mg) was obtained by reacting Compound 45b (32.7 mg, 0.056 mmol) according to the general procedures for the synthesis of Compounds 46a-j described above.

Yield 56%; $^1$H NMR (CDCl$_3$, 400 MHz) δ 0.87 (3H, t, J=6.7 Hz, 7.0 Hz, CH$_3$), 0.96 (3H, t, J=7.3 Hz, 7.6 Hz, CH$_3$), 1.23-1.42 (10H, br, CH$_2$), 1.66-1.77 (4H, m, J=7.0 Hz, 7.6 Hz, 7.9 Hz, CH$_2$), 2.35 (3H, s, CH$_3$), 2.81 (2H, t, J=6.7 Hz, 7.0 Hz, CH$_2$), 4.16 (2H, s, CH$_2$), 4.36 (2H, t, J=6.7 Hz, CH$_2$), 4.90 (2H, s, CH$_2$), 6.79 (2H, d, J=8.0 Hz, phenyl), 6.95 (2H, d, J=7.3 Hz, phenyl), 7.06 (1H, t, J=7.3 Hz, phenyl), 7.18 (1H, t, J=7.6 Hz, 7.9 Hz, phenyl), 7.29 (1H, t, J=7.3 Hz, phenyl); MS (MALDI-TOF): m/z=489.4 [M+H].

41-3. Preparation of 2-phthalimidoethyl 3-hydroxy-5-methyl-6-(3-phenoxybenzyl)-2-propylisonicotinate (46c)

Compound 46c (17.6 mg) was obtained by reacting Compound 45c (21.0 mg, 0.033 mmol) according to the general procedures for the synthesis of Compounds 46a-j described above.

Yield=98%; $^1$H NMR (CDCl$_3$, 400 MHz) δ 0.95 (3H, t, J=7.3 Hz, CH$_3$), 1.65-1.71 (2H, m, J=7.3 Hz, 7.6 Hz, 7.9 Hz, CH$_2$), 2.25 (3H, s, CH$_3$), 2.80 (2H, t, J=7.6 Hz, CH$_2$), 4.13 (4H, br, CH$_2$), 4.64 (2H, t, J=4.8 Hz, 5.8 Hz, CH$_2$), 6.78 (2H, s, phenyl), 6.84 (1H, d, J=7.6 Hz, phenyl), 6.96 (2H, d, J=8.5 Hz, phenyl), 7.08 (1H, t, J=7.3 Hz, 7.6 Hz, phenyl), 7.17 (1H, t, J=7.6 Hz, phenyl), 7.30 (2H, t, J=7.3 Hz, phenyl), 7.71-7.74 (2H, m, J=2.4 Hz, 3.0 Hz, phthalimidyl), 7.82-7.86 (2H, m, J=2.4 Hz, 3.0 Hz, phthalimidyl); MS (ESI): m/z=550.9 [M+H].

41-4. Preparation of 4-phthalimidobutyl 3-hydroxy-5-methyl-6 (3-phenoxybenzyl)-2-propylisonicotinate (46d)

Compound 46d (22.7 mg) was obtained by reacting Compound 45d (33.1 mg, 0.049 mmol) according to the general procedures for the synthesis of Compounds 46a-j described above.

Yield=79%; $^1$H NMR (CDCl$_3$, 400 MHz) δ 0.96 (3H, t, J=7.3 Hz, CH$_3$), 1.67-1.73 (2H, m, J=7.6 Hz, 7.9 Hz, CH$_2$), 1.82-1.84 (4H, br, CH$_2$), 2.33 (3H, s, CH$_3$), 2.81 (2H, t, J=7.6 Hz, CH$_2$), 3.75 (2H, t, J=6.4 Hz, CH$_2$), 4.16 (2H, s, CH$_2$), 4.27 (2H, t, J=5.8 Hz, CH$_2$), 6.78 (2H, d, J=8.5 Hz, phenyl), 6.86 (1H, d, J=7.6 Hz, phenyl), 6.96 (2H, d, J=8.5 Hz, phenyl), 7.07 (1H, t, J=7.3 Hz, phenyl), 7.19 (1H, d, J=7.6 Hz, 7.9 Hz, phenyl), 7.30 (2H, t, J=7.3 Hz, 7.6 Hz, phenyl), 7.69-7.73 (2H, m, J=2.1 Hz, 3.1 Hz, 3.4 Hz, phthalimidyl), 7.81-7.84 (2H, m, J=3.1 Hz, phthalimidyl), 10.41 (1H, s, OH); MS (ESI): m/z=578.9 [M+H].

41-5. Preparation of 2-(pyrrolidin-1-yl)ethyl 3-hydroxy-5-methyl-6-(3-phenoxybenzyl)-2-propylisonicotinate (46e)

Compound 46e (7.4 mg) was obtained by reacting Compound 45e (23.7 mg, 0.042 mmol) according to the general procedures for the synthesis of Compounds 46a-j described above.

Yield=37%; $^1$H NMR (CDCl$_3$, 400 MHz) δ 0.95 (3H, t, J=7.3 Hz, 7.6 Hz, CH$_3$), 1.64-1.71 (2H, m, J=7.3 Hz, 7.6 Hz, CH$_2$), 1.85-1.89 (4H, br, CH$_2$), 2.18 (3H, s, CH$_3$), 2.62-2.71 (4H, br, CH$_2$), 2.78 (2H, t, J=7.6 Hz, 7.9 Hz, CH$_2$), 2.84 (2H, t, J=5.2 Hz, 5.8 Hz, CH$_2$), 4.10 (2H, s, CH$_2$), 4.56 (2H, t, J=5.2 Hz, 6.1 Hz, CH$_2$), 6.78 (1H, d, J=7.9 Hz, phenyl), 6.84 (1H, s, phenyl), 6.88 (1H, d, J=7.6 Hz, phenyl), 6.96 (2H, d, J=7.6 Hz, phenyl), 7.07 (1H, t, J=7.3 Hz, phenyl), 7.18 (1H, t, J=7.6 Hz, 7.9 Hz, phenyl), 7.30 (2H, t, J=7.3 Hz, 7.6 Hz, phenyl); MS (ESI): m/z=475.0 [M+H].

41-6. Preparation of Isopropyl 3-hydroxy-5-methyl-6-(3-phenoxybenzyl)-2-propylisonicotinate (46f)

Compound 46f was obtained by reacting Compound 45f (20.2 mg, 0.040 mmol) according to the general procedures for the synthesis of Compounds 46a-j described above.

Yield 13.0 mg (78%); $^1$H NMR (CDCl$_3$, 400 MHz) δ ppm 10.43 (1H, s, OH), 7.28-7.32 (2H, m, phenyl), 7.20 (1H, t, J=7.8 Hz, phenyl), 7.05-7.09 (1H, m, phenyl), 6.95-6.98 (2H, m, phenyl), 6.88 (1H, d, J=7.3 Hz, phenyl), 6.78-6.82 (2H, m, phenyl), 5.30-5.35 (1H, m, CH), 4.17 (2H, s, CH$_2$), 2.81 (2H, dd, J=6.9 Hz, 8.7 Hz, CH$_2$), 2.35 (3H, s, CH$_3$), 1.66-1.75 (2H, m, CH$_2$), 1.39 (6H, d, J=6.4 Hz, CH$_3$), 0.97 (3H, t, J=7.6, CH$_3$); MS (ESI): m/z=419.6 [M+H].

41-7. Preparation of Pentan-3-yl 3-hydroxy-5-methyl-6-(3-phenoxybenzyl)-2-propylisonicotinate (46g)

Compound 46g was obtained by reacting Compound 45g (9.7 mg, 0.018 mmol) according to the general procedures for the synthesis of Compounds 46a-j described above.

Yield 5.6 mg (70%); $^1$H NMR (CDCl$_3$, 400 MHz) δ ppm 10.56 (1H, s, OH), 7.28-7.32 (2H, m, phenyl), 7.20 (1H, t, J=8 Hz, phenyl), 7.05-7.10 (1H, m, J=7.2 Hz, phenyl), 6.95-6.98 (2H, m, phenyl), 6.88-6.90 (1H, m, phenyl), 6.82 (1H, t, J=1.6 Hz, phenyl), 6.79-6.81 (1H, m, phenyl), 5.12-5.15 (1H, m, J=6.4 Hz, CH), 4.17 (2H, s, CH$_2$), 2.80-2.84 (2H, m, J=7.6 Hz, CH$_2$), 2.37 (3H, s, CH$_3$), 1.67-1.76 (4H, m, J=7.6 Hz, CH$_2$), 1.69-1.73 (2H, m, CH$_2$), 0.97 (3H, t, J=7.6 Hz, CH$_3$), 0.95 (6H, t, J=7.6 Hz, CH$_3$); MS (ESI): m/z=447.7 [M+H].

41-8. Preparation of Cyclopentyl 3-hydroxy-5-methyl-6-(3-phenoxybenzyl)-2-propylisonicotinate (46h)

Compound 46h was obtained by reacting Compound 45h (15.8 mg, 0.029 mmol) according to the general procedures for the synthesis of Compounds 46a-j described above.

Yield 11.7 mg (89%); $^1$H NMR (CDCl$_3$, 400 MHz) δ ppm 10.57 (1H, s, OH), 7.28-7.32 (2H, m, J=7.6 Hz, phenyl), 7.20 (1H, t, J=8 Hz, phenyl), 7.06-7.10 (1H, m, J=7.2 Hz, phenyl), 6.95-6.98 (2H, m, phenyl), 6.87-6.89 (1H, m, phenyl), 6.80-6.82 (1H, m, phenyl), 6.78-6.79 (1H, m, phenyl), 5.48-5.52 (1H, m, J=2.8 Hz, CH), 4.17 (2H, s, CH$_2$), 2.80-2.84 (2H, m, J=7.6 Hz, CH$_2$), 2.34 (3H, s, CH$_3$), 1.94-1.97 (2H, m, CH$_2$), 1.83-1.88 (4H, m, CH$_2$), 1.68-1.73 (4H, m, CH$_2$), 0.97 (3H, t, J=7.2 Hz, CH$_3$); MS (ESI): m/z=445.7 [M+H].

41-9. Preparation of Tetrahydrofuran-3-yl 3-hydroxy-5-methyl-6-(3-phenoxybenzyl)-2-propylisonicotinate (46i)

Compound 46i was obtained by reacting Compound 45i (22.7 mg, 0.035 mmol) according to the general procedures for the synthesis of Compounds 46a-j described above.

Yield 7.6 mg (56%); $^1$H NMR (CDCl$_3$, 400 MHz) δ ppm 10.33 (1H, s, OH), 7.29-2.33 (2H, m, J=2 Hz, 7.6 Hz, phenyl), 7.17-7.22 (1H, m, J=1.2 Hz, 8 Hz, phenyl), 7.06-7.10 (1H, m, J=1.2 Hz, 7.6 Hz, phenyl), 6.95-6.97 (2H, J=1.2 Hz, 7.6 Hz, phenyl), 6.87-6.89 (1H, m, J=7.6 Hz, phenyl), 6.80-6.82 (1H, m, phenyl), 6.78 (1H, m, phenyl) 5.58-5.62 (1H, m, J=2 Hz, CH), 4.17 (2H, s, CH$_2$), 3.97-4.00 (2H, m, CH$_2$), 3.93-3.96 (2H, m, J=4.4 Hz, CH$_2$), 2.80-2.84 (2H, m, J=2 Hz, 7.6 Hz, CH$_2$), 2.36 (3H, s, CH$_3$), 2.25-2.35 (1H, m, J=2.4 Hz, 6 Hz, CH$_2$), 2.17 (1H, s, CH$_2$), 1.67-1.75 (2H, m, J=1.6 Hz, 7.6 Hz, CH$_2$), 0.969 (3H, t, J=7.2 Hz, CH); MS (ESI): m/z=447.6 [M+H].

41-10. Preparation of 1-(Tert-butoxycarbonyl)piperidin-4-yl 3-hydroxy-5-methyl-6-(3-phenoxybenzyl)-2-propylisonicotinate (46j)

Compound 46j was obtained by reacting Compound 45i (10.8 mg, 0.019 mmol) according to the general procedures for the synthesis of Compounds 46a-j described above Yield 13.1 mg (67%); $^1$H NMR (CDCl$_3$, 400 MHz) δ ppm 10.44 (1H, s, OH), 7.28-7.33 (2H, m, J=2.4 Hz, 7.2 Hz, phenyl), 7.18-7.22 (1H, m, J=7.6 Hz, phenyl), 7.06-7.10 (1H, m, J=1.2 Hz, 7.6 Hz, phenyl), 6.95-7.00 (2H, m, J=1.2 Hz, 7.6 Hz, phenyl), 6.88 (1H, d, J=8 Hz, phenyl), 6.79-6.83 (2H, m, phenyl), 5.27-5.34 (1H, br, CH), 4.17 (2H, s, CH$_2$), 3.66-3.76 (2H, br, CH$_2$), 3.31-3.40 (2H, br, CH$_2$), 2.80-2.84 (2H, m, J=8 Hz, CH$_2$), 2.37 (3H, s, CH$_3$), 1.95-2.04 (2H, br, CH$_2$), 1.73-1.82 (2H, br, CH$_2$), 1.68-1.72 (2H, m, J=1.2 Hz, 8 Hz, CH$_2$), 1.47 (9H, s, CH$_3$), 0.97 (3H, t, J=7.2 Hz, CH$_3$); MS (ESI): m/z=560.1 [M H].

Example 42. Preparation of Piperidin-4-yl 3-hydroxy-5-methyl-6-(3-phenoxybenzyl)-2-propylisonicotinate (47)

Compound 46j (1.0 equiv) was dissolved in 20% TFA diluted with DCM. The mixture was stirred at room temperature for 1 hour, and subsequently extracted with dichloromethane. The organic phase was collected and dried over anhydrous Na$_2$SO$_4$. After filtration, the solvent was evaporated under vacuum. The residue was purified by silica gel column chromatography with n-hexane:EA=5:1, as an eluent.

Yield 5.9 mg (67%); $^1$H NMR (CDCl$_3$, 400 MHz) δ ppm 7.28-7.33 (2H, m, J=7.6 Hz, phenyl), 7.20 (1H, t, J=8 Hz, phenyl), 7.06-7.10 (1H, m, J=1.2 Hz, 7.2 Hz, phenyl), 6.95-6.98 (2H, m, J=1.2 Hz, 7.2 Hz, phenyl), 6.88-6.90 (1H, m, J=7.2 Hz, 6.78-6.84 (2H, m, phenyl), 5.22-5.29 (1H, br, CH), 4.17 (2H, s, CH$_2$), 3.10-3.18 (2H, br, CH$_2$), 2.86-2.92 (2H, br, CH$_2$), 2.80-2.84 (2H, m, J=2 Hz, 7.6 Hz, CH$_2$), 2.38 (3H, s, CH$_3$), 2.04 (2H, s, CH$_2$), 1.70-1.74 (4H, m, J=2 Hz, 7.6 Hz, CH$_2$), 0.97 (3H, t, J=7.2 Hz, CH$_3$); MS (ESI): m/z=461.1 [M+H].

Example 43. Preparation of Ethyl 3-hydroxy-5-methyl-6-(3-phenoxybenzyl)-2-propylisonicotinate (48)

The compound was synthesized from Compound 25 (1.2 g, 3.6 mmol) and ethyl crotonate (0.90 μL, 7.2 mmol) according to the following general procedures for the synthesis of Compounds 12a-k.

Yield 0.62 g (42%); $^1$H NMR (CDCl$_3$, 400 MHz) δ ppm 0.95 (3H, t, J=7.6 Hz, CH$_3$), 1.30 (3H, m, CH$_3$), 1.64-1.73 (2H, m, CH$_2$), 2.39 (3H, s, CH$_3$), 2.77-2.84 (2H, m, CH$_2$), 4.16 (2H, s, CH$_2$), 4.21-4.29 (2H, m, CH$_2$), 6.73-6.79 (2H, m, phenyl), 6.83-6.86 (1H, m, phenyl), 6.92-6.96 (2H, m, phenyl), 7.02-7.08 (1H, m, phenyl), 7.13-7.18 (1H, m, phenyl), 7.25-7.31 (2H, m, phenyl), 10.31 (1H, s, OH); MS (ESI): m/z=406.3 [M+H].

Experimental Example 1. Test on Antagonistic Action for Receptors

For examination of effects of the compounds as prepared in above Examples on (1) the antagonistic activity for recombinant mouse P2X1 and human P2X3 receptors and (2) ethidium bromide accumulation in human P2X$_7$ receptor, the following experiments were conducted.

1-1. Two-Electrode Voltage Clamp Assay for Recombinant mP2X1 and hP2X3 Receptors

*Xenopus* oocytes were isolated and incubated with 270 U/mg of collagenase at 23 to 24° C. for 1.5 hours. Defolliculated oocytes were kept in Barth's solution at 18° C. After 1 day, the defolliculated oocytes were each microinjected cytosolically with mP2X1 and human P2X3 receptor cRNA (40 mL, 1 μg/mL), incubated for 24 hours at 18° C. in Barth's solution. The cRNA-injected oocytes were kept for 12 days at 4° C. ATP-activated membrane currents ($V_h$=−70 mV) were recorded from the cRNA-injected oocytes using the two-electrode voltage clamp technique (Axoclamp 2B amplifier). Voltage recording (1-2 MA tip resistance) and current-recording microelectrodes (5 MΩ tip resistance) were filled with 3.0 M KCl. Oocytes were placed in an electrophysiological chamber continuously superfused with Ringer's solution (5 mL/min, at 18° C.) containing 110 mM NaCl, 2.5 mM KCl, 5 mM HEPES and 1.8 mM BaCl$_2$, with pH adjusted to 7.5. To induce an evoked current, 2 μM ATP was superfused for 60 to 120 seconds and then washed for 20 min. For data analysis, the ATP-evoked current was normalized at pH 7.5. The compounds were introduced to the fixed oocytes 20 minutes prior to ATP exposure in the electrophysiological chamber. IC$_{50}$ values (the concentration of the compound required to inhibit the ATP response by 50%) were determined by Hill plots designed using the Chemical Formula: $\log(I/I_{max}-1)$, where I is the current evoked by ATP in the presence of an antagonist. Data are presented as mean±SEM (n≥3) from different batches of oocytes.

1-2. Ethidium Bromide Accumulation Assay in hP2X-Expressing HEK293 Cells

HEK293 cells that are stably transfected with the human P2X7 receptor (P2X7R) were kept under a humidified atmosphere of 5% CO$_2$ at 37° C. in DMEM supplemented with 10% (v/v) FBS, 2 mM L-glutamine and antibiotics (50 U/mL penicillin and 50 μg/ml streptomycin). BzATP-induced pore formation was measured using a fluorescence plate reader by measuring cellular absorption of ethidium in the hP2X7-expressing HEK293 cells. The hP2X7-expressing HEK293 cells were washed once with an appropriate assay buffer, and the buffer was also removed before subsequent analysis. All studies were performed at room temperature and the final assay volume was 100 μL. The cells were resuspended at 2.5×10$^6$ cells/mL in assay buffers consisting of 10 mM HEPES, 5 mM N-methyl-D-glucamine, 5.6 mM KCl, 10 mM D-glucose and 0.5 mM CaCl$_2$ (pH 7.4) and supplemented with 280 mM sucrose or 140 mM NaCl.

In order to determine the antagonistic activity of the 5-hydroxyl-pyridine derivatives of the present invention and the reference compound (AZD9056), these compounds were added to the cells at a concentration of 10 μM with BzATP without pre-incubation. The cells were incubated for 2 hours under a humidified atmosphere of 5% $CO_2$ at 37° C., and the absorption of ethidium dye was observed by measuring fluorescence with a Bio-Tek instrument FL600 fluorescent plate reader (excitation wavelength of 530 nm and emission wavelength of 590 nm). The results are expressed as a percentage relative to the maximum cumulative amount of ethidium bromide when stimulated with BzATP alone.

1-3. Chemical Structure-Activity Relationship for In Vitro P2X Receptor Antagonism In order to investigate the structure-activity relationship (SAR) of the compounds synthesized in the present invention, the antagonistic activity was evaluated by a two-electrode voltage clamp (TEVC) assay in *Xenopus* oocytes expressing the recombinant mP2X1 or hP2X3, respectively. The hP2X7R antagonistic activity was assessed using an ethidium ion accumulation assay in human HEK293 cells stably expressing the recombinant human P2X7R. Compound 1, NF-449 and AZD9056 were tested together as positive control antagonists for mP2X1, hP2X3 and hP2X7R, respectively.

Although the present inventors reported a potent antagonist Compound 7c with an $IC_{50}$ of 60 nM against hP2X3R for the inhibitory pain signaling activity, the in vitro metabolic stability of Compound 7c was found to be extremely low (% remaining after incubation for 30 minutes with S9 microsomal fraction), and this was presumably due to 4-aldehydes. Thus, the present inventors have made extensive efforts to optimize the combination of moieties at positions 3, 4 and 6 in the 5-hydroxy pyridine backbone, including modifications of the 4-aldehyde group.

The results are shown in Table 2 below.

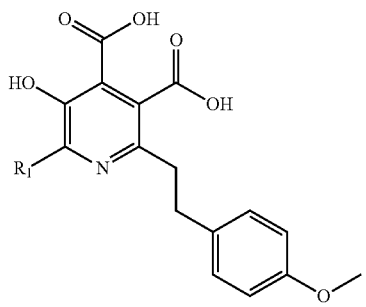

Table. 2 Antagonistic Effects of 3,4-Dicarboxypyridine Derivatives for mP2X1, hP2X3, and hP2X7 Receptors with Modification of $R_1$ The ion current responses evoked by 2 μM ATP in the recombinant P2X receptors expressed in [a]*Xenopus* oocytes, and the % inhibitory effect of the compounds shown the Table were measured at 1 μM[b], 10 μM[c] or $IC_{50}$[d] for mP2X1 and hP2X3 receptors (mean±SEM, n≥3). Ethidium bromide[e] accumulation was measured in the hP2X7-expressing HEK293 cells, and the % inhibition of accumulation by the compounds shown in the Table above was assessed at 10 M (mean±SEM, n≥3). The present inventors reported $IC_{50}$ values in previous studies as follows: [g]1 ($IC_{50}$=97 nM for A-317491, hP2X3 receptor), [h]NF-449 ($IC_{50}$=280 μM for rP2X1 receptor), [i]AZD9056 ($IC_{50}$=13 nM for hP2X1 receptor).

As shown in Table 2, the P2XR antagonistic effects of the substituents at carbon position 6 of the 3,4-dicarboxypyridine derivatives were investigated with various alkyl, aromatic and negatively charged atom-containing groups. In SAR analysis of the derivatives according to the length of the straight carbon chains, the hP2X3R antagonist activity was increased as the number of carbon chains increased from 0 to 4. In particular, the $IC_{50}$ values for Compounds 13d and 13e with carbon chain lengths of 3 and 4 was increased by 4-5 fold compared to Compounds 13a to 13c, resulting in a significantly increase in $IC_{50}$ values (93 and 95 nM, respectively). Interestingly, the order of the mP2X1R antagonistic action was reverse compared to hP2X3R, indicating that the efficacy in the mP2X1R was markedly decreased sequentially with increasing length and volume of the carbon chain at carbon position 6. Thus, about 100-fold selectivity (Compounds 13d and 13e) for hP2X3R to mP2X1R was achieved by optimizing the length of the carbon chain between 0 and 4 from non-selective Compounds 13a and 13b.

When the compound was substituted with a bulky carbon chain, such as isopropyl (Compound 13f) or isobutyl (Compound 13g), at the carbon position 6, the activity of Compound 13f in hP2X3R ($IC_{50}$=466 nM) was similar to the

TABLE 2

| Compounds | $R_1$ | mP2X1[a] | hP2X3[a] | hP2X7[e] |
|---|---|---|---|---|
| 1[g] | — | — | 35 ± 4 nM[f] | — |
| NF-449[h] | — | 307 ± 93 pM | — | — |
| AZD9056[i] | — | — | — | 0.23 ± 0.11 nM |
| 13a | —H | 236 ± 78 nM[d] | 561 ± 99 nM[d] | Inactive |
| 13b | —$CH_3$ | 446 ± 32 nM[f] | 460 ± 69 nM[f] | Inactive |
| 13c | —$CH_2CH_3$ | 48.1 ± 8.8%[c] | 550 ± 93 nM[d] | inactive |
| 13d | —$CH_2CH_2CH_3$ | 42.8 ± 7.4%[c] | 93 ± 36 nM[d] | inactive |
| 13e | —$CH_2CH_2CH_2CH_3$ | 41.9 ± 9.1%[c] | 95 ± 45 nM[d] | inactive |
| 13f | —$CH(CH_3)_2$ | 37.3 ± 8.2%[c] | 466 ± 99 nM[d] | inactive |
| 13g | —$CH_2CH(CH_3)_2$ | 23.4 ± 0.8%[c] | 32.3 ± 1.6%[b] | inactive |
| 13h | —$CH_2C_6H_5$ | Inactive[c] | 751 ± 83 nM[d] | Inactive |
| 13i | —$CH_2CH_2C_6H_5$ | Inactive[c] | 742 ± 73 nM[d] | inactive |
| 13j | —COOH | 36.7 ± 2.8%[c] | 319 ± 81 nM[d] | Inactive |
| 13k | —$CH_2CH_2SCH_3$ | Inactive[c] | 287 ± 87 nM[d] | inactive |
| 13l | —$CH_2CH_2$—S(=O)$_2$—$CH_3$ | Inactive[c] | 721 ± 96 nM[d] | Inactive | activity of Compound 13b (6-Methyl analog), whereas Compound 13g showed a remarkably reduced antagonistic activity (32% inhibition, I μM), suggesting a narrow binding pocket was present at a constant distance. Thus, Compounds 13h and 13i with nonpolar phenyl groups having different carbon chains at the carbon position 6 had weaker antagonistic effects on hP2X3R with an $IC_{50}$ in the range of 700 nM. Derivatives with electrostatic potentials different from each other at the carbon position 6, such as carboxylic acid (13j), sulfide (13k) and sulfone (13l), did not provide a beneficial effect on hP2X3R antagonistic activity compared to Compound 13d, and also, it was implied that, for the antagonistic effect, the corresponding binding pockets in the receptor may be accessed mainly based on the steric management of the substituents at the carbon position 6.

Next, the present inventors examined the position preferences and bio-isotopic substitutions of the carboxylic acid moieties at positions 3 and 4. In addition, further modifications were made, as shown in Compound 18-23 (Table 3), for various electronic effects.

The results are shown in Table 3.

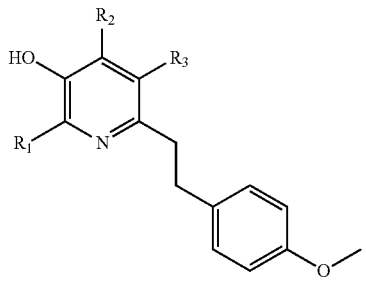

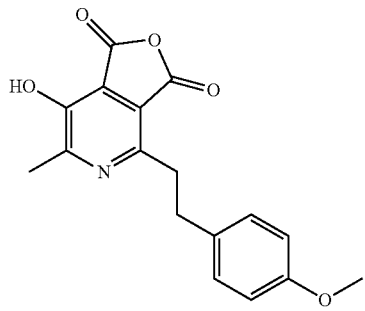

18

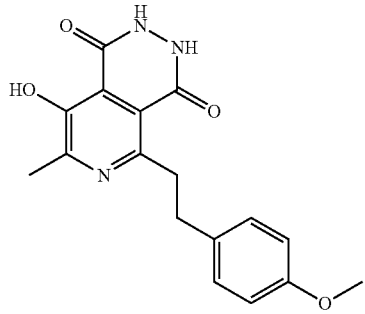

19

TABLE 3

| Compounds | $R_1$ | $R_2$ | $R_3$ | $mP2X_1{}^a$ | $hP2X3{}^a$ | $hP2X7{}^e$ |
|---|---|---|---|---|---|---|
| 16 | —CH$_3$ | —CN | —COOH | Inactive$^c$ | 33.3 ± 3.1%$^b$ | Inactive |
| 17 | —CH$_3$ | tetrazole | —COOH | Inactive$^c$ | 27.3 ± 1.8%$^b$ | inactive |
| 18 | | | | | 25.3 ± 2.8%$^c$ | 27.8 ± 1.3%$^b$ | inactive |
| 19 | | | | Inactive$^c$ | 16.3 ± 3.2%$^b$ | inactive |
| 20 | —CH$_3$ | —S(=O)$_2$—CH$_3$ | —H | inactive$^c$ | 20.4 ± 3.7%$^b$ | inactive |
| 22a | —CH$_3$ | —COOH | —H | Inactive$^c$ | 681 ± 98 nM$^d$ | Inactive |
| 22b | —CH$_3$ | —COOH | —CH$_3$ | Inactive$^c$ | 385 ± 99 nM$^d$ | inactive |
| 22c | —CH$_2$CH$_2$CH$_3$ | —COOH | —CH$_3$ | 22.7 ± 1.9%$^c$ | 303 ± 66 nM$^d$ | Inactive |
| 23 | —CH$_2$CH$_2$CH$_3$ | —CONH$_2$ | —CH$_3$ | Inactive$^c$ | 709 ± 60 nM$^d$ | inactive |

Table. 3 Antagonistic Effects of 5-Hydroxy Pyridine Derivatives for mP2X1, hP2X3, and hP2X7 Receptors with Various Modifications of Pyridine The ion current responses evoked by 2 μM ATP in the recombinant P2X receptors expressed in [a]Xenopus oocytes, and the % inhibitory effect of the compounds shown the Table were measured at 1 μM[b], 10 μM[c] or $IC_{50}^{d}$ for mP2X1 and hP2X3 receptors (mean±SEM, n≥3). Ethidium bromide accumulation was measured in [e] hP2X7-expressing HEK293 cells, and the % inhibition of accumulation by the compounds shown in the Table above was assessed at 10 μM (mean±SEM, n≥3).

As shown in Table 3, the present inventors introduced a nitrile group (Compound 16) and a methanesulfonyl group (Compound 20) as a hydrogen bond acceptor, and tetrazole (Compound 17) as a bioisostere of 4-carboxylic acid group. As a result, the antagonistic activity of the compounds for P2X1R and P2X3R was significantly reduced. Derivatives with fused heterocyclic groups such as maleic anhydride (Compound 18) and pyridazine (Compound 19), which may possibly interact with a lysine residue at the ATP binding site of P2X3R, also showed significant loss of antagonistic activity.

These results suggest that an appropriate amount of acidic functional groups at the carbon position 4 may be essential for binding in the receptors. Thus, for the purpose of reducing the polar negative property of the dicarboxylic acid group of Compound 13, the carboxylic acid was modified with —H or $CH_3$ at the carbon position 3.

Compound 22a, a mono-carboxylic acid analog at the carbon position 4 of pyridine, showed a nearly 2-fold decrease in the antagonistic activity for hP2X3R compared to Compound 13b ($IC_{50}$=460 nM), a 3,4-dicarboxylic acid analog. In contrast, Compound 22b ($IC_{50}$=384 nM), a 3-methylpyridine-4-carboxylic acid derivative, maintained the antagonistic activity for hP2X3R. Attempts to increase the potency for hP2X3R by replacing the 6-methyl group of Compound 22b with a 6-n-propyl group (Compound 22c, $IC_{50}$=303 nM) resulted in only a slight increase in the antagonistic activity. In the case of Compound 23 ($IC_{50}$=709 nM), which is a 4-carboxamide derivative having similar H-bond donator properties with less acidity, the antagonistic activity for hP2X3R was reduced by 2-fold. These results suggest that possible ionic interactions at carbon position 4 with a pharmacophore may be more important in terms of the antagonistic activity in hP2X3R than H-bond interactions.

Next, the present inventors introduced a m-phenoxyphenyl group at the carbon position 2 of the pyridine residue, which has been reported as an alternative pharmacophore for an p-methoxyphenethyl group with improved selectivity profile (Table 4). The results are shown in Table 4.

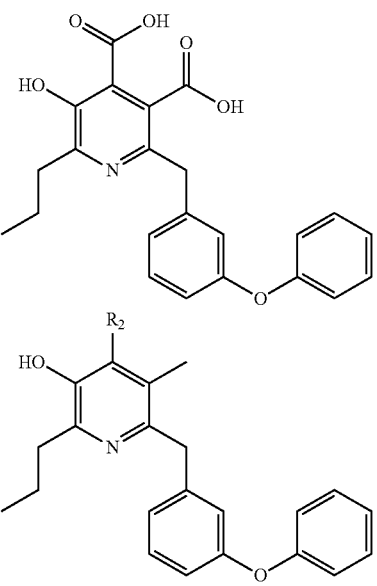

Table 4. Antagonistic Effects of 5-Hydroxy Pyridine Derivatives for mP2X1, hP2X3, and hP2X7 Receptors with Modification of m-phenoxyphenyl at Carbon Position 2 of Pyridine The ion current responses evoked by 2 μM ATP in the recombinant P2X receptors expressed in [a]Xenopus oocytes, and the % inhibitory effect of the compounds shown the Table were measured at 1 μM[b], 10 μM[c] or $IC_{50}^{d}$ for mP2X1 and hP2X3 receptors (mean±SEM, n≥3). Ethidium bromide accumulation was measured in [e]hP2X7-expressing HEK293 cells, and the % inhibition of accumulation by the compounds shown in the Table above was assessed at 10 μM (mean±SEM, n≥3).

However, 3,4-dicarboxy-2-m-phenoxyphenyl derivatives, such as Compound 27 ($IC_{50}$=301 nM), did not improve hP2X3R antagonistic effect or selectivity for mP2X1R compared to the corresponding 2-p-methoxyphenethyl analogs and Compound 13d.

In addition, the present inventors introduced $CH_3$ (Compound 29) instead of 3-carboxylic acid of Compound 27 to reduce the polarity. Unlike in the case of Compound 22c and Compound 13d, 4-carboxy-3-methyl-2-m-phenoxyphenyl derivatives (Compound 29, $IC_{50}$=245 nM) maintained the hP2X3R antagonistic efficacy of Compound 27.

Figure 2A:
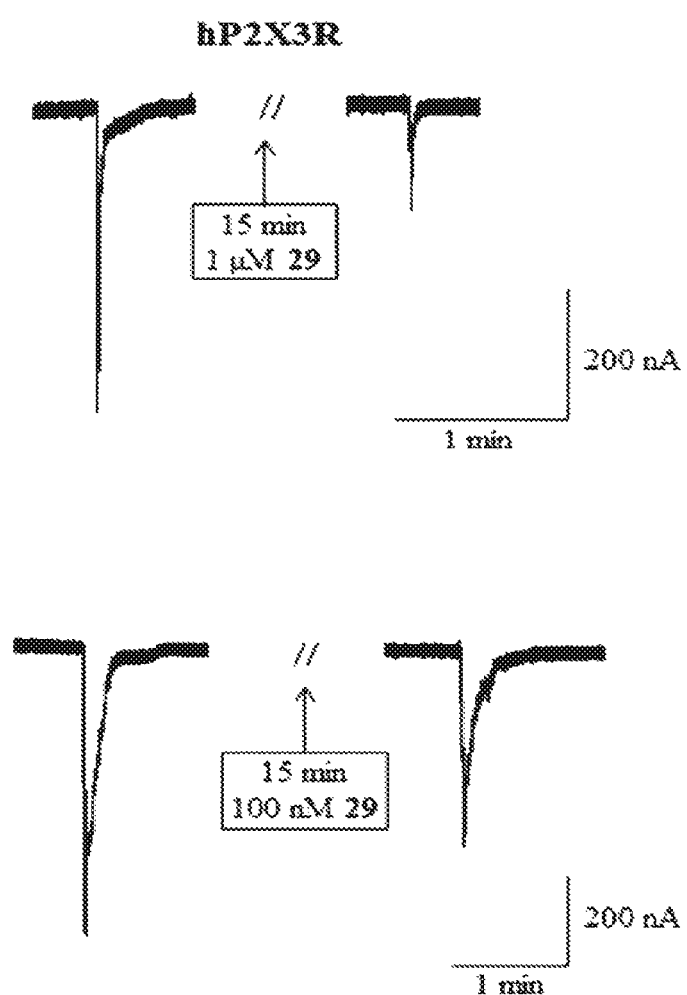
FIGS. 2a to 2c show the antagonistic activity of Compound 29 of the present invention for P2X3 and P2X2/3 receptors (2a: hP2X3R, 2b: rP2X3/3).
Figure 2B:
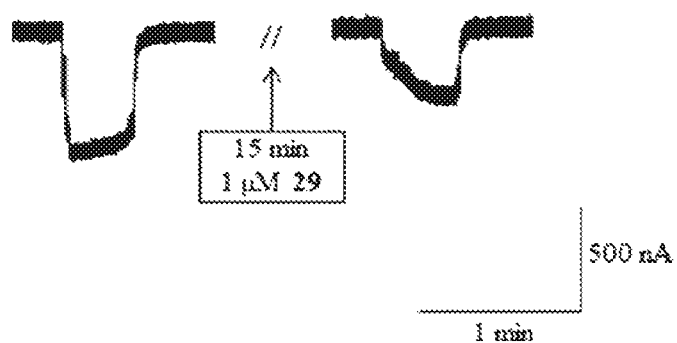
Figure 2B:
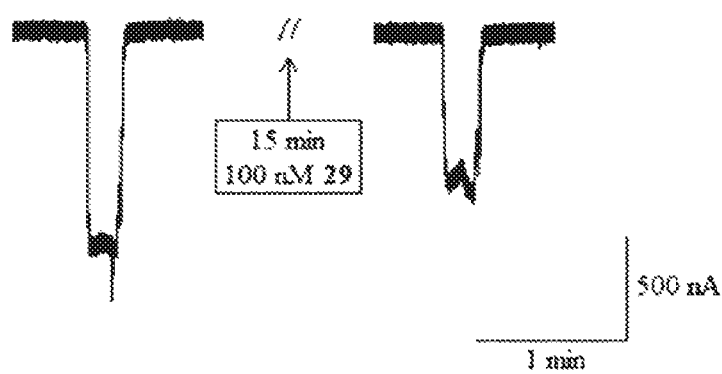
Figures 2C, 3A:
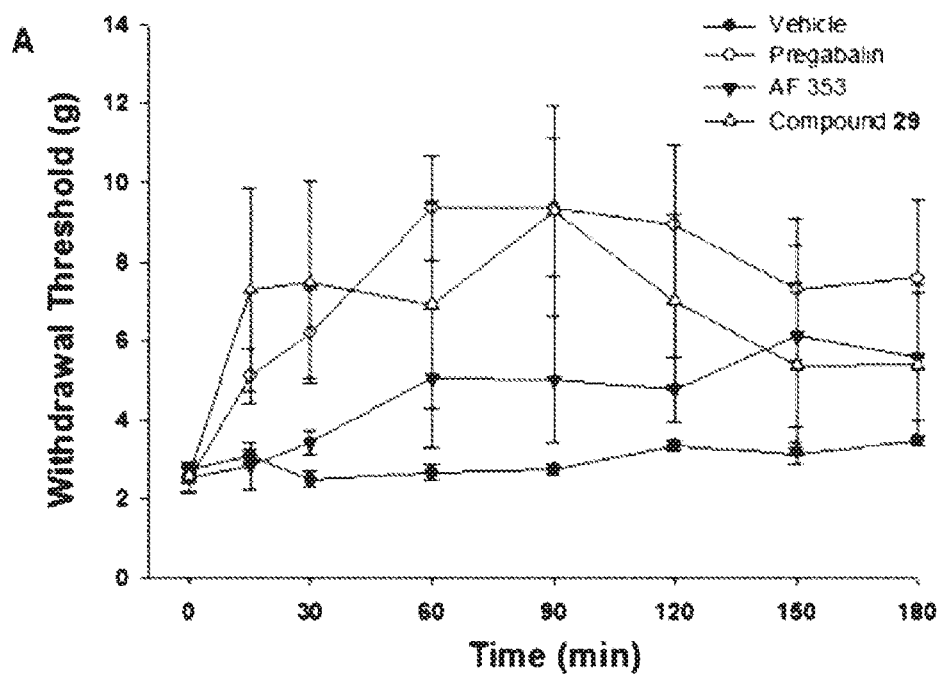
FIGS. 3a and 3b show the antiallodynic effect of SNL rats by intradural administration of pregabalin, AF353 and Compound 29. The percentage of withdrawal threshold or maximum possible effect (% MPE at 1 μg) represents the mean±SEM of 5 to 6 rats for each experimental group. * $P<0.05$ compared to vehicle (control).
Figure 3B:
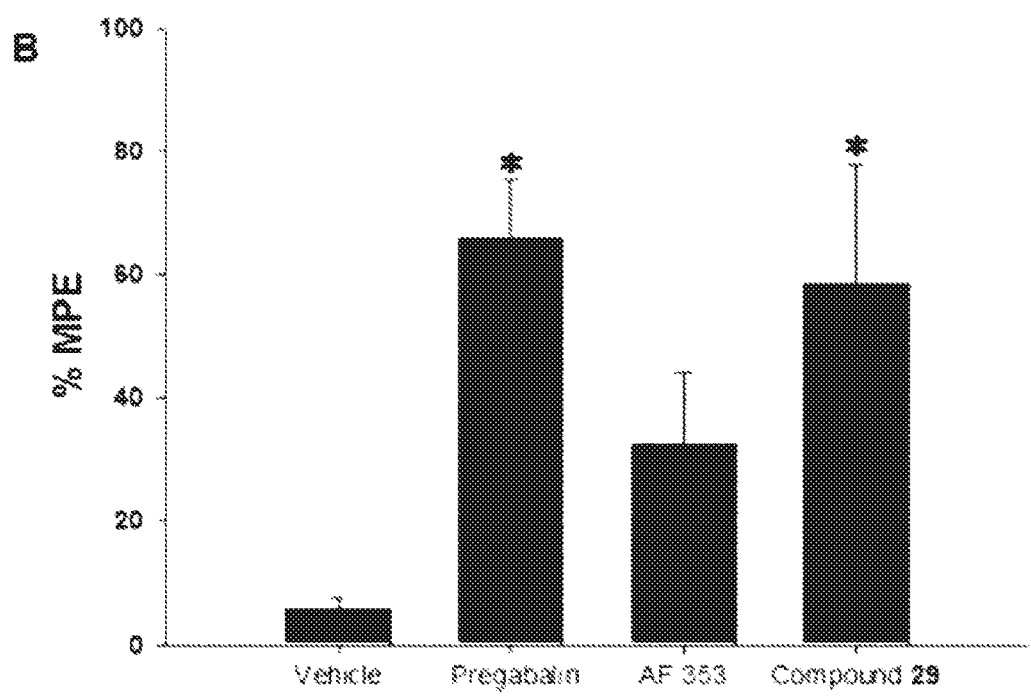

Further, Compound 29 also showed an antagonistic effect for heterologous rP2X2/3 receptors, which are more physiologically relevant receptors (FIG. 2a, FIG. 2b, FIG. 2c).

Further research have been made on the effect of other substituents on the carbon position 4 of Compound 29,

TABLE 4

| Compounds | $R_2$ | mP2X1[a] | hP2X3[a] | hP2X7[e] |
|---|---|---|---|---|
| 27 | | 27.5 ± 4.5%[c] | 301 ± 65 nM[d] | Inactive |
| 29 | —COOH | 23.3 ± 4.8%[c] | 245 ± 29 nM[d] | Inactive |
| 35 | —CH=CHCOOH | Inactive[c] | 37.0 ± 1.0%[b] | inactive |
| 37 | —$CH_2CH_2$COOH | inactive[c] | 29.7 ± 3.1%[b] | inactive |
| 38 | —CN | inactive[c] | 32.4 ± 0.8%[b] | inactive |
| 41 | —$CH_2NH_2$ | inactive[c] | 34.4 ± 1.2%[b] | inactive |
| 43 | —$CH_2$NH—S(=O)$_2$—$CH_3$ | 43.1 ± 12.9%[c] | 42.4 ± 2.1%[b] | inactive | including carbon chain-extended carboxylic acids such as 4-propenoic acid (Compound 35) or 4-propionic acid (Compound 37), 4-nitrile (Compound 38), 4-methylamine (Compound 41) and 4-methinesulfone amide (Compound 43). However, all compounds showed less than 50% inhibition at a concentration of 1 µM for hP2X3R. Thus, it is assumed that the binding partner for the pharmacophore at the carbon position 4 of the pyridine ring may consist of amino acids that can form ionic interactions with narrow binding pockets. 5-hydroxy pyridine derivatives were evaluated for subtype selectivity to the mP2X1 receptor and the hP2X7 receptor. As a result, all compounds shown in Tables 3 and 4 at a concentration of 10 µM exhibited inhibitory activity of 0 to 43% against mP2X1R and showed inactiveness to hP2X7R.

Among the novel hP2X3 receptor antagonists, Compound 29 was selected for further evaluation of functional activity in in vivo neuralgia (NeP) animal models. Compound 13d, found to be a more potent antagonist, was excluded due to its weak in vivo efficacy in early animal experiments, and this was presumably due to the high polar physicochemical properties.

Experimental Example 2. Pharmacokinetics (PK) and hERG Channel Test 2-1. Pharmacokinetic Test Method
Experimental Animals 7 to 8-weeks old male SD rats (weight of 250 to 290 g) were purchased from SAMTACO (Osan, Gyeongsan, South Korea) and given commercial rat feed (SAMTACO, Osan, Kyungki-Do, South Korea) and water to be consumed freely. 3 rats were housed per each cage at a temperature of 23±2° C. and a relative humidity of 50 to 60% under light-darkness cycles of 12±12 hours. The rats were allowed to acclimate to these conditions for at least one week before the experiments was carried out. The rats were fasted for 12 hours before the experiment and given the tap water to be consumed freely. Compound 28 was administered to the caudal vein at a dose of 5 mg/kg. At 0.5, 2, 4 and 8 hours after intravenous administration, each animal was sacrificed by cervical dislocation. Blood samples were centrifuged at 12,000 rpm for 5 minutes and immediately stored at 70° C. until analysis. After collecting the blood samples, the brains were harvested. Then, the brain tissues were accurately weighed and homogenized with 4-fold volumes of distilled water (IKA T10 basic homogenizer, IKA, Staufen, Germany). The homogenized brain samples were centrifuged at 12,000 rpm for 10 minutes and stored at −20° C. until analysis of 500 µl aliquots. Quantification of the samples was performed using an LC-MS/MS system. The HPLC system is composed of an Agilent 1290 series rapid resolution LC system that includes a binary pump (model: G4220A), an autosampler (model: G4226A) and a column oven (model: G1316C). Mass spectrometer analysis was performed using a Sciex 4000 Q-Trap® mass spectrometer (Applied Biosystems Sciex, Toronto, Ontario, Canada) equipped with an electrospray ionization source. Data acquisition and quantification were performed using the Analyst software version 1.6 from AB SCIEX, and chromatographic separations were performed using Gemini NX C18 (2.0×100 mm, 3 µm, Phenomenex, USA). The mobile phase consisted of ACN (0.1% formic acid) and water (0.1% formic acid) (50:50, v/v). The flow rate was 0.25 mL/min, and the injection volume was set at 5 µL. Mass spectrometry was optimized and performed using a multiple reaction monitoring (MRM) scan in cation mode. The m/z transition was set from 392.1 to 360.2 for Compound 28 and from 378.2 to 360.2 for Compound 29. Preparation of plasma and brain homogenous samples includes protein precipitation with acetonitrile. In 1.5 mL polyethylene microtubes, 5 µL of IS (cimetidine, 10 µg/ml) was added to 50 µL of plasma or tissue homogenate. Subsequently, 150 µl of acetonitrile (extraction solvent) was added to the tube. After vortexing for 30 seconds, the mixture was centrifuged for 5 minutes at 12,000 rpm. 10 µl of supernatant was injected directly into the HPLC column.

Microsomal Stability

Metabolic stability of the compounds was evaluated in rat liver microsomes (RLM). Microsomes (0.5 mg/ml) and test compound (1 µM) in 100 mM potassium phosphate buffer (pH 7.4) were preincubated by shaking at 37° C. for 5 min (100 rpm). Metabolic reactions were initiated by adding an NADPH production system (60 mM potassium phosphate buffer at pH 7.4, 1.3 mM NADP, 3.3 mM glucose-6-phosphate, 0.3 µL glucose-6-phosphate dehydrogenase (0.4 U/mL), and 3.3 mM magnesium chloride) and incubating at 37° C. 100 µL aliquots were recovered at 0, 10, 20, 30 and 60 minutes, and the reaction was terminated by the addition of two volumes of ice-cold acetonitrile (ACN). After mixing by vortex and centrifugation (14000 rpm) for 15 minutes at 4° C., the supernatant was transferred to liquid chromatography vials and analyzed by an LC-MS/MS system.

Plasma Protein Binding

Plasma protein binding was measured by rapid equilibrium dialysis (RED). A DMSO stock solution of the compounds was prepared at a concentration of 10 mM and diluted to a concentration of 5 IM with 50% plasma in phosphate buffered saline (PBS, pH 7.4). Plasma samples (100 µL) and PBS (300 µL) were added to the sample chamber and the buffer chamber, respectively, after which the RED device was turn on and the samples were incubated in a shaking incubator at 37° C. for 4 hours. After dialysis, 50 µl aliquots were collected from each side of the chamber. 50 µl of blank plasma was added to the buffer sample, and 50 µl of PBS was also added to the plasma sample. 200 µL of acetonitrile containing an internal standard was added to each sample. The samples were centrifuged at 3200 g for 20 minutes at 4° C., and the supernatants were obtained and analyzed by an LC-MS/MS system. The plasma protein binding rate was calculated as follows:

Free form (%)=(Buffer chamber/Plasma chamber)× 100

Bound form (%)=100−Free form (%).

PAMPA (Parallel Artificial Membrane Permeability Assay)

Test compounds were dissolved in DMSO to a concentration of 10 mg/mL. The compound stock solution was diluted 100-fold with PBS buffer and mixed to prepare a secondary stock solution at a final concentration of 100 µg/mL. The second stock solution (200 µL) was added to donor wells (pION Inc, Billerica, Mass., USA). The test compounds were analyzed at pH 7.4. The filter at the bottom of each acceptor well (pION) was wetted by the addition of 5 µL of GIT-0 lipid (pION), and the acceptor wells were then filled with sink buffer (200 µL, pION) at the same pH as the donor well (pION). The acceptor filter plate was carefully placed on the donor plate and incubated for 4 hours in Gut-BOX (pION).

After the permeation time, the concentrations of compounds in the acceptor and donor wells, as well as reference wells, were determined by quantification using a UV plate reader (Infinite 200 PRO; TECAN, Mannedorf, CHE). The effective permeability coefficient (Pe) was calculated by the PAMPA Explorer software (version 3.6.0.7, pION). The compounds were analyzed three times. Verapamil was used as a high permeability standard.

CYP Inhibition Assay

CYP450 (1A2, 2C9, 3A4) enzyme assay was performed by a fluorometric assay using a Vivid® CYP450 screening kit (Invitrogen, USA, CA) in a 96-well black plate according to manufacturer's instructions with some modifications. The assay was performed at room temperature, and the final assay volume was 100 μL. Representative compounds and known CYP450 inhibitors (1A2: α-naphthoflavone; 2C9: sulfaphenazole; 3A4: ketoconazole) were prepared to a final concentration of 10 μM in DMSO.

A master pre-mixture (enzyme (0.5 nmol recombinant human CYP450 enzyme)/NADP regeneration solution (333 mM glucose-6-phosphate dissolved, 30 U/mL glucose-6-phosphate dehydrogenase in 100 mM $KH_2PO_4$ solution at pH 8.0)) was prepared as a CYP450 reaction buffer (200 mM $KH_2PO_4$, pH 8.0). The master pre-mixture was added to each well of the 96 well plate, followed by the vehicle DMSO (control) and test compounds, and the mixture was preincubated for 10 minutes in the plate for background reading. Subsequently, the enzyme reaction was immediately initiated through the addition of CYP450 substrate/ $NADP^+$ mixture. After incubation for 40 minutes, the fluorescence of the product was measured with a CHAMELEON™ multi-technology plate reader (2C9, 3A4: excitation wavelength of 530 nm and emission wavelength of 590 nm, 1A2: excitation wavelength of 415 nm and emission wavelength of 460 nm). The effect of the test compounds on CYP450 (1A2, 2C9, 3A4) was expressed as the percentage of enzyme activity.

2-2. hERF Channel Test Method hERG $K^+$ Channel Conventional Patch-Clamp Assay

CHO-K1 cells expressing hERG channels via an inducible Tet-On gene expression system (CHO-K1 Tet-On hERG cells) were purchased from IonGate Biosciences GmbH (Frankfurt, Germany). CHO-K1 Tet-On hERG cells were incubated in Dulbecco's modified Eagle's medium (DMEM) containing 10% (v/v) fetal bovine serum, penicillin (100 U/mL), streptomycin (100 μg/mL), fungizone (2.5 μg/mL), as well as selection antibiotics, geneticin G418 (200 μg/mL), hygromycin (200 μg/mL) and puromycin (2 μg/mL) in a humidified condition of 5% $CO_2$ at 37° C. The cells were passaged by treatment with trypsin-EDTA every three days. For expression of hERG channels, 5 μg/mL of doxycycline (Sigma, St. Louis, Mo., USA) was added to the growth medium to induce the Tet-On gene expression. For automated patch clamp recording, the CHO-K1 Tet-On hERG cells were incubated in a 100-mm culture dish. The cells at confluency of 50 to 80% were harvested by treatment with trypsin-EDTA, washed twice, and then resuspended in an extracellular solution at a final cell density of $1.5 \times 10^6$ cells/mL. The cells were used for whole-cell recordings for about 20 to 32 hours after addition of doxycycline.

NPC-16 Patchliner (Nanion Technologies, Munchen, Germany), an automated patch-clamp apparatus, was used for the whole-cell recordings. Whole-cell currents were recorded using an intracellular solution (unit in mM) containing 50 KCl, 60 KF, 10 NaCl, 2 $MgCl_2$, 20 EGTA and 10 HEPES (pH 7.2) and an extracellular solution (unit in mM) containing 140 NaCl, 4 KCl, 2 $CaCl_2$, 1$MgCl_2$, 5 glucose and 10 HEPES (pH 7.4). A seal enhancer containing (unit in mM) 80 NaCl, 3 KCl, 35 $CaCl_2$), 10 $MgCl_2$ and 10 HEPES (pH 7.4) was used only at the seal formation step to help formation of stable seals. Prior to the whole-cell recordings, an external seal enhancer solution was exchanged with the extracellular solution described above.

hERG channel currents were recorded using a parallel EPC-10 patch clamp amplifier (HEKA Elektronik, Lambrecht/Pfalz, Germany), and low-pass filtering (10 kHz) was performed with a 4-pole Bessel filter. Cell suspensions and patch solutions were automatically added to four recording wells in microfabricated disposable chips (NPC-16 Chip, Nanion Technologies, Munchen, Germany).

In order to obtain the inhibitory constants, the hERG tail current was evoked by a repolarization step up to −50 mV for 500 ms preceded by a depolarization potential of +20 mV for 500 ms at a holding potential of −80 mV with a sweep interval of 20 seconds. The whole-cell currents were obtained and digitized at 5 kHz using the Patchmaster (HEKA Elektronik, Lambrecht/Pfalz, Germany). The extracellular solution was exchanged with an extracellular solution containing each blocker through four pipette tips of NPC-16 Patchliner, which uses 4-fold volumes of solution (40 μl) at a rate of 4 μl/s, and the exchanged blocking solution was added to patch-clamped cells for 100 to 200 seconds until the binding of the blockers had reached equilibrium by monitoring the hERG tail currents. The whole-cell recordings were analyzed by the Patchmaster/ Fitmaster (HEKA Elektronik, Lambrecht/Pfalz, Germany), IGOR Pro (WaveMetrics Inc., Portland, Oreg., USA), and GraphPad Prism 4 (GraphPad Software, Inc., La Jolla, Calif., USA).

2-3. Results of In Vitro Pharmacokinetics and hERG Channel Test of Compound 29 of the Present Invention As a result of the in vitro inhibitory activity assay against CYP enzymes (3A4, 2C9 and 1A2), Compound 29 showed a weak inhibitory effect, and as a result of the in vitro inhibitory activity assay against hERG channels, Compound 29 did not show any inhibitory activity. These results indicate that Compound 29 has a reasonable profile with respect to drug-drug interactions and cardiac toxicity (Table 5).

TABLE 5

Studies on In vitro Pharmacokinetics (PK) and hERG Channels

| Property | Units | Compound 28 | Compound 29 |
|---|---|---|---|
| Metabolic stability Stability— microsomes | | | |
| Human | % remaining after 30 min | 0 | 3 |
| Rat | | 33 | 0 |
| Mouse | | 35 | 2 |
| Plasma protein binding | | | |
| Human | Plasma protein binding rate (%) | 99.5 ± 0.82 | 99.9 ± 0.06 |
| Rat | | 32.5 ± 8.36 | 99.8 ± 0.13 |
| Permeability— PAMPA | log $P_e$ | −4.80 | −7.04 |
| CYP450 inhibition | | | |
| 3A4 isozyme | % inhibition at 1 μM | 12 ± 2 | 10 ± 1 |
| 2C9 isozyme | | 28 ± 3 | 26 ± 2 |
| 1A2 isozyme | | 4 ± 1 | 36 ± 3 |
| hERG | $IC_{50}$ (μM) | Not determined | >100 |

Table 5. Studies on In vitro Pharmacokinetics (PK) and hERG Channels

However, Compound 29 showed a strong plasma protein binding (>99%), a low metabolic stability (<5% after 30 minutes) and a low cell permeability (log Pe=−7.04). Thus, the corresponding methyl ester analog (Compound 28) that can be converted to Compound 29 in vivo was found to have improved metabolic stability (33% remained after 30 minutes) and plasma protein binding property with moderate cell permeability (log Pe=−4.8). In addition, intraperitoneal and intravenous administration of Compound 29 had no antiallodynic effect in neuropathic pain animal models, and thus, the in vivo efficacy of Compound 28 was evaluated.

Experimental Example 3. In Vivo Efficacy Test for Compounds of the Present Invention 3-1. Evaluation of In Vivo Efficacy The antiallodynic effects (mechanical allodynia) were evaluated using rats according to a previously reported protocol. In order to evaluate the withdrawal threshold, rats (naive, SNL and CIPN) were placed on a plastic mesh floor of individual plastic cages. The rats were allowed to acclimate to the environment for 30 minutes and examined after intrathecal or intravenous administration to the caudal vein. The control group received the same volume of vehicle (intrathecal administration of saline or DMSO, intravenous administration of DMSO:PEG:PBS=1:6:3 v/v %) as the experimental groups. Evaluation of the mechanical withdrawal threshold was measured in responses to the application of calibrated von Frey filaments (Stoelting, Wood Dale, Ill., USA) to the hind paw of the rats through the holes on the mesh floor underneath the cage using the 'up and down method'. A series of eight von Frey filaments (0.4, 0.7, 1.2, 2.0, 3.6, 5.5, 8.5, and 15 g) was applied perpendicular to the sole of the hind paw for 5 seconds while the head was bent. Active withdrawal or flinching of the paw was considered as a positive reaction. The absence of response in the rats, when a pressure was applied to 15 g von Frey filament, was used as a cut-off value. Only rats with definite allodynia (i.e., mechanical withdrawal threshold: less than 4 g after SNL or less than 5 g after CIPN) were tested. The rats after termination of the experiments were euthanized through an overdose of sevoflurane. The withdrawal threshold data for the von Frey filament test was calculated as % MPE (maximum possible effect) based on the following Calculation Equation:

% MPE=[(Post-drug threshold−Post-injured baseline threshold)/(Cutoff threshold−post-injured baseline threshold)×100].

Dose-response data were analyzed using Scheffe's post hoc test and one-way analysis of variance (ANOVA).

Figure 4A:
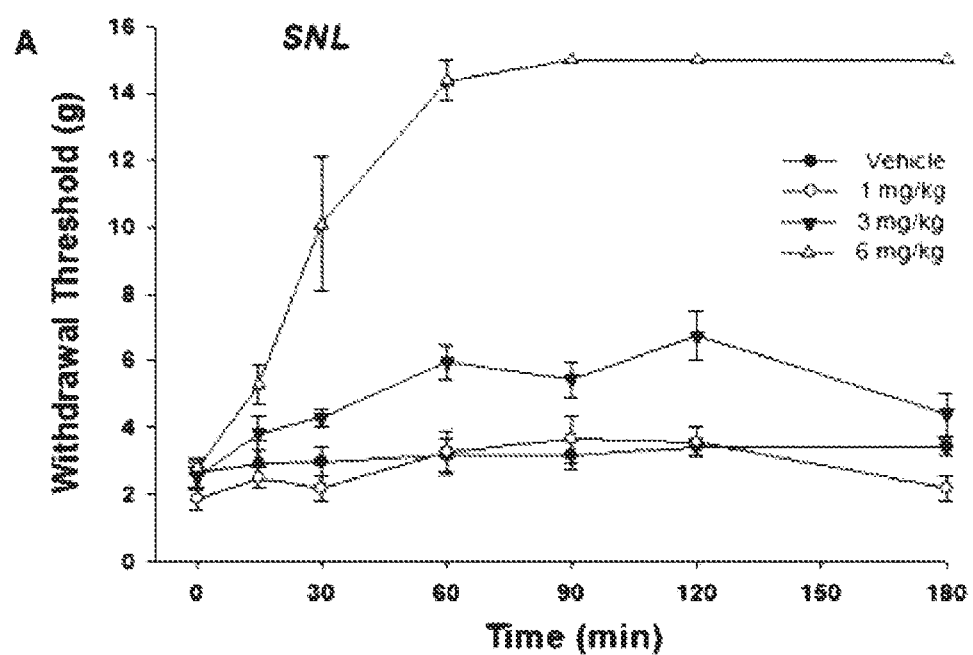
FIGS. 4a and 4b show the antiallodynic effect of SNL rats by intravenous administration of Compound 28. The percentage of withdrawal threshold or maximum possible effect (% MPE at 1 μg) represents the mean±SEM of 5 to 6 rats for each experimental group.  $P<0.01$, * $P<0.001$ compared to vehicle (control).
Figure 4B:
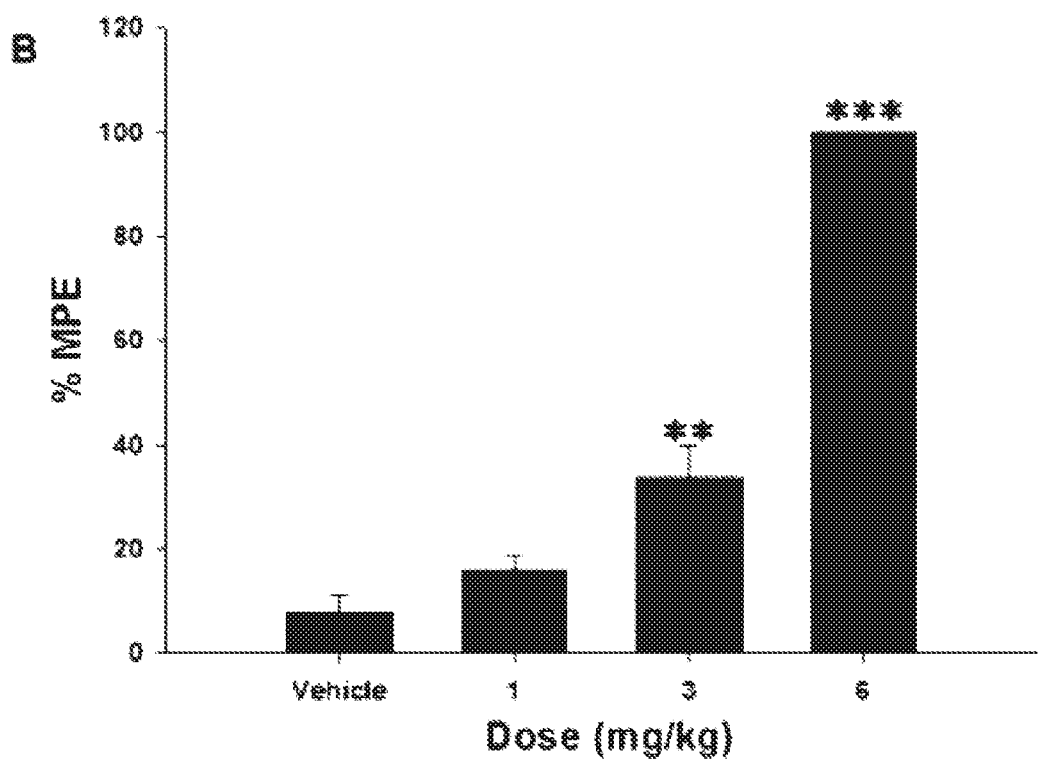

3.2 Evaluation of In Vivo Efficacy of Compound 29 in Neuropathic Pain Animal Models The antiallodynic efficacy of Compound 29 was assessed using the von Frey method after intrathecal administration in spinal nerve ligation (SNL). The results of Compound 29 showed an increase in paw withdrawal threshold as an indicator of antiallodynic effect in SNL rats (FIG. 4a, FIG. 4b).

The antiallodynic efficacy of Compound 29 (MPE %=58±19 at 1 μg (0.0026 μmol)) was shown to be more potent than the antiallodynic efficacy of AF353, a P2X3 receptor antagonist (MPE %=32*11 at 1 μg (0.0023 μmol)). The SNL rats showed antiallodynic efficacy equivalent to pregabalin (MPE %=65±9 at 1 μg (0.0063 μmol)), a calcium channel modulator. However, no pharmacological activity was observed in NeP animal models upon intraperitoneal and intravenous administration.

3-3. Evaluation of In Vivo Efficacy of Compound 28 in Neuropathic Pain Animal Models Although the intramedullary administration of Compound 29 showed a potent antiallodynic effect in NeP rats, the intravenous administration of Compound 29 did not provide an antiallodynic effect. Recently, AbbVie, Inc. reported that P2X3 receptor antagonists must be able to penetrate the blood brain barrier (BBB) in order to be effective for anti-nociceptive responses in neuropathic pain models, although it is not necessary in inflammatory pain animal models. Thus, Compound 29 may have been excessively polar to penetrate the BBB and provide an antiallodynic effect in NeP animal models by intravenous administration. In order to improve the physicochemical properties for the BBB penetration of compound 29, a prodrug strategy was studied using a methyl ester derivative of Compound 29 (Compound 28), which can be converted to Compound 29 to produce an antiallodynic effect in the CNS.

The results are shown in Table 6.

TABLE 6

|  | 0.5 hr | 2 hr | 4 hr | 8 hr |
| --- | --- | --- | --- | --- |
| Compound 28 | | | | |
| Plasma (μg/mL) | 0.62 ± 0.14 | 0.08 ± 0.02 | 0.06 ± 0.01 | 0.02 ± 0.01 |
| Brain (μg/g) | 1.11 ± 0.36 | 0.09 ± 0.01 | 0.05 ± 0.01 | 0.03 ± 0.01 |
| Brain to plasma ratio | 1.79 ± 0.44 | 1.13 ± 0.25 | 0.94 ± 0.21 | 1.19 ± 0.41 |
| Compound 29 | | | | |
| Plasma (μg/mL) | 0.11 ± 0.05 | 0.03 ± 0 | 0.02 ± 0.01 | 0.01 ± 0 |
| Brain (μg/g) | 0.022 ± 0.003 | 0.002 ± 0.001 | 0.001 ± 0 | 0.001 ± 0.001 |
| Brain to plasma ratio | 0.24 ± 0.13 | 0.08 ± 0.02 | 0.05 ± 0.03 | 0.1 ± 0.12 |

Figure 5A:
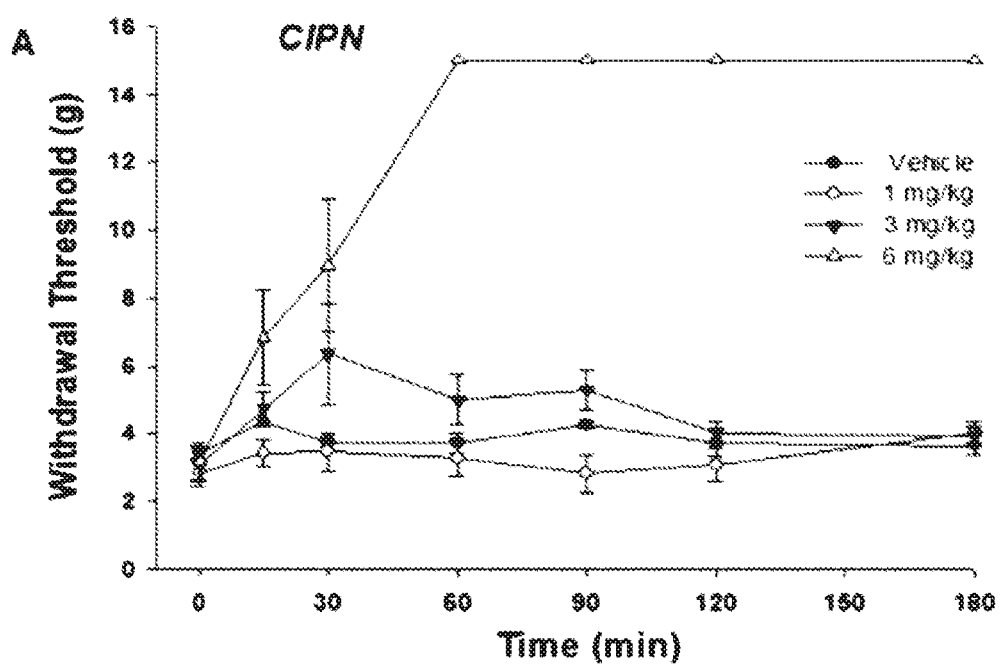
FIGS. 5a and 5b show the antiallodynic effect of CIPN rats by intravenous administration of Compound 28. The percentage of withdrawal threshold or maximum possible effect (% MPE at 1 μg) represents the mean±SEM of 5 to 6 rats for each experimental group. * $P<0.001$ compared to vehicle (control).
Figure 5B:
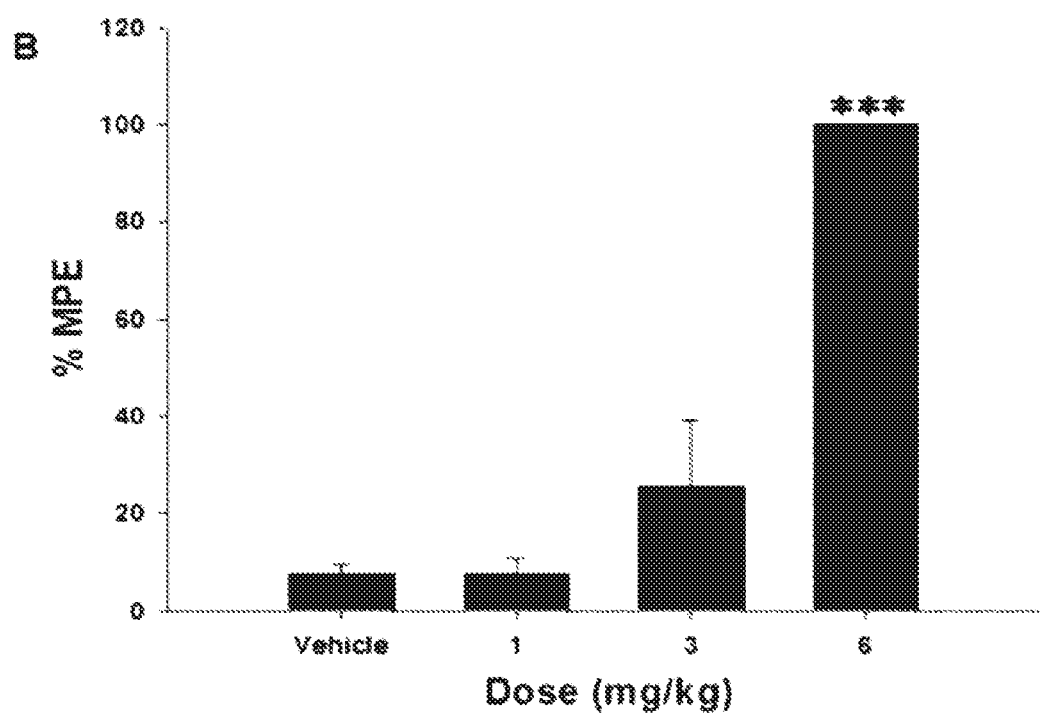

Table. 6 Concentration (mean±standard deviation) and Ratio (brain to plasma, mean±standard deviation) of Compound 28 (prodrug) and Compound 29 (active drug) after intravenous administration of Compound 28 (5 mg/kg) in Rats As shown in Table 6 above, the concentration in the brain tissue (1.11 μL/g tissue, Table 6) after 0.5 hour of intravenous administration of Compound 28 was 50 times higher than the concentration of Compound 29 (0.022 μL/g tissue, Table 6). The brain to plasma ratio of Compound 28 (1.13-1.79, Table 6) was 4.5 to 7 times higher than that of Compound 29 (less than 0.25, Table 6). Accordingly, the present inventors investigated in vivo pharmacological effects by intraperitoneal administration of Compound 28 in NeP animal models including SNL rats and chemotherapy induced chemotherapy-induced peripheral neuropathy (CIPN) rats. As a result, a potent antiallodynic effect was observed in SNL rats (FIG. 4a, FIG. 4b) with an $ED_{50}$ of 2.62 mg/kg and in CIPN rats (FIG. 5a, FIG. 5b) with an $ED_{50}$ of 2.93 mg/kg. The results implied that the overall improvement in the physicochemical properties for BBB penetration, metabolic stability and plasma protein binding properties of Compound 28 enabled the potent antiallodynic efficacy in NeP animal models by intravenous administration. The in vivo efficacy of Compound 28 was higher the efficacies of pregabalin ($ED_{50}$=4.21 mg/kg) and tramadol ($ED_{50}$=4.67 mg/kg), which are currently clinical drugs for NeP.

3-4. Evaluation of In Vivo Efficacy of Compounds 46a-i, 47 and 48

Compounds 46a-i, 47, and 48, which are prodrugs of Compound 29 and in which various ester groups were introduced in consideration of the permeability of the blood brain barrier and the possibility of conversion to Compound 29 in the CNS, were developed. Pharmacological investigations of the relevant drugs were carried out after intravenous administration to SNL and CIPN rats, neuropathic pain animal models. As a result. Compounds 46a-i, 47, and 48 of Table 7 showed antiallodynic efficacy in SNL rats with an $ED_{50}$ of 2.31 to 3.64 mg/kg and in CIPN rats with an $ED_{50}$ of 2.93 to 3.94 mg/kg.

TABLE 7

[Core structure: methyl 5-hydroxy-3-methyl-2-(3-phenoxybenzyl)-6-propyl pyridine-4-carboxylate with R5 as the ester O-substituent]

| Compounds | $R_5$ | SNL $ED_{50}$ (mg/kg) | CIPN $ED_{50}$ (mg/kg) |
|---|---|---|---|
| 45a | –CH₂CH₂–phenyl | 2.31 | 3.02 |
| 46b | –(CH₂)₇CH₃ (n-octyl) | 2.47 | 2.93 |
| 46c | –CH₂CH₂–phthalimidyl | 2.97 | 3.28 |
| 46d | –(CH₂)₄–phthalimidyl | 3.12 | 3.94 |
| 46e | –CH₂CH₂CH₂–pyrrolidin-1-yl | 3.02 | 3.55 |
| 46f | –CH₂CH(CH₃)₂ (isobutyl) | 2.78 | 3.08 |
| 46g | –CH(CH₂CH₃)₂ (3-pentyl) | 3.42 | 3.66 |
| 46h | –CH₂–cyclopentyl | 3.64 | 3.91 |
| 46i | –(tetrahydrofuran-3-yl) | 2.87 | 3.56 |
| 47 | –(piperidin-4-yl) | 3.35 | 3.77 |
| 48 | –CH₂CH₃ (ethyl) | 3.52 | 3.87 |

Experimental Example 4. Behavioral Efficacy Test for Compounds of the Present Invention 4-1. Behavioral Efficacy Test Method Additional rats received the highest doses of drugs used to evaluate behavioral changes at 5, 10, 20, 30, 40, 50, and 60 min after intrathecal or intravenous administration to caudal vein. Motor functions were examined using the righting and placing-stepping reflexes. The righting reflex was evaluated by an immediate coordinated twisting of the body to an upright position when placing the rat horizontally with its back on the table. The placing-stepping reflex was induced by drawing the dorsum of hind paw across the edge of the table. Rats normally attempt to put their paws forward into a position for walking. Pinna and corneal reflexes were also assessed and judged as present or absent. Other abnormal behaviors, such as serpentine movement or tremors, were also evaluated.

4-2. Evaluation Results of Behavioral Efficacy

The analysis of the behavioral responses of Compound 28 and Compound 29 after intrathecal or intravenous administration revealed that the righting and position-stepping reflexes were normal, and pinna and corneal reflexes were present at the maximum dose used in this study. In addition, no obvious abnormal behavior changes were observed.

Although specific parts of the present invention have been described in detail, it will be apparent to those skilled in the art that these specific techniques are merely a preferred embodiment and that the scope of the present invention is not limited thereto. Therefore, the substantial scope of the present invention will be defined by the accompanying claims and their equivalents.

The invention claimed is:

1. A compound represented by General Formula 1 below, an isomer thereof, or a pharmaceutically acceptable salt thereof:

[General Formula 1]

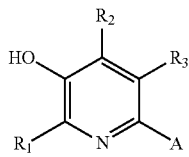

in the General Formula 1,
A is represented by Chemical Formula 2 below,

[Chemical Formula 2]

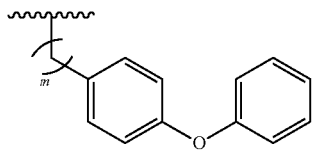

wherein m is an integer from 0 to 5;
$R_1$ is a propyl;
$R_2$ is a hydrogen atom, a straight or branched $C_0$-$C_6$ alkyl unsubstituted or substituted with carboxyl, sulfonyl, cyano, amide, tetrazolyl or

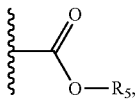

or together with $R_3$ forms a hetero 5- or 6-membered ring comprising at least one atom selected from the group consisting of N, O, S;
$R_3$ is a hydrogen atom, a straight or branched $C_1$-$C_6$ alkyl unsubstituted or substituted with carboxyl, or together with $R_2$ forms a hetero 5- or 6-membered ring; and
$R_5$ is a straight or branched $C_1$-$C_8$ alkyl unsubstituted or substituted with phenyl, pyrrolidinyl, piperidinyl, tetrahydrofuranyl, or 1,3-dioxo-1,3-dihydro-2H-isoindol-2-yl, $C_5$-$C_6$ cycloalkyl, or

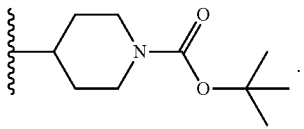

2. The compound, an isomer thereof, or a pharmaceutically acceptable salt thereof of claim 1, wherein,
m is an integer from 0 to 5;
$R_1$ is a propyl;
$R_2$ is a hydrogen atom, a straight or branched $C_1$-$C_3$ alkyl, —COOH, —CH=CHCOOH, —CH$_2$CH$_2$COOH, —CH$_2$NH$_2$, —CH$_2$NH—S(=O)$_2$—CH$_3$, cyano, or

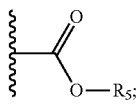

$R_3$ is a hydrogen atom, a straight or branched $C_1$-$C_3$ alkyl, or carboxyl (—COOH); and
$R_5$ is

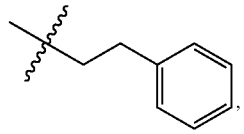

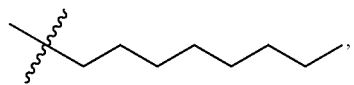

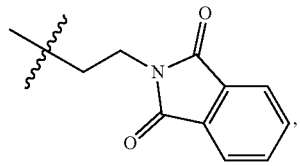

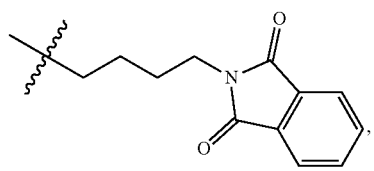

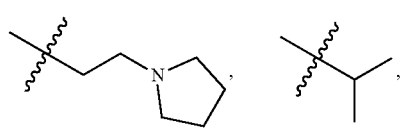

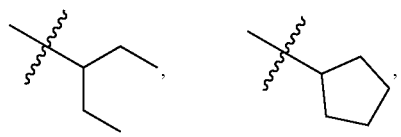

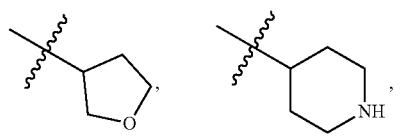

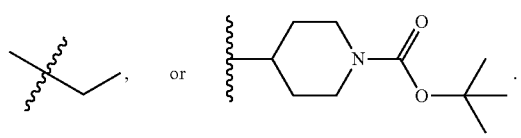

3. A 5-hydroxy pyridine-based compound represented by General Formula Ib below, an isomer thereof, or a pharmaceutically acceptable salt thereof:

[General Formula Ib]

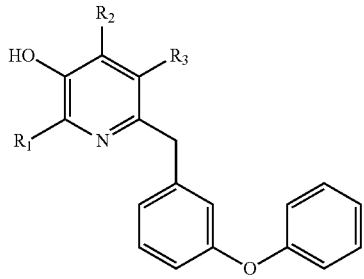

Ib in the General Formula Ib, $R_1$ is a propyl;

$R_2$ is a hydrogen atom, a straight or branched $C_1$-$C_3$ alkyl, —COOH, —CH=CHCOOH, —CH$_2$CH$_2$COOH, —CH$_2$NH$_2$, —CH$_2$NH—S(=O)$_2$—CH$_3$, cyano, or

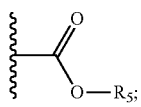

$R_3$ is a hydrogen atom, a straight or branched $C_1$-$C_3$ alkyl, or carboxyl (—COOH); and $R_5$ is

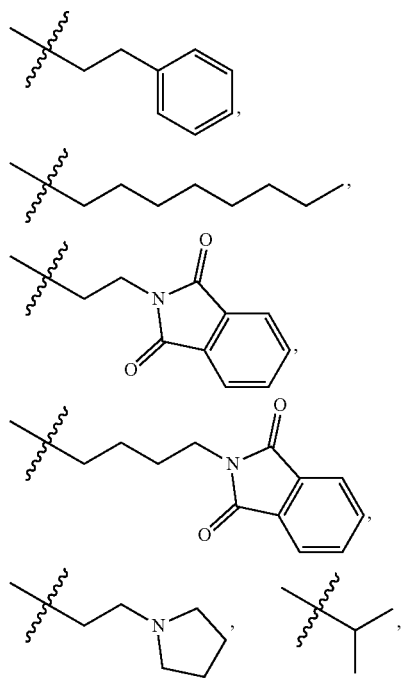

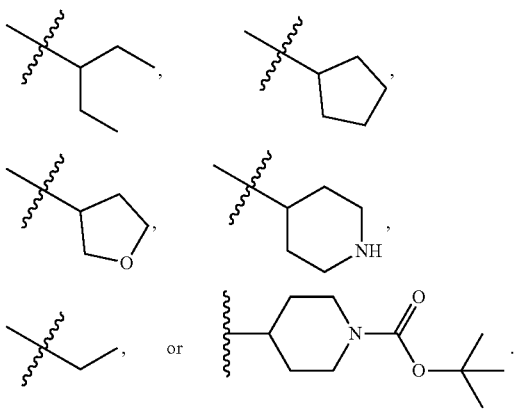

4. The 5-hydroxy pyridine-based compound, an isomer thereof, or a pharmaceutically acceptable salt thereof of claim 3, wherein the compound is represented by General Formula Ib' below:

[General Formula Ib']

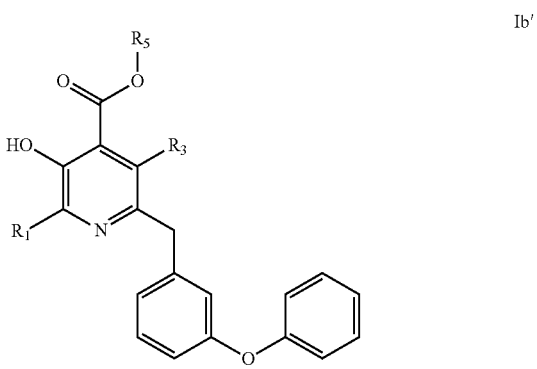

Ib' in the General Formula Ib', $R_1$ is a propyl;

$R_3$ is a hydrogen atom, or a straight or branched $C_1$-$C_3$ alkyl; and $R_5$ is

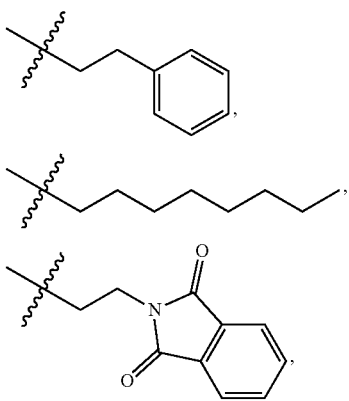

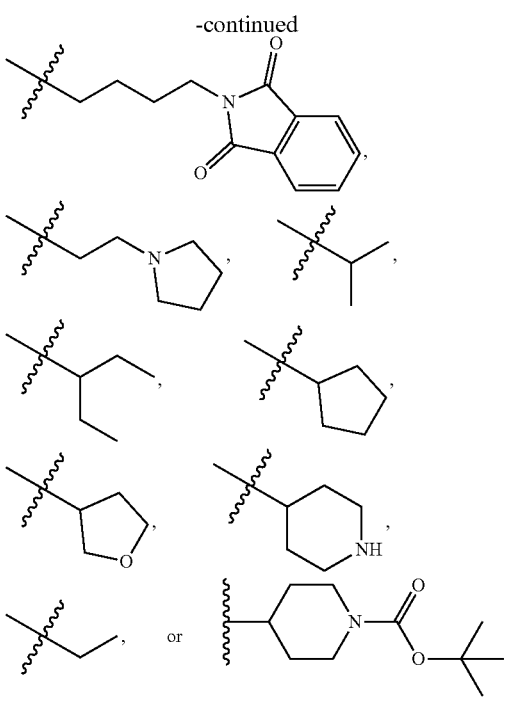

5. The compound, an isomer thereof or a pharmaceutically acceptable salt thereof of claim 1, wherein the compound represented by General Formula 1 is any one selected from the group consisting of: Dimethyl 5-hydroxy-2-(3-phenoxybenzyl)-6-propylpyridine-3,4-dicarboxylate (26); 5-Hydroxy-2-(3-phenoxybenzyl)-6-propylpyridine-3,4-dicarboxylic acid (27); Methyl 3-hydroxy-5-methyl-6-(3-phenoxybenzyl)-2-propylisonicotinate (28); 3-Hydroxy-5-methyl-6-(3-phenoxybenzyl)-2-propylisonicotinic acid (29); Methyl 3-(benzyloxy)-5-methyl-6-(3-phenoxybenzyl)-2-propylisonicotinate (30); (3-(Benzyloxy)-5-methyl-6-(3-phenoxybenzyl)-2-propylpyridin-4-yl)methanol (31); 4-(Hydroxymethyl)-5-methyl-6-(3-phenoxybenzyl)-2-propylpyridin-3-ol (32); 3-Hydroxy-5-methyl-6-(3-phenoxybenzyl)-2-propylisonicotinaldehyde (33); Ethyl (E)-3-(3-hydroxy-5-methyl-6-(3-phenoxybenzyl)-2-propylpyridin-4-yl)acrylate (34); (E)-3-(3-Hydroxy-5-methyl-6-(3-phenoxybenzyl)-2-propylpyridin-4-yl)acrylic acid (35); Ethyl 3-(3-hydroxy-5-methyl-6-(3-phenoxybenzyl)-2-propylpyridin-4-yl)propanoate (36); 3-(3-Hydroxy-5-methyl-6-(3-phenoxybenzyl)-2-propylpyridin-4-yl)propanoic acid (37) 3-Hydroxy-5-methyl-6-(3-phenoxybenzyl)-2-propylisonicotinonitrile (38); 3-(Benzyloxy)-5-methyl-6-(3-phenoxybenzyl)-2-propylisonicotinonitrile (39); (3-(Cyclohexa-2,4-dien-1-ylmethoxy)-5-methyl-6-(3-phenoxybenzyl)-2-propylpyridin-4-yl)methanamine (40); 4-(Aminomethyl)-5-methyl-6-(3-phenoxybenzyl)-2-propylpyridin-3-ol (41); N-((3-(Benzyloxy)-5-methyl-6-(3-phenoxybenzyl)-2-propylpyridin-4-yl)methyl)methanesulfonamide (42); N-((3-Hydroxy-5-methyl-6-(3-phenoxybenzyl)-2-propylpyridin-4-yl)methyl)methanesulfonamide (43); Phenethyl 3-hydroxy-5-methyl-6-(3-phenoxybenzyl)-2-propylisonicotinate (46a); Octyl 3-hydroxy-5-methyl-6-(3-phenoxybenzyl)-2-propylisonicotinate (46b); 2-phthalimidoethyl 3-hydroxy-5-methyl-6-(3-phenoxybenzyl)-2-propylisonicotinate (46c); 4-phthalimidobutyl 3-hydroxy-5-methyl-6-(3-phenoxybenzyl)-2-propylisonicotinate (46d); 2-(pyrrolidin-1-yl)ethyl 3-hydroxy-5-methyl-6-(3-phenoxybenzyl)-2-propylisonicotinate (46e); Isopropyl 3-hydroxy-5-methyl-6-(3-phenoxybenzyl)-2-propylisonicotinate (46f); Pentan-3-yl 3-hydroxy-5-methyl-6-(3-phenoxybenzyl)-2-propylisonicotinate (46g); Cyclopentyl 3-hydroxy-5-methyl-6-(3-phenoxybenzyl)-2-propylisonicotinate (46h); Tetrahydrofuran-3-yl 3-hydroxy-5-methyl-6-(3-phenoxybenzyl)-2-propylisonicotinate (46i); 1-(Tert-butoxycarbonyl)piperidin-4-yl 3-hydroxy-5-methyl-6-(3-phenoxybenzyl)-2-propylisonicotinate (46j); Piperidin-4-yl 3-hydroxy-5-methyl-6-(3-phenoxybenzyl)-2-propylisonicotinate (47); and Ethyl 3-hydroxy-5-methyl-6-(3-phenoxybenzyl)-2-propylisonicotinate (48).

6. A pharmaceutical composition comprising the compound of claim 1, an isomer thereof, or a pharmaceutically acceptable salt thereof as an active ingredient.

7. The pharmaceutical composition of claim 6, wherein the pharmaceutical composition is pharmaceutical composition for treating neuropathic pain or allodynia.

8. An P2X receptor antagonist, comprising the compound of claim 1, an isomer thereof, or a pharmaceutically acceptable salt thereof as an active ingredient.

9. A pharmaceutical composition comprising the compound of claim 3, an isomer thereof, or a pharmaceutically acceptable salt thereof as an active ingredient.

10. An P2X receptor antagonist, comprising the compound of claim 3, an isomer thereof, or a pharmaceutically acceptable salt thereof as an active ingredient.

* * * * *